United States Patent [19]
Ort et al.
[11] Patent Number: 5,463,081
[45] Date of Patent: Oct. 31, 1995
US005463081A

[54] ARYLSULFONYLUREAS, PROCESSES FOR THEIR PREPARATION, AND THEIR USE AS HERBICIDES AND GROWTH REGULATORS

[75] Inventors: Oswald Ort, Kelkheim; Klaus Bauer, Hanau; Hermann Bieringer, Eppstein/Taunus, all of Germany

[73] Assignee: Hoechst Aktiengesellschaft, Frankfurt, Germany

[21] Appl. No.: 94,194

[22] PCT Filed: Feb. 12, 1992

[86] PCT No.: PCT/EP92/00304

§ 371 Date: Sep. 21, 1993

§ 102(e) Date: Sep. 21, 1993

[87] PCT Pub. No.: WO92/13845

PCT Pub. Date: Aug. 20, 1992

[30] Foreign Application Priority Data

Feb. 12, 1991 [DE] Germany .......................... 41 04 227.1

[51] Int. Cl.$^6$ ...................... C07C 265/00; C07C 311/16; C07D 339/08; C07D 333/10

[52] U.S. Cl. ................................ 549/13; 549/22; 549/77; 549/230; 549/373; 549/451; 549/426; 549/496; 558/257; 560/11; 560/12; 560/330; 564/85; 564/86; 564/88

[58] Field of Search .............................. 558/257; 560/11, 560/14, 12, 330; 564/85, 86, 88; 549/13, 22, 77, 230, 373, 451, 426, 496

[56] References Cited

U.S. PATENT DOCUMENTS

| | | | |
|---|---|---|---|
| 3,965,173 | 6/1976 | Chubb et al. | 564/86 |
| 4,383,113 | 5/1983 | Levitt | 544/211 |
| 4,480,101 | 10/1984 | Meyer | 544/320 |
| 4,537,896 | 8/1985 | Claeson et al. | 514/330 |
| 4,551,531 | 11/1985 | Meyer et al. | 544/320 |
| 5,104,441 | 4/1992 | Hamprecht | 544/321 |
| 5,143,937 | 9/1992 | Lang et al. | 514/603 |

FOREIGN PATENT DOCUMENTS

| | | |
|---|---|---|
| 0030138 | 6/1981 | European Pat. Off. . |
| 0084020 | 7/1983 | European Pat. Off. . |
| 0174212 | 3/1986 | European Pat. Off. . |
| 0291851 | 11/1988 | European Pat. Off. . |
| 2493702 | 5/1982 | France . |
| 2090136 | 7/1982 | United Kingdom . |

*Primary Examiner*—Allen J. Robinson
*Assistant Examiner*—Mary C. Cebulak
*Attorney, Agent, or Firm*—Curtis, Morris & Safford

[57] ABSTRACT

The invention relates to novel intermediates for the preparation of a certain group of novel phenylsulfonylurea herbicides, which herbicides are particularly advantageous for use in crop protection. The novel intermediate compounds are of the formula II

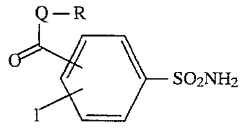

(II)

and of the formula VI,

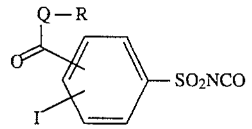

(VI)

as defined in the specification and claims. The intermediate compounds may be used to prepare herbicidal and plant growth regulating compounds of the formula I or salts thereof:

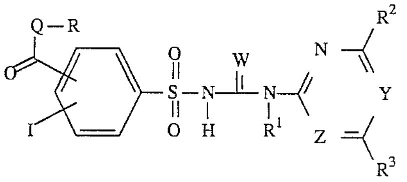

(I)

as defined in the specification.

The herbicides so obtained are particularly suitable for selectively controlling weeds.

21 Claims, No Drawings

ARYLSULFONYLUREAS, PROCESSES FOR THEIR PREPARATION, AND THEIR USE AS HERBICIDES AND GROWTH REGULATORS

DESCRIPTION

This application is a 371 of PCT/EP92/00304 filed Feb. 12, 1992. The invention relates to the field of crop protection agents, in particular selective herbicides and growth regulators of the type of the phenylsulfonylureas which are substituted by a heterocycle.

EP-A-007,687 has already disclosed, inter alia, sulfonylureas of the formula (1)

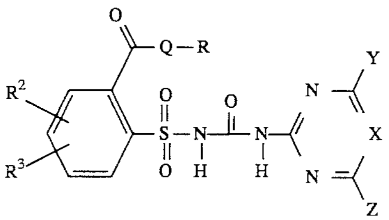
(1)

in which $R^2$ is H, Cl, Br, F, $(C_1-C_3)$alkyl, $-NO_2$, $-SO_2CH_3$, $-OCH_3$, $-SCH_2$, $-CF_3$, $-N(CH_3)_2$, $-NH_2$ or $-CN$; $R^3$ is H, Cl, Br, F or $CH_3$; X is CH or N, Q is O, S or optionally substituted NH; and Y and Z are H, Cl or various organic radicals. The compounds have been described as herbicides and plant growth regulators.

EP-A-0,291,851 and DE-A-3,900,472 have disclosed herbicidal and plant growth-regulating sulfonylureas of the formula (2)

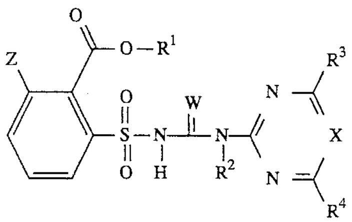
(2)

in which Z is F, Cl or Br, $R^1$ is H, optionally substituted alkyl, alkenyl, alkynyl or cycloalkyl, $R^2$ is H,$CH_3$ or $C_2H_5$, $R^3$ is H, F, Cl, Br, $CH_3$ or $OCH_3$, $R^4$ is H, $CH_3$, $(C_1-C_4)$alkoxy and X is CH or N.

U.S. Pat. No. 4,566,898 furthermore describes the sulfonylurea of the formula (3)

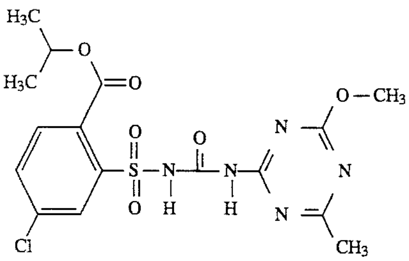
(3)

as a herbicide which has outstanding properties, in particular for controlling black grass in barley and wheat.

Surprisingly, it has now been found that some iodinated arylsulfonylureas have advantageous properties.

The present invention therefore relates to compounds of the formula (I) and salts thereof,

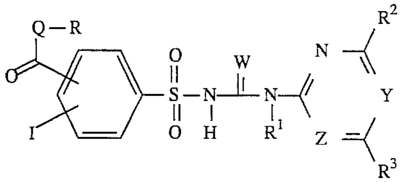
(I)

where

Q is oxygen, sulfur or $-N(R^4)-$, preferably O or S, in particular O;

W is oxygen or sulfur, preferably O;

Y and Z independently of one another are CH or N, where Y and Z are not simultaneously CH, preferably Y is CH or N and Z is N;

R is hydrogen; $(C_1-C_{12})$alkyl; $(C_2-C_{10})$alkenyl; $(C_2-C_{10})$alkynyl; $(C_1-C_6)$alkyl, which is mono substituted to tetrasubstituted by radicals selected from the group comprising halogen, $(C_1-C_4)$alkoxy, $(C_1-C_4)$thioalkyl, $-CN$, $(C_2-C_5)$alkoxycarbonyl and $(C_2-C_6)$alkenyl; $(C_3-C_8)$cycloalkyl which is unsubstituted or substituted by radicals selected from the group comprising $(C_1-C_4)$alkyl, $(C_1-C_4)$alkoxy, $(C_1-C_4)$alkylthio and halogen; $(C_5-C_8)$cycloalkenyl; phenyl $(C_1-C_4)$alkyl which is unsubstituted or substituted in the phenyl radical; or a radical of the formulae A-1 to A-10

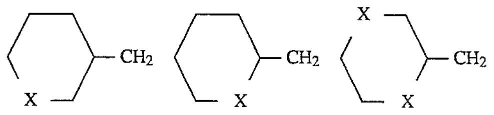
A-1 A-2 A-3

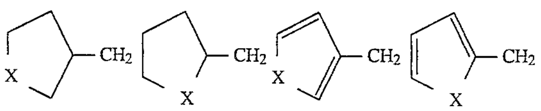
A-4 A-5 A-6 A-7

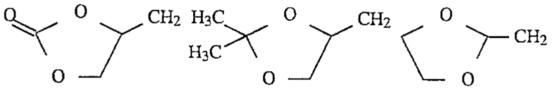
A-8 A-9 A-10 where

X is O, S, S(O) or $SO_2$;

$R^2$ is hydrogen or $(C_1-C_3)$alkyl;

$R^2$ is hydrogen, halogen, preferably chlorine, $(C_1-C_3)$alkyl, $(C_1-C_3)$alkoxy, where the two last-mentioned radicals are unsubstituted or monosubstituted or polysubstituted by halogen or $(C_1-C_3)$alkoxy;

$R^3$ is hydrogen, halogen, preferably chlorine, $(C_1-C_3)$alkyl, $(C_1-C_3)$alkoxy or $(C_1-C_3)$alkylthio, where the above-mentioned alkyl-containing radicals are unsubstituted or monosubstituted or polysubstituted by halogen or monosubstituted or disubstituted by $(C_1-C_3)$alkoxy or $(C_1-C_3)$alkylthio; or a radical of the formula $NR^5R^6$, $(C_1-C_6)$-cycloalkyl, $(C_2-C_4)$alkenyl, $(C_2-C_4)$alkynyl, $(C_3-C_4)$alkenyloxy or $(C_1-C_6)$alkynyloxy;

$R^4$ is hydrogen, $(C_1-C_4)$alkyl or $(C_1-C_4)$alkoxy and $R^5$ and $R^6$ independently of one another are hydrogen, $(C_1-C_4)$alkyl, $(C_3-C_4)$alkenyl, $(C_1-C_4)$haloalkyl or $(C_1-C_4)$alkoxy.

In formula (I) and in what follows, alkyl, alkoxy, haloalkyl, alkylamino and alkylthio radicals as well as the corresponding unsaturated and/or substituted radicals can in each case be straight-chain or branched. Alkyl radicals, also in composite meanings such as alkoxy, haloalkyl etc., are, for example, methyl, ethyl, n- or i-propyl, n-, i-, t- or 2-butyl etc. Alkenyl and alkynyl radicals have the meanings of the unsaturated radicals which are possible and which correspond to the alkyl radicals, such as, for example, 2-propenyl, 2- or 3-butenyl, 2-propynyl and 2- or 3-butynyl. Halogen is fluorine, chlorine, bromine or iodine. Aryl is preferably a carbocyclic or heterocyclic aromatic ring which can optionally be fused with an aliphatic or aromatic ring; in particular, aryl is phenyl. Substituted phenyl is phenyl which is substituted for example by one or more, preferably one to three, radicals selected from the group comprising halogen, $(C_1–C_4)$alkyl, $(C_1–C_4)$alkoxy, $(C_1–C_4)$haloalkyl, $(C_1–C_4)$thioalkyl, $(C_2–C_5)$alkoxycarbonyl, $(C_2–C_5)$alkylcarbonyloxy, carboxamide, $(C_2–C_5)$alkylcarbonylamino, $(C_2–C_5)$alkylaminocarbonyl, di-$[(C_1–C_4)$alkyl]aminocarbonyl and nitro. The same applies analogously to substituted aryl.

The compounds of the formula (I) can form salts in which the hydrogen of the —$SO_2$—NH— group is replaced by a cation which is suitable for agriculture. Examples of these salts are metal salts, in particular alkali metal salts or alkaline earth metal salts, but also ammonium salts or salts with organic amines. Salt formation can also be effected by an addition reaction of a strong acid with the heterocycle moiety of the compounds of the formula (I). Examples of acids which are suitable for this purpose are HCl, $HNO_3$, trichloroacetic acid, acetic acid or palmitic acid.

Some compounds of the formula (I) can contain one or more asymmetric carbon atoms or else double bonds which are not mentioned individually in the formula (I). However, formula (I) embraces all possible stereoisomers which are defined by their specific spatial form such as enantiomers, diastereomers, Z and E isomers, which can be obtained from mixtures of the stereoisomers by customary methods or, alternatively, by stereoselective reactions in combination with the use of stereochemically pure starting materials. The invention thus relates to the stereo-isomers mentioned in pure form and also their mixtures.

Compounds of the formula (I) according to the invention, or salts thereof, which are of particular interest are those where R is hydrogen; $(C_1–C_6)$alkyl; $(C_2–C_6)$alkenyl; $(C_2–C_6)$-alkynyl; $(C_1–C_4)$alkyl which is monosubstituted to tetrasubstituted, preferably monosubstituted, by radicals selected from the group comprising halogen, $(C_1–C_2)$alkoxy, $(C_1–C_2)$thioalkyl, $(C_2–C_3)$alkoxycarbonyl and $(C_2–C_4)$alkenyl; $(C_5–C_6)$cycloalkyl which is unsubstituted or substituted by radicals selected from the group comprising $(C_1–C_4)$alkyl, $(C_1–C_4)$alkoxy, $(C_1–C_4)$alkylthio and halogen; $(C_5–C_6)$cycloalkenyl; benzyl which is unsubstituted or substituted in the phenyl radical by one to three radicals selected from the group comprising halogen, $(C_1–C_2)$alkyl, $(C_1–C_2)$alkoxy, $(C_1–C_2)$haloalkyl, $(C_1–C_2)$thioalkyl and $(C_2–C_4)$alkoxycarbonyl, or a radical of the abovementioned formulae A-1 to A-10, where X is O, S, S(O) or $SO_2$, preferably O.

Compounds of the formula (I) according to the invention, or salts thereof, which are of particular interest are those where $R^1$ is hydrogen or $CH_3$;

$R^2$ is hydrogen, halogen, preferably chlorine, $(C_1–C_2)$alkyl, $(C_1–C_2)$alkoxy, where the two last-mentioned radicals are unsubstituted or monosubstituted or polysubstituted by halogen or $(C_1–C_3)$alkoxy;

$R^3$ is hydrogen, halogen, preferably chlorine, $(C_1–C_2)$alkyl, $(C_1–C_2)$alkoxy or $(C_1–C_2)$alkylthio, where the abovementioned alkyl-containing radicals are unsubstituted or monosubstituted or polysubstituted by halogen or monosubstituted or disubstituted by $(C_1–C_2)$alkoxy or $(C_1–C_2)$alkylthio; or a radical of the formula $NR^5R^6$;

$R^4$ is hydrogen or $(C_1–C_2)$alkyl and $R^5$ and $R^6$ independently of one another are hydrogen or $(C_1–C_2)$alkyl.

Preferred compounds of the formula (I) according to the invention or salts thereof are those in which W is oxygen and $R^1$ is hydrogen or $CH_3$.

Particularly preferred compounds of the formula (I) or salts thereof are those in which Y is CH or N, Z is N and $R^2$ is hydrogen, $CH_3$, $CH_2CH_3$, $OCH_3$, $OCH_2CH_3$, $OCHF_2$, Cl and $R^3$ is hydrogen, $CH_3$, $CH_2CH_3$, $OCH_3$, $OCH_2CH_3$, $OCHF_2$, $NH(CH_3)$, $N(CH_3)_2$, $CF_3$, $OCH_2CF_3$ or Cl.

Other preferred compounds according to the invention are those which exhibit a combination of the abovementioned preferred features.

The present invention furthermore relates to processes for the preparation of the compounds of the formula (I) or salts thereof, which comprise a) reacting a compound of the formula (II)

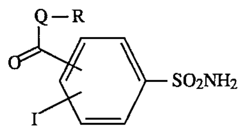
(II)

with a heterocyclic carbamate of the formula (III)

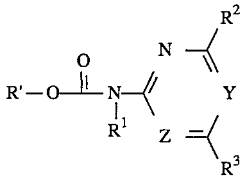
(III)

where R' is unsubstituted or substituted aryl or alkyl, preferably unsubstituted or substituted phenyl or $(C_1–C_4)$alkyl, in particular phenyl or methyl, or b) reacting a phenylsulfonyl carbamate of the formula (IV)

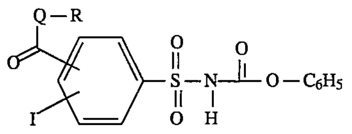
(IV)

with an aminoheterocycle of the formula (V)

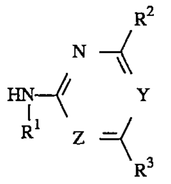
(V)

c) reacting a sulfonyl isocyanate of the formula (VI)

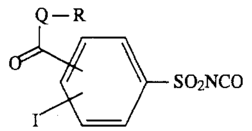

(VI)

with an aminoheterocycle of the formula (V) mentioned under b).

The compounds of the formula (II) and (III) are reacted by means of base catalysis in an inert solvent, such as, for example, acetonitrile, dioxane or tetrahydrofuran at temperatures of between 0° C. and the boiling point of the solvent. 1,8-Diazabicyclo[5.4.0]undec-7-ene (DBU) is preferably used as the base.

The sulfonamides (II) are novel compounds; this invention also relates to these compounds and to their preparation (see Tables 1a and 1b further below). They are obtained starting from corresponding sulfonyl halides, preferably corresponding sulfochlorides, which react either directly with ammonia or with tert.-butylamine, followed by elimination of the protective groups, for example by treatment with trifluoroacetic acid, to give the sulfonamides of the formula (II). The sulfonyl halides which can be used in the process can be obtained from the corresponding anilines by diazotization and exchange of the diazo group with sulfur dioxide in the presence of a catalyst such as copper(I) chloride in hydrochloric acid or acetic acid, cf. Meerwein, Chem. Ber. 90, 841–52 (1957).

The carbamates of the formula (III) can be prepared by methods as are described in the South African Patent Applications 82/5671 and 82/5045 (or EP-A-0,072,347 and EP-A-0,070,802, respectively).

The compounds (IV) are preferably reacted with the amino-heterocycles (V) in inert, aprotic solvents, such as, for example, dioxane, acetonitrile or tetrahydrofuran, at temperatures of between 0° C. and the boiling point of the solvent. The starting compounds required, of the formula (V), are known or can be prepared by methods known in principle, see "The Chemistry of Heterocyclic Compounds", Vol. XVI, (1962), Interscience Publ., New York & London, and Supplement I of this manual. Amino-substituted triazine derivatives are reviewed by Smolin and Rapaport in "The Chemistry of Heterocyclic Compounds", Vol. XIII, (1959), Interscience Publ., New York & London. The iodinated phenylsulfonyl carbamates (IV) are obtained analogously to processes given in EP-A-0,044,808 or EP-A-0,237,292.

The iodinated arylsulfonyl isocyanates of the formula (VI) are novel compounds and also a subject of the invention. They can be prepared analogously to methods of EP-A-0,184,385 and reacted with the abovementioned amino-heterocycles of the formula (V).

The salts of the compounds of the formula (I) are preferably prepared in inert solvents, such as, for example, water, methanol, dichloromethane or acetone, at temperatures of 0°–100°. Examples of suitable bases for the preparation of the salts according to the invention are alkali metal carbonates, such as potassium carbonate, alkali metal hydroxides and alkaline earth metal hydroxides, ammonia or ethanolamine. Acids which are particularly suitable for salt formation are HCl, $HNO_3$, trichloroacetic acid, acetic acid or palmitic acid.

The compounds of the formula (I) according to the invention have an excellent herbicidal activity against a broad range of economically important monocotyledon and dicotyledon weeds. The active substances act equally well on perennial weeds which produce shoots from rhizomes, rootstocks or other perennial organs and which cannot be easily controlled. In this context, it does not matter if the substances are applied before sowing, as a pre-emergence treatment or post-emergence treatment. Some representatives of the monocotyledon and dicotyledon weed flora which can be controlled by the compounds according to the invention may be mentioned individually as examples, but this is not to be taken to mean a restriction to certain species.

The monocotyledon weed species controlled include, for example, Avena, Lolium, Alopecurus, Phalaris, Echinochloa, Digitaria, Setaria etc. and Cyperus species from the annual group, and the perennial species include Agropyron, Cynodon, Imperata and Sorghum etc., and also perennial Cyperus species.

Of the dicotyledon weed species, the range of action covers, for example, Galium, Viola, Veronica, Lamium, Stellaria, Amaranthus, Sinapis, Ipomoea, Matricaria, Abutilon, Sida etc. from the annual plants and Convolvulus, Cirsium, Rumex, Artemisia etc. from the perennial weeds.

Excellent control of weeds occurring under the specific culture conditions in rice, such as, for example, Sagittaria, Alisma, Eleocharis, Scirpus, Cyperus etc., by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely. When, in the post-emergence method, the active substances are applied to the green parts of the plants, growth also stops dramatically very soon after the treatment, and the weed plants remain in the growth stage of the time of application, or, after a certain period of time, die more or less rapidly so that competition by the weeds, which is detrimental for the crop plants, can thus be prevented at a very early stage and in a sustained manner by using the novel compounds according to the invention.

Even though the compounds according to the invention have an excellent herbicidal activity against monocotyledon and dicotyledon weeds, crop plants of economically important crops such as, for example, wheat, barley, rye, maize, rice, sugar beet, cotton and soya, are damaged to a negligible extent only, or not at all. Thus, the present compounds are very suitable for selectively controlling undesired plant growth in agricultural plantations of useful plants.

In addition, the compounds according to the invention have plant growth-regulating properties in crop plants. They intervene in the plant metabolism in a regulating manner and can thus be employed for facilitating harvesting, such as, for example, by provoking desiccation, abscission and stunted growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The compounds according to the invention can be formulated in many ways, depending on the prevailing biological and/or chemicophysical parameters. Examples of possible formulations are the following: wettable powders (WP), water-soluble powders (SP), water-soluble concentrates, emulsifiable concentrates (EC), emulsions (EW) such as oil-in-water and water-in-oil emulsions, sprayable solutions or emulsions, suspension concentrates (SC), dispersions on an oil or water basis, oil-miscible solutions, suspoemulsions, capsule suspensions (CS), dusts (DP), seed-dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie", [Chemical Technology], Volume 7, G. Hauser Verlag Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Galdwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's "Detergents and Emulsifiers Annual" MG Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active Ethylene Oxide Adducts], Wiss. Verlagsgesell., Stuttgart 1976; Winnacker-Küchler, "Chemische Technologie", [Chemical Technology], Volume 7, G. Hauser Verlag Munich, 4th Ed. 1986.

Wettable powders are preparations which are uniformly dispersible in water and which, besides the active substance, also contain wetting agents, for example, polyoxyethylated alkylphenols, polyoxyethylated fatty alcohols and fatty a mines, fatty alcohol polyglycol ether sulfates, alkanesulfonates or alkylarylsulfonates, and dispersing agents, for example sodium ligninsulfonate, sodium 2,2'-dinaphthylmethane-6,6,-disulfonate, sodium dibutylnaphthalenesulfonate and also sodium oleylmethyltauride, in addition to a diluent or inert substance.

Emulsifiable concentrates are prepared, for example, by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as calcium dodecylbenzenesulfonate or non-ionic emulsifiers, such as fatty acid polyglycol esters, alkylaryl polyglycol ethers, fatty alcohol polyglycol ethers, propylene oxide/ethylene oxide condensation products (for example block polymers), alkyl polyglycol ethers, sorbitan fatty acid esters, polyoxyethylene sorbitan fatty acid esters or polyoxyethylene sorbitol esters.

Dusts are obtained by grinding the active substance with finely divided solid substances, for example talc or natural clays, such as kaolin, bentonite or pyrophyllite, or diatomaceous earth.

Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Disk granules, fluidized-bed granules, extruder granules and spray granules can be prepared by conventional methods; see, for example, methods in "Spray Drying Handbook", 3rd Ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8–57.

Further information on the formulation of crop protection agents can be found, for example, in G. G. Klingman, "Weed Control as a Science", John Wiley and Sons, Inc., New York, 1961, pages 81–96 and J. D. Freyer's, A. Evans, "Weed Control Bandbook", 5th Ed., Blackwell Scientific Publications, Oxford, 1968, pages 101–103.

The active substance concentration in wettable powders is, for example, about 10 to 90% by weight; the remainder to 100% by weight is composed of conventional formulation components. In the case of emulsifiable concentrates, the active substance concentration can be about 1 to 80% by weight. Formulations in the form of dusts usually contain 1 to 20% by weight of active substance, sprayable solutions about 0.2 to 20% by weight. In the case of granules the active substance content depends partly on whether the active compound is liquid or solid. The water-dispersible granules usually contain between 10 and 90% by weight of active substance.

In addition, the active substance formulations mentioned contain, if appropriate, the adhesives, wetting agents, dispersing agents, emulsifiers, penetrants, solvents, fillers or carriers which are conventional in each case.

Based on these formulations, it is also possible to prepare combinations with other substances which are active in arable farming, for example pesticides such as insecticides, acaracides, fungicides and herbicides, and/or fertilizers and/or growth regulators, for example in the form of a readymix or as a tank mix.

In particular, the compounds of the formula (I) according to the invention can be used together with further herbicides as are known, for example, from Weed Research 26, 441–5 (1986) or "The Pesticide Manual", 9th Edition, The British Crop Protection Council, 1990, England. The following active substances may be mentioned as examples of herbicides which are known from the literature and which can be combined according to the invention with the compounds of the formula (I) (the common name, or manufacturer's code, of each of the active substances is in bold print and the chemical name is then in ordinary typeface, see scheme):

Common name (or Manufacturer's code) Chemical name [Scheme]

AC 263222 2-[4,5-dihydro-4-methyl-4-(1-methylethyl)-5 -oxo-1H-imidazol-2-yl]-5-methyl-3-pyridinecarboxylic acid; acetochlor 2-chloro-N-(ethoxymethyl)-N-(2-ethyl-6 -methylphenyl)acetamide;

acifluorfen 5-[2-chloro-4-(trifluoromethyl)phenoxy]-2 -nitrobenzoic acid;

aclonifen 2-chloro-6-nitro-3-phenoxyaniline;

AKB 7088 methyl [[[1- [5- [2- chloro-4 -(trifluoromethyl)phenoxy]-2-nitrophenyl]-2 -methoxyethylidene] amino]oxy]acetate;

alachlor 2-chloro-N-(2,6-diethylphenyl)-N-(methoxymethyl)acetamide;

alloxydim methyl 3-[1-(allyloxyimino)-butyl]-4-hydroxy-6, 6-dimethyl-2-cyclohex-3-enecarboxylate;

ametryn N-ethyl-N'-(1-methylethyl)-6-(methylthio)-1,3,5 -triazine-2,4-diamine;

amidosulfuron 1-[N-Methyl-N-(methylsulfonyl)-aminosulfonyl] -3-(4,6-dimethoxypyrimidin-2-yl)urea;

amitrole 1H-1,2,4-triazol-3-amine;

AMS ammonium sulfamate;

anilofos S-[2-[(4-chlorophenyl)(1-methylethyl)amino]-2 -oxoethyl] O,O-dimethylphosphorodithioate;

asulam methyl [(4-aminophenyl)sulfonyl]carbamate;

atrazine 6-chloro-N-ethyl-N'-(1-methylethyl)-1,3,5 -triazine-2,4-diamine;
aziprotryn 2-azido-N-(1-methylethyl)-6-methylthio-1,3,5 -triazin-2-amine;
barban 4-chloro-2-butynyl 3-chlorophenylcarbamate;
BAS 516 H 5-fluoro-2-phenyl-4H-3,1-benzoxazin-4-one;
benazolin 4-chloro-2-oxo-3(2H)-benzothiazoleacetic acid;
benfluralin N-butyl-N-ethyl-2,6-dinitro-4-(trifluoromethyl-)benzenamine;
benfuresate 2,3-dihydro-3,3-dimethylbenzofuran-5-yl ethanesulfonate;
bensulfuron-methyl methyl 2-[[[[(4,6-dimethoxy-2 -pyrimidinyl)amino]carbonyl]amino]sulfonyl]methyl]benzoate;
bensulideO,O-bis-(1-methylethyl)S-[ 2-[(phenylsulfonyl)amino]ethyl]phosphorodithioate;
bentazone 3-(1-methylethyl)-1H-2,1,3-benzothiadiazin-4(3H)-one, 2,2-dioxide;
benzofenap 2-[[4-(2,4-dichloro-3-methylbenzoyl)-1,3 -dimethyl-1H-pyrazol-5-yl]oxy]-1-(4-methylphenyl)ethanone;
benzofluor N-[4-(ethylthio)-2-(trifluoromethyl)phenyl] -methanesulfonamide;
benzoylprop-ethylethylN-benzoyl-N-(3,4-dichlorophenyl)alaninate;
benzthiazuron N-2-benzothiazolyl-N'-methylurea;
bialaphos 4-(hydroxymethylphosphinyl)-L-2-aminobutanoyl-L-alanyl-L-alanine;
bifenox methyl 5-(2,4-dichlorophenoxy)-2-nitrobenzoate;
bromacil bromo-6-methyl-3-(1-methylpropyl)-2,4(1H, 3H)pyrimidinedione;
bromobutide N-[(1,1-dimethyl)methylphenyl]-2-bromo-3,3 -dimethylbutyramide;
bromofenoxim 3,5-dibromo-4-hydroxybenzaldehyde O-(2,4 -dinitrophenyl)oxime;
bromoxynil 3,5-dibromo-4-hydroxybenzonitrile;
bromuron N'-(4-bromophenyl)-N,N-dimethylurea;
buminafos dibutyl [1-(butylamino)cyclohexyl]phosphonate;
butachlor N-(butoxymethyl)-2-chloro-N-(2,6-diethylphenyl)acetamide;
butamifos O-ethyl O-(5-methyl-2-nitrophenyl) (1-methylpropyl)phosphoramidothioate;
butenachlor (Z)-N-but-2-enyloxymethyl-2-chloro-2',6' -diethylacetanilide;
busoxinone 3-[5-(1,1-dimethylethyl)-isoxazol-3-yl]-4 -hyroxy-1-methyl-2-imidazolidinone; buthidazole 3-[5-(1,1-dimethylethyl)-1,3,4 -thiadiazol-2-yl]-4-hydroxy-1-methyl-2-imidazolidinone;
butralin 4-(1,1-dimethylethyl)-N-(1-methylpropyl)-2,6 -dinitrobenzenamine;
butylate S-ethyl bis(2-methylpropyl)carbamothioate;
C 4874 (tetrahydro-2-furanyl)methyl 2-[4-[(6-chloro-2 -quinoxalinyl)oxy]phenoxy]propanoate;
carbetamide (R)-N-ethyl-2-[[(phenylamino)carbonyl] -oxy] propanamide;
CDAA 2-chloro-N,N-di-2-propenylacetamide;
CDEC 2-chloroallyl diethyldithiocarbamate;
CGA 184927 2-propynyl 2-[4-[(5-chloro-3-fluoro-2 -pyridinyl)oxy]phenoxy]propanoate;
chlomethoxyfen 4-(2,4-dichlorophenoxy)-2-methoxy-1 -nitrobenzene;
chloramben 3-amino-2,5-dichlorobenzoic acid;
chlorbromuron 3-(4-bromo-3-chlorophenyl)-1-methoxy-1 -methylurea;
chlorbufaml-methyl-2-propynyl (3-chlorophenyl)carbamate;
chlorfenac 2,3,6-trichlorobenzeneacetic acid;
chlorflurecol-methyl methyl 2-chloro-9-hydroxy-9H-fluorene-9-carboxylate;
chloridazon 5-amino-4-chloro-2-phenyl-3(2H)-pyridazinone;
chlorimuron ethyl ethyl 2-[[[[(4-chloro-6-methoxy-2 -pyrimidinyl)amino]carbonyl]amino]sulfonyl]benzoate;
chlornitrofen 1,3,5-trichloro-2-(4-nitrophenoxy)benzene;
chlorotoluron N'-(3-chloro-4-methylphenyl)-N,N-dimethylurea;
chloroxuron N'-[4-(4-chlorophenoxy)phenyl]-N,N-dimethylurea;
chlorpropham 1-methylethyl 3-chlorophenylcarbamate;
chlorsulfuron 2-chloro-N-[[(4-methoxy-6-methyl-1,3,5 -triazin-2-yl)amino]carbonyl]benzenesulfonamide;
chlorthal-dimethyl dimethyl 2,3,5,6-tetrachloro-1,4 -benzenedicarboxylate;
chlorthiamid 2,6-dichlorobenzenecarbothioamide;
cinmethylin exo-1-methyl-4-(1-methylethyl)- 2-[(2-methylphenyl)methoxy]-7-oxabicyclo[2.2.1]heptane;.
cinosulfuron 1-(4,6-dimethoxy-1,3,5-triazin-2-yl)3-[2 -(2-methoxyethoxy)phenylsulfonyl]urea;
clethodim (E,E)-2-[1-[[(3-chloro- 2-propenyl)oxy]imino]-propyl]-5-[2-(ethylthio)propyl]-3-hydroxy-2-cyclohexen-1-one;
clomazone 2-[(2-chlorophenyl)methyl]-4,4-dimethyl-3 -isoxazolidinone;
clomeprop [(2,4-dichloro-3-methylphenyl)oxy]-2-propionanilide;
cloproxydim (E,E)-2-[1-[[(3-chloro-2 -propenyl)oxy]-imino]butyl]-5-[ 2-(ethylthio)propyl]-3-hydroxy-2-cyclohexen-1-one;
clopyralid 3,6-dichloro-2-pyridinecarboxylic acid;
cyanazine 2-[[4-chloro-6-(ethylamino)-1,3,5-triazin-2 -yl] amino]-2-methylpropanenitrile;
cycloate S-ethyl cyclohexylethylcarbamothioate;
cycloxydim 2-[1-(ethoxyimino)butyl]- 5-(tetrahydrothiopyran-3-yl)-3-hydroxy-2-cyclohexen-1-one;
cycluron 3-cyclooctyl-1-dimethylurea;
cyperquat 1-methyl-4-phenylpyridinium;
cyprazine 2-chloro-4-(cyclopropylamino)-6-(isopropylamino)-s-triazine;
cyprazole N-[5-(2-chloro-1,1-dimethylethyl)-1,3,4 -thiadiazol-2-yl]-cyclopropanecarboxamide;
2,4-DB 4-(2,4-dichlorophenoxy)butanoic acid;
dalapon 2,2-dichloropropanoic acid;
desmediphamethyl[3-[[(phenylamino)carbonyl]oxy]phenyl] -carbamate;
desmetryn 2-(isopropylamino)-4-(methylamino)-6 -(methylthio)s-triazine;
di-allate S-(2,3-dichloro-2-propenyl)bis(1 -methylethyl)carbamothioate;
dicamba 3,6-dichloro-2-methoxybenzoic acid;
dichlobenil 2,6-dichlorobenzonitrile;
dichlorprop 2-(2,4-dichlorophenoxy)propanoic acid;
diclofop-methyl methyl 2-[4-(2,4-dichlorophenoxy)phenoxy]-propanoate;
diethatyl N-(chloroacetyl)-N-(2,6-diethylphenyl)glycine;
difenoxuron N'-[4-(4-methoxyphenoxy)phenyl]-N,N-dimethylurea;
difenzoquat 1,2-dimethyl-3,5-diphenyl-1H-pyrazolium;
diflufenican N-(2,4-difluorophenyl)-2 -[3-(trifluoromethyl)-phenoxy]-3-pyridinecarboxamide;
dimefuron N'-[3-chloro-4-[5-(1,1 -dimethylethyl)-2-oxo-1,3,4-oxadiazol-3(2H)-yl]phenyl]-N,N-dimethylurea;
dimethachlor 2-chloro-N-(2,6-dimethylphenyl)-N-(2 -methoxyethyl)acetamide;
dimethametryn N-(1,2-dimethylpropyl)-N'-ethyl-6 -(methylthio)-1,3,5-triazine-2,4-diamine;
dimethipin2,3-dihydro-5,6-dimethyl-1,4-dithiin,1,1,4,4 -tetraoxide;

dinitramine $N^3$,$N^3$-diethyl-2,4 -dinitro-6-(trifluoromethyl)-1,3-benzenediamine;

dinoseb 2-(1-methylpropyl)-4,6-dinitrophenol;

dinoterb 2-(1,1-dimethylethyl)-4,6-dinitrophenol;

diphenamid N,N-dimethyl-2,2-diphenylacetamide;

dipropetryn 6-ethylthio-N,N'-bis(1-methylethyl)-1,3,5 -triazine-2,4-diamine;

diquat 6,7 dihydrodipyrido[1,2-a:2',1'-c]pyrazinediium, dithiopyr 2-(difluoromethyl)-4-(2 -methylpropyl)-6-(trifluoromethyl)-3,5-pyridinedicarbothioic acid;

diuron N'-(3,4-dichlorophenyl)-N,N-dimethylurea;

DNOC 2-methyl-4,6-dinitrophenol;

DPX-A7881methyl 2-[[[[(4-ethoxy-6-N-(methyl)amino-1,3,5 -triazin-2-yl]amino]carbonyl]amino]sulfonyl]benzoate;

DPX-E9636 N-[[(4,6-dimethoxy-2-pyrimidinyl)amino] -carbonyl]-3-(ethylsulfonyl)-2-pyridinesulfonamide;

dymron N-(4-methylphenyl)-N'-(1-methyl-1-phenylethyl)urea;

eglinazine-ethyl ethyl N-[4-chloro-6-(ethylamino)-1,3,5 -tria-zin-2-yl]glycinate;

EL 177 5-cyano-1-(1,1-dimethylethyl)-N-methyl- 3H-pyrazole-4-carbo xamide;

endothal 7-oxabicyclo[2.2.1]heptane-2,3-dicarboxylic acid;

EPTC S-ethyl dipropylcarbamothioate;

esprecarb S-(methylphenyl) N-ethyl-N-(1,2-dimethyl)propylcarbamothioate;

ethalfluralin N-ethyl-N-(2-methyl-2-propenyl)-2,6 -dinitro-4-(trifluoromethyl)benzenamine;

ethidimuron N-[5-(ethylsulfonyl)-1,3,4-thiadiazol-2-yl] -N,N'-dimethylurea;

ethiozin 4-amino-6-(1,1-dimethylethyl)-3-(ethylthio)-1,2,4-triazin-5(4H)-one;

ethofumesate 2-ethoxy-2,3-dihydro-3,3-dimethyl-5-benzofuranyl methanesulfonate;

F 5231 N-[2-chloro-4-fluoro-5-[4-(3-fluoropropyl)-4,5 -dihydro-5-oxo-1H-tetrazol-1-yl]phenyl]ethanesulfonamide;

fenoprop 2-(2,4,5-trichlorophenoxy)propanoic acid;

fenoxaprop-ethyl ethyl 2-[4-[(6 -chloro-2-benzoxazolyl)oxy]-phenoxy]propanoate;

fenuron N,N-dimethyl-N'-phenylurea;

flamprop-methyl methyl N-benzoyl-N-(3-chloro-4-fluorophenyl)-alaninate;

flazasulfuron 1-(4,6-dimethoxypyrimidin-2-yl)- 3-[3-(trifluoromethyl)-2-pyridylsulfonyl]urea;

fluazifop-butyl butyl 2-[4-[[5-(trifluoromethyl)-2 -pyridinyl] -oxy]phenoxy]propanoate;

fluchloralin N-(2-chloroethyl)-2,6-dinitro-N-propyl-4 -(trifluoromethyl)benzenamine;

flumeturon N,N-dimethyl-N'-[3-(trifluoromethyl)phenyl] -urea;

flumipropyn 2-[4-chloro-2-fluoro-5-[( 1-methyl-2-propynyl)oxy]phenyl-4,5,6,7-tetrahydro- 1H-isoindole-1,3(2H)dione;

fluorodifen 2-nitro-1-(4-nitrophenoxy)-4-(trifluoromethyl)benzene;

fluoroglycofen-ethyl ethyl carboxymethyl 5-[2-chloro-4 -(trifluoromethyl)phenoxy]-2-nitrobenzoate;

fluridone 1-methyl-3-phenyl-5-[ 3-(trifluoromethyl)phenyl] -4(1H)-pyridinone;

flurochloridone 3-chloro-4-(chloromethyl)- 1-[3-(trifluoromethyl)phenyl]-2-pyrrolidinone;

fluroxypyr 4-amino-3,5-dichloro-6-fluoro-2-pyridyloxyacetic acid;

flurtamone 5-(methylamino)-2-phenyl-4 -[3-(trifluoromethyl)phenyl]-3(2H)-furanone;

fomesafen 5-[2-chloro-4-(trifluoromethyl)phenoxy]-N-(methylsulfonyl)- 2-nitrobenzamide;

fosamine ethyl hydrogen carbamoylphosphonate;

furyloxyfen 3-[5-[2-chloro-4-(trifluoromethyl)phenoxy]-2 -nitrophenoxy]-tetrahydrofuran;

glufosinate 4-[hydroxy(methyl)phosphinoyl]homoalanine;

glyphosate N-(phosphonomethyl)glycine;

halosaten 5-[6-chloro- 2-fluoro-4-(trifluoromethyl)phenoxy]-N-(ethylsulfonyl)-2-nitrobenzamide;

haloxyfop 2-[4-[[3-chloro- 5-(trifluoromethyl)-2-pyridinyl] oxy]phenoxy]propanoic acid;

hexazinone 3-cyclohexyl-6-(dimethylamino)-1-methyl-1,3,5 -triazine-2,4(1H,3H)-dione;

Hw 52 N-(2,3-dichlorophenyl)-4-(ethoxymethoxy)benzamide;

imazamethabenz-methyl methyl 6-(4-isopropyl-4-methyl-5 -oxo-2-imidazolin-2-yl)-m-toluate and methyl 6-(4-isopropyl-4-methyl-5-oxo-2-imidazolin-2-yl)-p-toluate;

imazapyr 2-[4,5-dihydro-4-methyl-4-(1-methylethyl)-5-oxo-1H-imidazol-2-yl]-3-pyridinecarboxylic acid;

imazaquin 2-[4,5-dihydro-4-methyl-4-(1-methylethyl)-5 -oxo-1H-imidazol-2-yl]-3-quinolinecarboxylic acid;

imazethapyr 2-[4,5-dihydro-4-methyl-4-(1-methylethyl)-5 -oxo-1H-imidazol-2-yl]-5-ethyl-3-pyridinecarboxylic acid;

imazosulfuron 2-chloro-N-[[(4,6-dimethoxy- 2-pyrimidinyl)amino]carbonyl]imidazo[1,2-a]pyridine-3-sulfonamide;

ioxynil 4-hydroxy-3,5-diiodobenzonitrile;

isocarbamid N-(2-methylpropyl)-2-oxo-1-imidazolidinecarboxamide;

isopropalin 4-(1-methylethyl)-2,6-dinitro-N,N-dipropylbenzenamine;

isoproturon N-[4-(methylethyl)phenyl]-N',N'-dimethylurea;

isouron N'-[5-(1,1-dimethylethyl)-3-isoxazolyl]-N,N-dimethylurea;

isoxaben N-[3-(1-ethyl-1-methylpropyl)-5-isoxazolyl]-2,6 -dimethoxybenzamide;

isoxapyrifop 2-[2-[4-[(3,5-dichloro-2-pyridinyl)oxy] -phenoxy]-1-oxopropyl]-isoxazolidine;

karbutilate 3-[[(dimethylamino)carbonyl]amino]phenyl (1,1-dimethylethyl)carbamate;

lactofen 2-ethoxy-1-methyl-2-oxoethyl 5-[2-chloro-4 -(trifluoromethyl)phenoxy]-2-nitrobenzoate;

lenacil 3-cyclohexyl-6,7-dihydro-1H-cyclopentapyrimidine-2,4(3H,5H)-dione;

linuron N'-(3,4-dichlorophenyl)-N-methoxy-N-methylurea;

MCPA (4-chloro-2-methylphenoxy)acetic acid;

MCPB 4-(4-chloro-2-methylphenoxy)butanoic acid;

mecoprop 2-(4-chloro-4-methylphenoxy)propanoic acid;

mefenacet 2-benzothiazol-2-yloxy-N-methylacetanilide;

mefluidide N-[2,4-dimethyl-5 -[[(trifluoromethyl)sulfonyl] amino]phenyl]acetamide;

metamitron 4-amino-3-methyl-6-phenyl-1,2,4-triazin-5(4H)one;

metazachlor 2-chloro-N-(2,6 -dimethylphenyl)-N-(1(H)-pyrazol-1-ylmethyl)acetamide;

methabenzthiazuron 1,3-dimethyl-3-(2-benzothiazolyl)urea;

metham methylcarbamodithioic acid;

methazole 2-(3,4-dichlorophenyl)-4-methyl- 1,2,4-oxadiazolidine-3,5-dione;

methoxyphenone (4-methoxy-3-methylphenyl)(3-methylphenyl)methanone;

methyldymron N-methyl-N'-(1-methyl-1-phenylethyl)-N-phenylurea;

metobromuron N'-(4-bromophenyl)-N-methoxy-N-methylurea;

metolachlor 2-chloro-N-(2-ethyl-6-methylphenyl)-N-(2 -methoxy-1-methylethyl)acetamide;

metoxuron N'-(3-chloro-4-methoxyphenyl)-N,N-dimethylurea;
metribuzin 4-amino-6-(1,1-dimethylethyl)-3-(methylthio)-1,2,4-triazin-5(4H)-one;
metsulfuron-methyl methyl 2-[[[[(4-methoxy-6-methyl-1,3,5-triazin-2-yl)amino]carbonyl]amino]sulfonyl]-benzoate;
MH 1,2-dihydro-3,6-pyridazinedione;
molinate S-ethyl hexahydro-1H-azepine-1-carbothioate;
monalide N-(4-chlorophenyl)-2,2-dimethylpentanamide;
monolinuron 3-(4-chlorophenyl)-1-methoxy-1-methylurea;
monuron N'-(4-chlorophenyl)-N,N-dimethylurea;
MT 128 6-chloro-N-(3-chloro-2-propenyl)- 5-methyl-N-phenyl-3-pyridazinamine;
MT 5950 N-[3-chloro-4-(1-methylethyl)phenyl]-2-methylpentanamide;
naproanilide 2-(2-naphthalenyloxy)-N-phenylpropanamide;
napropamide N,N-diethyl-2-(1-naphthalenyloxy)propanamide;
naptalam 2-[(1-naphthalenylamino)carbonyl]benzoic acid;
NC 310 4-(2,4-dichlorobenzoyl)-1-methyl-5-benzyloxypyrazole;
neburon 1-butyl-3-(3,4-dichlorophenyl)-1-methylurea;
nicosulfuron 2-[[[[(4,6-dimethoxy- 2-pyrimidinyl)amino]carbonyl]amino]sulfonyl] -N,N-dimethyl-3-pyridinecarboxamide;
nipyraclophen 5-amino-1-(2,6 -dichloro-4-(trifluoromethyl)phenyl)-4-nitropyrazole;
nitralin 4-(methylsulfonyl)-2,6-dinitro-N,N-dipropylaniline;
nitrofen 2,4-dichloro-1-(4-nitrophenoxy)benzene;
nitrofluorfen 2-chloro-1-(4-nitrophenoxy)-4-(trifluoromethyl)benzene;
norflurazon 4-chloro-5-(methylamino)- 2-[3-(trifluoromethyl)phenyl]-3(2H)-pyridazinone;
orbencarb S-[2-(chlorophenyl)methyl]diethylcarbamothioate;
oryzalin 4-(dipropylamino)-3,5-dinitrobenzenesulfonamide;
oxadiazon 3-[2,4-dichloro-5-(1-methylethoxy)phenyl]-5-(1,1-dimethylethyl)-1,3, 4-oxadiazol-2(3H)-one;
oxyfluorfen 2-chloro-1-(3-ethoxy-4-nitrophenoxy)-4 -(trifluoromethyl)benzene;
paraquat 1,1'-dimethyl-4,4'-dipyridinium ion;
pebulate S-propyl butylethylcarbamothioate;
pendimethalin N-(1-ethylpropyl)-3,4-dimethyl-2,6-dinitrobenzenamine;
perfluidone 1,1-trifluoro-N-[2-methyl- 4-(phenylsulfonyl)phenyl]methanesulfonamide;
phenisopham 3-[[(1-methylethoxy)carbonyl]amino]phenyl ethylphenylcarbamate;
phenmedipham3-[(methoxycarbonyl)amino]phenyl (3-methylphenyl)carbamate;
piclorem 4-amino-3,5,6-trichloro-2-pyridinecarboxylic acid;
piperophos S-[2-(2-methyl-1-piperidinyl)-2-oxoethyl] O,O-dipropyl phosphorodithioate;
pirifenop-butyl butyl 2-[4-[( 3,5-dichloro-2-pyridinyl)oxy]phenoxy]propanoate;
PPG-1013 methyl 5-[2-chloro-4-(trifluoromethyl)phenoxy]-2-nitroacetophenone oxime O-acetate;
pretilachlor 2-chloro-N-(2,6-diethylphenyl)-N-(2-propoxyethyl)acetamide;
primisulfuron-methyl methyl 2-[[[[[ 4,6-bis(difluoromethoxy)pyrimidin-2-yl]amino] carbonyl]amino]sulfonyl]-benzoate;
procyazine 2-[[4-chloro-6 -(cyclopropylamino)-1,3,5-triazine-2-yl]amino]-2-methylpropanenitrile;
prodiamine 2,4-dinitro-$N^3$ $N^3$-dipropyl-6-(trifluoromethyl)-1,3-benzenediamine;
profluralin N-(cyclopropylmethyl)-2,6-dinitro-N-propyl-4-(trifluoromethyl)benzenamine;
proglinazine-ethyl ethyl N-[4-chloro-6-[ (1-methylethyl)amino]-1,3,5-triazin-2-yl]glycinate;
prometon 6-methoxy-N,N'-bis(1-methylethyl)- 1,3,5-triazine-2,4-diamine;
prometryn N,N'-bis(1-methylethyl)-6-(methylthio)-1,3,5-triazine-2,4-diamine;
propachlor 2-chloro-N-(1-methylethyl)-N-phenylacetamide;
propanil N-(3,4-dichlorophenyl)propanamide;
propaquizafop 2-[[(1-methylethylidene)amino]oxy]ethyl 2-[4-[(6-chloro-2-quinoxalinyl)oxy]phenoxy]propanoate;
propazine 6-chloro-N,N'-bis(1-methylethyl)-1,3,5-triazine2,4-diamine;
propham 1-methylethyl phenylcarbamate;
propyzamide 3,5-dichloro-N-(1,1-dimethyl-2-propynyl-)benzamide;
prosulfalin N-[[4-(dipropylamino)-3,5-dinitrophenyl] -sulfonyl]-S,S-dimethylsulfilimine;
prosulfocarb S-(phenyl)methyl dipropylcarbamothioate;
prynachlor 2-chloro-N-(1-methyl-2-propynyl)acetanilide;
pyrazolynate [4-(2,4-dichlorobenzoyl)- 1,3-dimethylpyrazol-5-yl]toluene-4-sulfonate;
pyrazon 5-amino-4-chloro-2-phenyl-3(2H)-pyridazinone;
pyrazosulfuron-ethyl 1-(4,6-dimethoxypyrimidin-2-yl)-3-[[(1-methyl)-4-(ethoxycarbonyl)pyrazol-5-yl]sulfonyl] urea;
pyrazoxyfen 2-[[4-(2,4-dichlorobenzoyl)-1,3-dimethyl-1H-pyrazol-5-yl]oxy]-1-phenylethanone;
pyributicarb O-[3-(1,1-dimethylethyl) phenyl](6 -methoxy-2-pyridinyl) methylcarbamothioate;
pyridate O-(6-chloro-3-phenyl-4-pyridazinyl) S-octyl carbonothioate;
quinclorac 3,7-dichloro-8-quinolinecarboxylic acid;
quinmerac 7-chloro-3-methyl-8-quinolinecarboxylic acid;
quizalofop-ethyl ethyl 2-[4-[(6 -chloro-2-quinoxalinyl)oxy]phenoxy]propanoate;
S 275 2-[4-chloro-2-fluoro-5-(2-propynyloxy) phenyl]-4,5,6,7-tetrahydro-2H-indazole;
S 482 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione;
secbumeton N-ethyl-6-methoxy-N'-(1 -methylpropyl)-1,3,5-triazine-2,4-diamine;
sethoxydim 2-[1-(ethoxyimino)butyl]-5-[ 2-(ethylthio)propyl]-3-hydroxy-2-cyclohexen-1-one;
siduron N-(2-methylcyclohexyl)-N'-phenylurea;
simazine 6-chloro-N,N'-diethyl-1,3,5-triazine-2,4-diamine;
simetryn N,N'-diethyl-6-(methylthio)-1,3,5-triazine-2,4-diamine;
SN 106279 methyl 2-[[7-[ 2-chloro-4-(trifluoromethyl)phenoxy]-2-naphthalenyl]oxy]propanoate;
sulfometuron-methyl methyl 2-[[[[ (4,6-dimethyl-2-pyrimidinyl)amino]carbonyl]amino]sulfonyl]benzoate;
TCA trichloroacetic acid;
tebutam2,2-dimethyl-N-(1-methylethyl)-N-(phenylmethyl-)propanamide;
tebuthiuron N-[5-(1,1-dimethylethyl)-1,3,4-thiadiazol-2 -yl]-N,N'-dimethylurea;
terbacil 5-chloro-3-(1,1-dimethylethyl)-6-methyl-2,4(1H,3H)-pyrimidinedione;
terbucarb 2,6-bis(1,1-dimethylethyl)-4-methylphenyl methylcarbamate,
terbuchlor N-(butoxymethyl)-2-chloro-N-[ 2-(1,1-dimethylethyl)-6-methylphenyl]acetamide;
terbumeton N-(1,1-dimethylethyl)-N'-ethyl-6-methoxy-1,3,5-triazine-2,4-diamine;

terbuthylazine 6-chloro-N-(1,1-dimethylethyl)-N'-ethyl-1,3,5-triazine-2,4-diamine;

terbutryn N-(1,1-dimethylethyl)-N'-ethyl-6-(methylthio)-1,3,5-triazine-2,4-diamine;

TFH 450 N,N-diethyl-3-[(2-ethyl- 6-methylphenyl)-sulfonyl]-1H-1,2,4-triazole-1-carboxamide;

thiazafluron N,N'-dimethyl-N-[5-(trifluoromethyl)-1,3,4-thiadiazol-2-yl]-urea;

thifensulfuron-methyl methyl 3-[[[[(4-methoxy-6-methyl-1,3,5-triazin-2-yl)amino]carbonyl]amino]sulfonyl] thiophenecarboxylate;

thiobencarb S-[(4-chlorophenyl)-methyl]-diethylcarbamothioate;

tiocarbazil S-(phenylmethyi)-bis(1-methylpropyl)carbamothioate;

tralkoxydim 2-[1-(ethoxyimino)propyl]- 5-[2,4,6-trimethylphenyl]-3-hydroxy-2-cyclohexen-1-one;

tri-allate S-(2,3,3-trichloro-2-propenyl) bis(1-methylethyl-)carbamothioate;

triasulfuron 1-(4-methoxy-6-methyl-1,3,5-triazin-2-yl)-3-[2-(2-chloroethoxy)phenylsulfonyl]urea;

triazofenamide 1-(3-methylphenyl)-5 -phenyl-1,2,4-triazole-2-carboxamide;

tribenuron-methyl methyl 2-[[[N-(4-methoxy-6-methyl-1,3,5-triazin-2-yl)-N-methylamino]carbonyl]amino]sulfonyl] benzoate;

triclopyr [(3,5,6-trichloro-2-pyridinyl)oxy]acetic acid;

tridiphane 2-(3,5-dichlorophenyl)-2-(2,2,2-trichloroethyl)oxirane;

trietazine 6-chloro-N,N,N'-triethyl-1,3,5-triazine-2,4-diamine;

trifluralin 2,6-dinitro-N,N-dipropyl-4-(trifluoromethyl)benzenamine;

trimeturon 1-(4-chlorophenyl)-2,3,3-trimethylpseudourea;

vernolate S-propyl dipropylcarbamothioate;

WL 110547 5-phenoxy-1-[3-(trifluoromethyl)phenyl]-1H-tetrazole.

The active substance content of the use forms of the active substances can vary within wide ranges, for example from 0.0001 to 100% by weight of active substance, preferably 0.001 to 99% by weight of active substance.

The agrochemical preparations (formulations) generally contain 0.1 to 99 percent by weight, in particular 0.1 to 95% by weight, of herbicidal active substance, and 1 to 99.9% by weight, preferably 5 to 99.9% by weight, of formulation auxiliaries which are inert under the storage and use conditions.

The preparations are applied in a customary manner which suits the use forms.

For example, the formulations, present in commercially available form, are diluted for use, if appropriate, in a conventional manner, for example using water in the case of wettable powders, emulsifiable concentrates, dispersions and water-dispersible granules. Preparations in the form of dusts and granules and also sprayable solutions are usually not further diluted with other inert substances before use.

The required application rate of the compounds of the formula (I) according to the invention varies with the external conditions such as, inter alia, temperature, humidity, and nature of the herbicide used. It can be varied within wide limits, for example between 0.001 and 10.0 kg/ha or more of active ingredient, but it is preferably between 0.005 and 5 kg/ha.

A. Chemical Examples

Example 1: N-tert. -butyl-(2-iodo-3-methoxycarbonyl)benzenesulfonamide

A solution of 24.1 g of tert.-butylamine in 30 ml of dichloromethane is added dropwise at room temperature to 59.3 g of 2-iodo-3-methoxycarbonylbenzenesulfochloride in 300 ml of dichloromethane. Stirring is continued for 3 hours at room temperature, the mixture is washed with 2N hydrochloric acid and dried over $Na_2SO_4$, and the solvent is evaporated. The residue is digested in ether. This gives 30.0 g of N-tert.-butyl-( 2-iodo-3-methoxycarbonyl)benzenesulfonamide in the form of colorless-crystals of m.p. 148°–9° C.

Example 2: 2-Iodo-3-methoxycarbonylbenzenesulfonamide 27.9 g of N-tert.-butyl-(2-iodo- 3-methoxycarbonyl)benzene-sulfonamide are stirred with 100 ml of trifluoroacetic acid for 4 hours at room temperature, the mixture is heated for 2 hours at the boil, and the organic phase is then evaporated in vacuo. The residue is taken up in dichloromethane/water, and sodium carbonate is added until the reaction is neutral. The phases are separated, and the aqueous phase is extracted two more times using dichloromethane. The combined organic phases are dried over $Na_2SO_4$, and the solvent is evaporated. After stirring of the residue with ether, 17.4 g of 2-iodo-3-methoxycarbonylbenzenesulfonamide of m.p. 155°–7° C. are obtained.

Example 3: Methyl 2-amino-4-iodobenzoate

A solution of 16.1 g of 2-acetylamino-4-iodobenzoic acid (m.p. 233°–5° C.; synthesized in accordance with U.S. Pat. No. 4,762,838) in 325 ml of absolute methanol is saturated at 0° C. with dry hydrogen chloride gas. The mixture is heated to the boil for 15 hours, cooled to room temperature, resaturated using dry hydrogen chloride gas, and allowed to stand at room temperature for 24 hours. The solvent is evaporated in vacuo, the residue is taken up in dichloromethane, and the organic phase is washed with a saturated aqueous sodium hydrogen carbonate solution until free from acid. The organic phase is dried over $Na_2SO_4$, and evaporated in vacuo. This gives 13.8 g of methyl 2-amino-4-iodobenzoate of m.p. 63°–7° C.

Example 4: Bis (2-methoxycarbonyl-5-iodobenzene)disulfide 13.8 g of methyl 2-amino-4-iodobenzoate are treated with 48 ml of glacial acetic acid and subsequently with 86 ml of concentrated hydrochloric acid. A solution of 3.8 g of sodium nitrite in 15 ml of water is slowly added dropwise to this suspension which is cooled to –5° C., and stirring is continued at this temperature for 30 minutes. This cooled diazonium salt solution is added dropwise at 0° C. to a solution of 20 ml of sulfur dioxide, 60 ml of glacial acetic acid, 10 ml of water and 3.1 g of copper(II) chloride dihydrate, and stirring is continued first for 1 hour at 0° C. and then overnight at room temperature. The reaction mixture is poured into 1 l of ice-water, and the product is filtered off with suction. This gives 12.7 g of bis( 2-methoxycarbonyl-5-iodobenzene)disulfide of m.p. 133°–5° C.

Example 5:
2-Methoxycarbonyl-5-iodobenzenesulfochloride

Chlorine gas is passed at 20°–25° C. into 12.2 g of bis(2-methoxycarbonyl-5-iodobenzene)disulfide in a solution of 30 ml of 1,2-dichloroethane and 15 ml of 2N hydrochloric acid until the exothermic reaction has ended. The solids are filtered off with suction, the aqueous phase is extracted using dichloromethane, the combined organic phases are dried over $Na_2SO_4$, and the solvent is evaporated in vacuo. This gives a total amount of 15.0 g of 2-methoxycarbonyl-5-iodobenzenesulfochloride, from the filtered and extracted product, of m.p. 119°–120° C. (decomposition).

Example 6:
2-Methoxycarbonyl-5-iodobenzenesulfonamide

Ammonia gas is passed at room temperature into 15.0 g of 2-methoxycarbonyl-5-iodobenzenesulfochloride in 100 ml of tetrahydrofuran until ammonia is no longer taken up. The solution is evaporated in vacuo, the residue is stirred thoroughly with water, and the product is filtered off with suction. After drying of the filter residue at 70° C. in vacuo, 10.7 g of 2 -methoxycarbonyl-5-iodobenzenesulfonamide are obtained as a white powder of m.p. 176°–7° C.

Example 7:

3-Ethoxycarbonyl- 2- iodobenzenesulfochloride 24.0 g of ethyl 3-amino-2-iodobenzoate are dissolved in 60 ml of glacial acetic acid and 120 ml of concentrated hydrochloric acid. A solution of 6.9 g of sodium nitrite in 30 ml of water is slowly added dropwise to this suspension which is cooled to –5° C. and stirring is continued at this temperature for 30 minutes. This cooled diazonium salt solution is added dropwise at 5°–10° C. to a solution of 70 ml of glacial acetic acid, 70 ml of concentrated hydrochloric acid and 3.0 g of copper(II) chloride dihydrate, which has been saturated with sulfur dioxide at approx. 10° C. The mixture is stirred for 3 hours at room temperature, and chlorine gas is then passed in until the exothermic reaction subsides. The reaction mixture is poured into 1 l of ice-water, and the product is filtered off with suction and dried in vacuo at 50° C. This gives 25.3 g of 3-ethoxycarbonyl-2-iodobenzenesulfo-chloride of m.p. 80°–3° C.

Example 8:
3-Ethoxycarbonyl-2-iodobenzenesulfonamide

Analogously to Example 6, 25.3 g of 3-ethoxycarbonyl-2 -iodobenzenesulfochloride and ammonia gave 20.4 g of 3-ethoxycarbonyl-2-iodobenzenesulfonamide of m.p. 138°–9° C.

Example 9: Methyl 2-[[[(4,6 -dimethoxy-2-pyrimidinyl)amino]carbonyl]amino]sulfonyl]-4-iodobenzoate A solution of 1.7 g of 1,8-diazabicyclo[5.4.0]undec-7-ene in 10 ml of absolute acetonitrile is added dropwise at room temperature to a mixture of 3.4 g of 5-iodo-2-methoxycarbonylbenzenesulfonamide and 2.8 g of O-phenyl (4,6-dimethoxy-2-pyrimidinyl)carbamate in 50 ml of absolute acetonitrile. The mixture is stirred at this temperature for 3 hours, concentrated to approx. ⅓ and poured into 200 ml of ice-water. The aqueous phase is extracted using diethyl ether, the pH is brought to 1–2 using concentrated hydrochloric acid, and the product is filtered off with suction. After drying in vacuo at 60° C., 3.3 g of methyl 2-[[[(4,6-dimethoxy- 2-pyrimidinyl)amino]carbonyl]amino]sulfonyl] -4-iodobenzoate of m.p. 169°–71° C. are obtained.

Example 10: Ethyl
2-iodo-3-[[[[(4-methoxy-6-methyl-1,3,5 -triazin-2-yl)amino]carbonyl]amino]sulfonyl]benzoate 14 mmol of trimethylaluminum (7 ml of a 2M solution in hexane) are added dropwise under a nitrogen protective atmosphere to a suspension of 3.6 g of 3-ethoxycarbonyl-2-iodobenzenesulfonamide in 100 ml of absolute dichloromethane. The mixture is stirred at room temperature for 30 minutes, and 2.2 g of O-methyl (4-methyl-6-methoxy-1,3,5-triazin-2-yl)carbamate in 25 ml of dichloromethane are then added, and the mixture is refluxed for 13 hours. The solution is cooled to room temperature, 25 ml of 2N hydrochloric acid are added dropwise with ice-cooling, and the hydrochloric acid phase is extracted twice using dichloromethane. The organic phase is concentrated in vacuo, and the residue is treated with acetone and 100 ml of 10% aqueous sodium acetate solution. The mixture is stirred for 3 hours and then filtered off with suction, followed by a washing step with diethyl ether, the aqueous phase is brought to pH 2–3 using concentrated hydrochloric acid and stirred for 15 minutes, and the product is filtered off with suction. After drying in vacuo at 50° C., 1.7 g of ethyl 2-iodo-3-[[[[(4-methoxy-6 -methyl-1,3,5-triazin-2-yl)amino]carbonyl]amino]sulfonyl] -benzoate of m.p. 177°–9° C. are obtained.

Example 11:
2-Methoxycarbonyl-5-iodobenzenesulfonyl isocyanate 50 g of the sulfonamide obtained in Example 6 are suspended in 150 ml of 1,2-dichloroethane and the suspension is treated with 27.7 ml of thionyl chloride. The mixture is heated at the boil for 4 hours, cooled to 50°–55° C. and treated with 0.5 ml of pyridine, and phosgene is passed for 3½ hours into the solution which has now been brought to the boil. The mixture is concentrated under reduced pressure with the exclusion of moisture. The crude sulfonyl isocyanate which remains (52.6 g) crystallises upon standing.

Example 12:
2-Iodo-3-methoxycarbonylbenzenesulfonyl isocyanate 27.3 g of 2-iodo-3-methoxycarbonylbenzenesulfonamide and 9.0 ml of n-butyl isocyanate in 300 ml of absolute acetone are treated with 12 ml of DBU at room temperature and heated at the boil for 3 hours. The reaction solution is cooled to room temperature, concentrated to approximately ⅓ of its volume and poured into 1 l of water. The aqueous phase is acidified with concentrated hydrochloric acid to a pH of 1–2, and the precipitate obtained is filtered off with suction. 31.3 g of methyl 2-iodo-[[[(n-butylamino)carbonyl] amino]sulfonyl]benzoate of melting point 163°–7° C. are obtained.

29.0 g of the resulting butylsulfonylurea are suspended in 400 ml of chlorobenzene and the suspension is brought to the boil. Phosgene is then passed in at boiling heat. The resulting butyl isocyanate is distilled off slowly in the course of 5 hours over a 20 cm Vigreux column in the form of a mixture with chlorobenzene. The mixture is concentrated in vacuo with the exclusion of moisture. This gives 28.4 g of 2-iodo-3-methoxycarbonylbenzenesulfonyl isocyanate in the form of an oil.

The sulfonamides of Tables 1a and 1b are obtained analogously to the processes of Examples 1 to 8.

The sulfonylureas of Tables 2–6 are obtained analogously to the processes of Examples 9 and 10. In the tables, the abbreviations refer to the general formula which precedes each table.

The sulfonyl isocyanates of Tables 1c and 1d are obtained analogously to the processes of Examples 11 and 12.

TABLE 1a

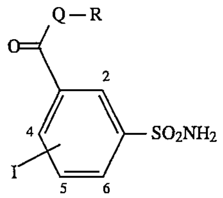

(IIa)

| IIa | Q | R | I | M.p. [°C.] |
|---|---|---|---|---|
| a | O | $CH_3$ | 2-I | 155–7 |
| b | O | $CH_2CH_3$ | 2-I | 138–9 |
| c | O | $CH_2CH_2CH_3$ | 2-I | 130–1 |
| d | O | $CH(CH_3)_2$ | 2-I | 133 |
| e | O | $CH_2CH_2CH_2CH_3$ | 2-I | |
| f | O | $CH_2CH(CH_3)_2$ | 2-I | |
| g | O | $CH(CH_3)CH_2CH_3$ | 2-I | |
| h | O | $C(CH_3)_3$ | 2-I | |
| i | O | $CH_2CH{=}CH_2$ | 2-I | |
| j | O | $CH_2C{\equiv}CH$ | 2-I | |
| k | O | $CH_2CH_2Cl$ | 2-I | |
| l | O | $CH_2CH_2OCH_3$ | 2-I | |
| m | O | c-$C_6H_{11}$ | 2-I | |
| n | O | $CH_3$ | 6-I | 161–2 |
| o | O | $CH_2CH_3$ | 6-I | |
| p | O | $CH_2CH_2CH_3$ | 6-I | |
| q | O | $CH(CH_3)_2$ | 6-I | |
| r | O | $CH_2CH_2CH_2CH_3$ | 6-I | |
| s | O | $CH_2CH(CH_3)_2$ | 6-I | |
| t | O | $CH(CH_3)CH_2CH_3$ | 6-I | |
| u | O | $C(CH_3)_3$ | 6-I | |
| v | O | $CH_2CH{=}CH_2$ | 6-I | |
| w | O | $CH_2C{\equiv}CH$ | 6-I | |
| x | O | $CH_2CH_2Cl$ | 6-I | |
| y | O | $CH_2CH_2OCH_3$ | 6-I | |
| z | O | c-$C_6H_{11}$ | 6-I | |

TABLE 1b

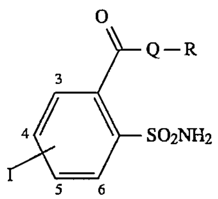

(IIb)

| IIb | Q | R | I | M.p. [°C.] |
|---|---|---|---|---|
| a | O | $CH_3$ | 3-I | 194–6 |
| b | O | $CH_2CH_3$ | 3-I | |
| c | O | $CH_2CH_2CH_3$ | 3-I | |
| d | O | $CH(CH_3)_2$ | 3-I | |
| e | O | $CH_2CH_2CH_2CH_3$ | 3-I | |
| f | O | $CH_2CH(CH_3)_2$ | 3-I | |
| g | O | $CH(CH_3)CH_2CH_3$ | 3-I | |
| h | O | $C(CH_3)_3$ | 3-I | |

TABLE 1b-continued

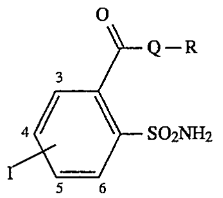

(IIb)

| IIb | Q | R | I | M.p. [°C.] |
|---|---|---|---|---|
| i | O | $CH_2CH{=}CH_2$ | 3-I | |
| j | O | $CH_2CH{\equiv}CH$ | 3-I | |
| k | O | $CH_2CH_2Cl$ | 3-I | |
| l | O | $CH_2CH_2OCH_3$ | 3-I | |
| m | O | c-$C_6H_{11}$ | 3-I | |
| n | O | $CH_3$ | 5-I | 181–182 |
| o | O | $CH_2CH_3$ | 5-I | 162 |
| p | O | $CH_2CH_2CH_3$ | 5-I | |
| q | O | $CH(CH_3)_2$ | 5-I | 139 |
| r | O | $CH_2CH_2CH_2CH_3$ | 5-I | |
| s | O | $CH_2CH(CH_3)_2$ | 5-I | |
| t | O | $CH(CH_3)CH_2CH_3$ | 5-I | |
| u | O | $C(CH_3)_3$ | 5-I | |
| v | O | $CH_2CH{=}CH_2$ | 5-I | |
| w | O | $CH_2CH{\equiv}CH$ | 5-I | |
| x | O | $CH_2CH_2Cl$ | 5-I | |
| y | O | $CH_2CH_2OCH_3$ | 5-I | |
| z | O | c-$C_6H_{11}$ | 5-I | |
| aa | O | $CH_3$ | 6-I | 213–5 |
| ab | O | $CH_2CH_3$ | 6-I | |
| ac | O | $CH_2CH_2CH_3$ | 6-I | |
| ad | O | $CH(CH_3)_2$ | 6-I | |
| ae | O | $CH_2CH_2CH_2CH_3$ | 6-I | |
| af | O | $CH_2CH(CH_3)_2$ | 6-I | |
| ag | O | $CH(CH_3)CH_2CH_3$ | 6-I | |
| ah | O | $C(CH_3)_3$ | 6-I | |
| ai | O | $CH_2CH{=}CH_2$ | 6-I | |
| aj | O | $CH_2CH{\equiv}CH$ | 6-I | |
| ak | O | $CH_2CH_2Cl$ | 6-I | |
| al | O | $CH_2CH_2OCH_3$ | 6-I | |
| am | O | c-$C_6H_{11}$ | 6-I | |

TABLE 1c

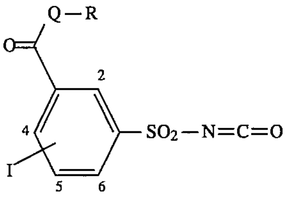

(VIa)

| (VIa) | Q | R | I | IR band [$cm^{-1}$] |
|---|---|---|---|---|
| a | O | $CH_3$ | 3-I | 2225 |
| b | O | $CH_2CH_3$ | 3-I | 2230 |
| c | O | $CH_2CH_2CH_3$ | 3-I | 2225 |
| d | O | $CH(CH_3)_2$ | 3-I | 2225 |
| e | O | $CH_2CH_2CH_2CH_3$ | 3-I | |
| f | O | $CH_2CH(CH_3)_2$ | 3-I | |
| g | O | $CH(CH_3)CH_2CH_3$ | 3-I | |
| h | O | $C(CH_3)_3$ | 3-I | |
| i | O | $CH_2CH{=}CH_2$ | 3-I | |
| j | O | $CH_2C{\equiv}CH$ | 3-I | |
| k | O | $CH_2CH_2Cl$ | 3-I | |
| l | O | $CH_2CH_2OCH_3$ | 3-I | |
| m | O | c-$C_6H_{11}$ | 3-I | |
| n | O | $CH_3$ | 5-I | 2225 |
| o | O | $CH_2CH_3$ | 5-I | |

TABLE 1c-continued

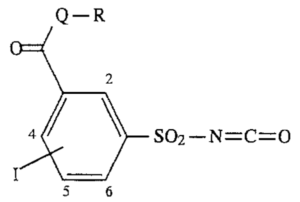

(VIa)

| (VIa) | Q | R | I | IR band [$cm^{-1}$] |
|---|---|---|---|---|
| p | O | $CH_2CH_2CH_3$ | 5-I | |
| q | O | $CH(CH_3)_2$ | 5-I | |
| r | O | $CH_2CH_2CH_2CH_3$ | 5-I | |
| s | O | $CH_2CH(CH_3)_2$ | 5-I | |
| t | O | $CH(CH_3)CH_2CH_3$ | 5-I | |
| u | O | $C(CH_3)_3$ | 5-I | |
| v | O | $CH_2CH{=}CH_2$ | 5-I | |
| w | O | $CH_2C{\equiv}CH$ | 5-I | |
| x | O | $CH_2CH_2Cl$ | 5-I | |
| y | O | $CH_2CH_2OCH_3$ | 5-I | |
| z | O | $c\text{-}C_6H_{11}$ | 5-I | |
| aa | O | $CH_3$ | 6-I | |
| ab | O | $CH_2CH_3$ | 6-I | |
| ac | O | $CH_2CH_2CH_3$ | 6-I | |
| ad | O | $CH(CH_3)_2$ | 6-I | |
| ae | O | $CH_2CH_2CH_2CH_3$ | 6-I | |
| af | O | $CH_2CH(CH_3)_2$ | 6-I | |
| ag | O | $CH(CH_3)CH_2CH_3$ | 6-I | |
| ah | O | $C(CH_3)_3$ | 6-I | |
| ai | O | $CH_2CH{=}CH_2$ | 6-I | |
| aj | O | $CH_2C{\equiv}CH$ | 6-I | |
| ak | O | $CH_2CH_2Cl$ | 6-I | |
| al | O | $CH_2CH_2OCH_3$ | 6-I | |
| am | O | $c\text{-}C_6H_{11}$ | 6-I | |

TABLE 1d

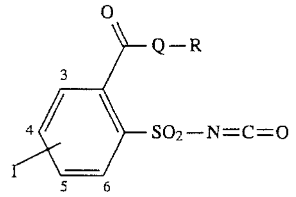

(VIb)

| (VIb) | Q | R | I | IR band [$cm^{-1}$] |
|---|---|---|---|---|
| a | O | $CH_3$ | 3-I | 2230 |

TABLE 1d-continued

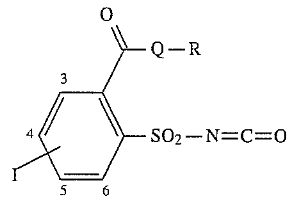

(VIb)

| (VIb) | Q | R | I | IR band [$cm^{-1}$] |
|---|---|---|---|---|
| b | O | $CH_2CH_3$ | 3-I | |
| c | O | $CH_2CH_2CH_3$ | 3-I | |
| d | O | $CH(CH_3)_2$ | 3-I | |
| e | O | $CH_2CH_2CH_2CH_3$ | 3-I | |
| f | O | $CH_2CH(CH_3)_2$ | 3-I | |
| g | O | $CH(CH_3)CH_2CH_3$ | 3-I | |
| h | O | $C(CH_3)_3$ | 3-I | |
| i | O | $CH_2CH{=}CH_2$ | 3-I | |
| j | O | $CH_2C{\equiv}CH$ | 3-I | |
| k | O | $CH_2CH_2Cl$ | 3-I | |
| l | O | $CH_2CH_2OCH_3$ | 3-I | |
| m | O | $c\text{-}C_6H_{11}$ | 3-I | |
| n | O | $CH_3$ | 5-I | 2230 |
| o | O | $CH_2CH_3$ | 5-I | 2225 |
| p | O | $CH_2CH_2CH_3$ | 5-I | |
| q | O | $CH(CH_3)_2$ | 5-I | 2225 |
| r | O | $CH_2CH_2CH_2CH_3$ | 5-I | |
| s | O | $CH_2CH(CH_3)_2$ | 5-I | |
| t | O | $CH(CH_3)CH_2CH_3$ | 5-I | |
| u | O | $C(CH_3)_3$ | 5-I | |
| v | O | $CH_2CH{=}CH_2$ | 5-I | |
| w | O | $CH_2C{\equiv}CH$ | 5-I | |
| x | O | $CH_2CH_2Cl$ | 5-I | |
| y | O | $CH_2CH_2OCH_3$ | 5-I | |
| z | O | $c\text{-}C_6H_{11}$ | 5-I | |
| aa | O | $CH_3$ | 6-I | 222-5 |
| ab | O | $CH_2CH_3$ | 6-I | |
| ac | O | $CH_2CH_2CH_3$ | 6-I | |
| ad | O | $CH(CH_3)_2$ | 6-I | |
| ae | O | $CH_2CH_2CH_2CH_3$ | 6-I | |
| af | O | $CH_2CH(CH_3)_2$ | 6-I | |
| ag | O | $CH(CH_3)CH_2CH_3$ | 6-I | |
| ah | O | $C(CH_3)_3$ | 6-I | |
| ai | O | $CH_2CH{=}CH_2$ | 6-I | |
| aj | O | $CH_2C{\equiv}CH$ | 6-I | |
| ak | O | $CH_2CH_2Cl$ | 6-I | |
| al | O | $CH_2CH_2OCH_3$ | 6-I | |
| am | O | $c\text{-}C_6H_{11}$ | 6-I | |

TABLE 2

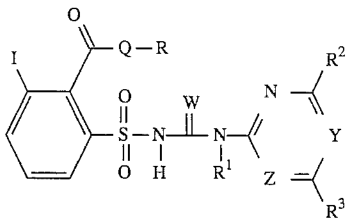

| Ex. No. | Q | R | $R^1$ | $R^2$ | $R^3$ | W | Y | Z | M.p. [°C.] |
|---|---|---|---|---|---|---|---|---|---|
| 1 | O | $CH_3$ | H | $OCH_3$ | $OCH_3$ | O | CH | N | 216–7 |
| 2 | O | $CH_3$ | $CH_3$ | $OCH_3$ | $OCH_3$ | O | CH | N | 181–2 |
| 3 | O | $CH_3$ | $CH_3$ | $OCH_3$ | $CH_3$ | O | N | N | 133–4 |
| 4 | O | $CH_3$ | H | $CH_3$ | $CH_3$ | O | CH | N | 210 |
| 5 | O | $CH_3$ | H | $OCH_3$ | $CH_3$ | O | CH | N | 201–2 |

TABLE 2-continued

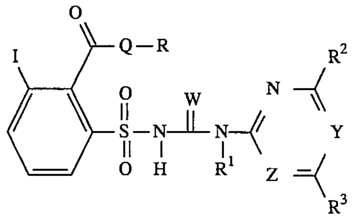

| Ex. No. | Q | R | $R^1$ | $R^2$ | $R^3$ | W | Y | Z | M.p. [°C.] |
|---|---|---|---|---|---|---|---|---|---|
| 6 | O | $CH_3$ | H | $CH_3$ | $CH_3$ | O | N | N | |
| 7 | O | $CH_3$ | H | $OCH_3$ | $CH_3$ | O | N | N | 196 decomp. |
| 8 | O | $CH_3$ | R | $OCH_3$ | $OCH_3$ | O | N | N | 205–6 |
| 9 | O | $CH_3$ | H | $OCH_3$ | Cl | O | CH | N | 218–21 |
| 10 | O | $CH_3$ | H | $OCF_2H$ | $CH_3$ | O | CH | N | |
| 11 | O | $CH_3$ | H | $OCF_2H$ | $OCF_2H$ | O | CH | N | 192–3 |
| 12 | O | $CH_3$ | H | $OCH_3$ | Br | O | CH | N | |
| 13 | O | $CH_3$ | H | $OCH_3$ | $OC_2H_5$ | O | CH | N | |
| 14 | O | $CH_3$ | H | $OCH_3$ | $SCH_3$ | O | CH | N | |
| 15 | O | $CH_3$ | H | $OCH_3$ | $OC_2H_5$ | O | N | N | |
| 16 | O | $CH_3$ | H | $OCH_3$ | $OC_3H_7$ | O | CH | N | |
| 17 | O | $CH_3$ | H | $OCH_3$ | Cl | O | N | N | |
| 18 | O | $CH_3$ | H | Cl | $OC_2H_5$ | O | CH | N | |
| 19 | O | $CH_3$ | H | $OC_2H_5$ | $OC_2H_5$ | O | CH | N | |
| 20 | O | $CH_3$ | H | $C_2H_5$ | $OCH_3$ | O | CH | N | |
| 21 | O | $CH_3$ | H | $CF_3$ | $OCH_3$ | O | CH | N | |
| 22 | O | $CH_3$ | H | $OCH_2CF_3$ | $CH_3$ | O | CH | N | |
| 23 | O | $CH_3$ | H | $OCH_2CF_3$ | $OCH_3$ | O | CH | N | |
| 24 | O | $CH_3$ | H | $OCH_2CF_3$ | $OCH_2CF_3$ | O | CH | N | |
| 25 | O | $CH_3$ | H | $OCH_2CF_3$ | $OCH_3$ | O | N | N | |
| 26 | O | $CH_3$ | H | $OCH_3$ | $NHCH_3$ | O | N | N | |
| 27 | O | $CH_3$ | H | $OC_2H_5$ | $NHCH_3$ | O | N | N | |
| 28 | O | $CH_3$ | H | $C_2H_5$ | $OC_2H_5$ | O | N | N | |
| 29 | O | $CH_3$ | H | $OCH_3$ | $CH_3$ | O | N | N | |
| 30 | O | $CH_3$ | H | Cl | $CH_3$ | O | N | N | |
| 31 | O | $CH_3$ | H | $CH_3$ | $CH_3$ | O | N | N | |
| 32 | O | $CH_3$ | H | $OCH_3$ | $OCH_3$ | S | CH | N | |
| 33 | O | $CH_3$ | H | $OCH_3$ | $CH_3$ | S | CH | N | |
| 34 | O | $CH_3$ | H | $CH_3$ | $CH_3$ | S | CH | N | |
| 35 | O | $CH_3$ | H | $OCH_3$ | $OCH_3$ | S | N | N | |
| 36 | O | $CH_3$ | R | $OCH_3$ | $CH_3$ | S | N | N | |
| 37 | O | $CH_3$ | H | $CH_3$ | $CH_3$ | S | N | N | |
| 38 | O | $C_2H_5$ | H | $OCH_3$ | $OCH_3$ | O | CH | N | |
| 39 | O | $C_2H_5$ | $CH_3$ | $OCH_3$ | $OCH_3$ | O | CH | N | |
| 40 | O | $C_2H_5$ | $CH_3$ | $OCH_3$ | $CH_3$ | O | N | N | |
| 41 | O | $C_2H_5$ | H | $CH_3$ | $CH_3$ | O | CH | N | |
| 42 | O | $C_2H_5$ | H | $OCH_3$ | $CH_3$ | O | CH | N | |
| 43 | O | $C_2H_5$ | H | $CH_3$ | $CH_3$ | O | N | N | |
| 44 | O | $C_2H_5$ | H | $OCH_3$ | $CH_3$ | O | N | N | |
| 45 | O | $C_2H_5$ | H | $OCH_3$ | $OCH_3$ | O | N | N | |
| 46 | O | $C_2H_5$ | H | $OCH_3$ | Cl | O | CH | N | |
| 47 | O | $C_2H_5$ | H | $OCF_2H$ | $CH_3$ | O | CH | N | |
| 48 | O | $C_2H_5$ | H | $OCF_2H$ | $OCF_2H$ | O | CH | N | |
| 49 | O | $C_2H_5$ | H | $OCH_3$ | Br | O | CH | N | |
| 50 | O | $C_2H_5$ | H | $OCH_3$ | $OC_2H_5$ | O | CH | N | |
| 51 | O | $C_2H_5$ | H | $OCH_3$ | $SCH_3$ | O | CH | N | |
| 52 | O | $C_2H_5$ | H | $OCH_3$ | $OC_2H_5$ | O | N | N | |
| 53 | O | $C_2H_5$ | H | $OCH_3$ | $OC_3H_7$ | O | CH | N | |
| 54 | O | $C_2H_5$ | H | $OCH_3$ | Cl | O | N | N | |
| 55 | O | $C_2H_5$ | H | Cl | $OC_2H_5$ | O | CH | N | |
| 56 | O | $C_2H_5$ | H | $OC_2H_5$ | $OC_2H_5$ | O | CH | N | |
| 57 | O | $C_2H_5$ | H | $C_2H_5$ | $OCH_3$ | O | CH | N | |
| 58 | O | $C_2H_5$ | H | $CF_3$ | $OCH_3$ | O | CH | N | |
| 59 | O | $C_2H_5$ | H | $OCH_2CF_3$ | $CH_3$ | O | CH | N | |
| 60 | O | $C_2H_5$ | H | $OCH_2CF_3$ | $OCH_3$ | O | CH | N | |
| 61 | O | $C_2H_5$ | H | $OCH_2CF_3$ | $OCH_2CF_3$ | O | CH | N | |
| 62 | O | $C_2H_5$ | H | $OCH_2CF_3$ | $OCH_3$ | O | N | N | |
| 63 | O | $C_2H_5$ | H | $OCH_3$ | $NHCH_3$ | O | N | N | |
| 64 | O | $C_2H_5$ | H | $OC_2H_5$ | $NHCH_3$ | O | N | N | |
| 65 | O | $C_2H_5$ | H | $C_2H_5$ | $OC_2H_5$ | O | N | N | |
| 66 | O | $C_2H_5$ | H | $OCH_3$ | $CH_3$ | O | N | N | |
| 67 | O | $C_2H_5$ | H | Cl | $CH_3$ | O | N | N | |
| 68 | O | $C_2H_5$ | H | $CH_3$ | $CH_3$ | O | N | N | |
| 69 | O | $C_2H_5$ | H | $OCH_3$ | $OCH_3$ | S | CH | N | |
| 70 | O | $C_2H_5$ | H | $OCH_3$ | $CH_3$ | S | CH | N | |

TABLE 2-continued

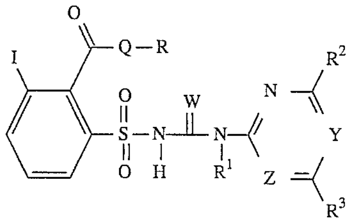

| Ex. No. | Q | R | $R^1$ | $R^2$ | $R^3$ | W | Y | Z | M.p. [°C.] |
|---|---|---|---|---|---|---|---|---|---|
| 71 | O | $C_2H_5$ | H | $CH_3$ | $CH_3$ | S | CH | N | |
| 72 | O | $C_2H_5$ | H | $OCH_3$ | $OCH_3$ | S | N | N | |
| 73 | O | $C_2H_5$ | H | $OCH_3$ | $CH_3$ | S | N | N | |
| 74 | O | $C_2H_5$ | H | $CH_3$ | $CH_3$ | S | N | N | |
| 75 | O | n-$C_3H_7$ | H | $OCH_3$ | $OCH_3$ | O | CH | N | |
| 76 | O | n-$C_3H_7$ | $CH_3$ | $OCH_3$ | $OCH_3$ | O | CH | N | |
| 77 | O | n-$C_3H_7$ | $CH_3$ | $OCH_3$ | $CH_3$ | O | N | N | |
| 78 | O | n-$C_3H_7$ | H | $CH_3$ | $CH_3$ | O | CH | N | |
| 79 | O | n-$C_3H_7$ | H | $OCH_3$ | $CH_3$ | O | CH | N | |
| 80 | O | n-$C_3H_7$ | H | $CH_3$ | $CH_3$ | O | N | N | |
| 81 | O | n-$C_3H_7$ | H | $OCH_3$ | $CH_3$ | O | N | N | |
| 82 | O | n-$C_3H_7$ | H | $OCH_3$ | $OCH_3$ | O | N | N | |
| 83 | O | n-$C_3H_7$ | H | $OCH_3$ | Cl | O | CH | N | |
| 84 | O | n-$C_3H_7$ | H | $OCF_2H$ | $CH_3$ | O | CH | N | |
| 85 | O | n-$C_3H_7$ | H | $OCF_2H$ | $OCF_2H$ | O | CH | N | |
| 86 | O | n-$C_3H_7$ | H | $OCH_3$ | Br | O | CH | N | |
| 87 | O | n-$C_3H_7$ | H | $OCH_3$ | $OC_2H_5$ | O | CH | N | |
| 88 | O | n-$C_3H_7$ | H | $OCH_3$ | $SCH_3$ | O | CH | N | |
| 89 | O | n-$C_3H_7$ | H | $OCH_3$ | $OC_2H_5$ | O | N | N | |
| 90 | O | n-$C_3H_7$ | H | $OCH_3$ | $OC_3H_7$ | O | CH | N | |
| 91 | O | n-$C_3H_7$ | H | $OCH_3$ | Cl | O | N | N | |
| 92 | O | n-$C_3H_7$ | H | Cl | $OC_2H_5$ | O | CH | N | |
| 93 | O | n-$C_3H_7$ | H | $OC_2H_5$ | $OC_2H_5$ | O | CH | N | |
| 94 | O | n-$C_3H_7$ | H | $C_2H_5$ | $OCH_3$ | O | CH | N | |
| 95 | O | n-$C_3H_7$ | H | $CF_3$ | $OCH_3$ | O | CH | N | |
| 96 | O | n-$C_3H_7$ | H | $OCH_2CF_3$ | $CH_3$ | O | CH | N | |
| 97 | O | n-$C_3H_7$ | H | $OCH_2CF_3$ | $OCH_3$ | O | CH | N | |
| 98 | O | n-$C_3H_7$ | H | $OCH_2CF_3$ | $OCH_2CF_3$ | O | CH | N | |
| 99 | O | n-$C_3H_7$ | H | $OCH_2CF_3$ | $OCH_3$ | O | N | N | |
| 100 | O | n-$C_3H_7$ | H | $OCH_3$ | $NHCH_3$ | O | N | N | |
| 101 | O | n-$C_3H_7$ | H | $OC_2H_5$ | $NHCH_3$ | O | N | N | |
| 102 | O | n-$C_3H_7$ | H | $C_2H_5$ | $OC_2H_5$ | O | N | N | |
| 103 | O | n-$C_3H_7$ | H | $OCH_3$ | $CH_3$ | O | N | N | |
| 104 | O | n-$C_3H_7$ | H | Cl | $CH_3$ | O | N | N | |
| 105 | O | n-$C_3H_7$ | H | $CH_3$ | $CH_3$ | O | N | N | |
| 106 | O | n-$C_3H_7$ | H | $OCH_3$ | $OCH_3$ | S | CH | N | |
| 107 | O | n-$C_3H_7$ | H | $OCH_3$ | $CH_3$ | S | CH | N | |
| 108 | O | n-$C_3H_7$ | H | $CH_3$ | $CH_3$ | S | CH | N | |
| 109 | O | n-$C_3H_7$ | H | $OCH_3$ | $OCH_3$ | S | N | N | |
| 110 | O | n-$C_3H_7$ | H | $OCH_3$ | $CH_3$ | S | N | N | |
| 111 | O | n-$C_3H_7$ | H | $CH_3$ | $CH_3$ | S | N | N | |
| 112 | O | i-$C_3H_7$ | H | $OCH_3$ | $OCH_3$ | O | CH | N | |
| 113 | O | i-$C_3H_7$ | $CH_3$ | $OCH_3$ | $OCH_3$ | O | CH | N | |
| 114 | O | i-$C_3H_7$ | $CH_3$ | $OCH_3$ | $CH_3$ | O | N | N | |
| 115 | O | i-$C_3H_7$ | H | $CH_3$ | $CH_3$ | O | CH | N | |
| 116 | O | i-$C_3H_7$ | H | $OCH_3$ | $CH_3$ | O | CH | N | |
| 117 | O | i-$C_3H_7$ | H | $CH_3$ | $CH_3$ | O | N | N | |
| 118 | O | i-$C_3H_7$ | H | $OCH_3$ | $CH_3$ | O | N | N | |
| 119 | O | i-$C_3H_7$ | H | $OCH_3$ | $OCH_3$ | O | N | N | |
| 120 | O | i-$C_3H_7$ | H | $OCH_3$ | Cl | O | CH | N | |
| 121 | O | i-$C_3H_7$ | H | $OCF_2H$ | $CH_3$ | O | CH | N | |
| 122 | O | i-$C_3H_7$ | H | $OCF_2H$ | $OCF_2H$ | O | CH | N | |
| 123 | O | i-$C_3H_7$ | H | $OCH_3$ | Br | O | CH | N | |
| 124 | O | i-$C_3H_7$ | H | $OCH_3$ | $OC_2H_5$ | O | CH | N | |
| 125 | O | i-$C_3H_7$ | H | $OCH_3$ | $SCH_3$ | O | CH | N | |
| 126 | O | i-$C_3H_7$ | H | $OCH_3$ | $OC_2H_5$ | O | N | N | |
| 127 | O | i-$C_3H_7$ | H | $OCH_3$ | $OC_3H_7$ | O | CH | N | |
| 128 | O | i-$C_3H_7$ | H | $OCH_3$ | Cl | O | N | N | |
| 129 | O | i-$C_3H_7$ | H | Cl | $OC_2H_5$ | O | CH | N | |
| 130 | O | i-$C_3H_7$ | H | $OC_2H_5$ | $OC_2H_5$ | O | CH | N | |
| 131 | O | i-$C_3H_7$ | H | $C_2H_5$ | $OCH_3$ | O | CH | N | |
| 132 | O | i-$C_3H_7$ | H | $CF_3$ | $OCH_3$ | O | CH | N | |
| 133 | O | i-$C_3H_7$ | H | $OCH_2CF_3$ | $CH_3$ | O | CH | N | |
| 134 | O | i-$C_3H_7$ | H | $OCH_2CF_3$ | $OCH_3$ | O | CH | N | |
| 135 | O | i-$C_3H_7$ | H | $OCH_2CF_3$ | $OCH_2CF_3$ | O | CH | N | |

TABLE 2-continued

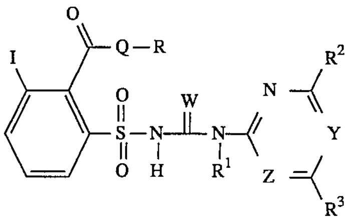

| Ex. No. | Q | R | $R^1$ | $R^2$ | $R^3$ | W | Y | Z | M.p. [°C.] |
|---|---|---|---|---|---|---|---|---|---|
| 136 | O | i-$C_3H_7$ | H | $OCH_2CF_3$ | $OCH_3$ | O | N | N | |
| 137 | O | i-$C_3H_7$ | H | $OCH_3$ | $NHCH_3$ | O | N | N | |
| 138 | O | i-$C_3H_7$ | H | $OC_2H_5$ | $NHCH_3$ | O | N | N | |
| 139 | O | i-$C_3H_7$ | H | $C_2H_5$ | $OC_2H_5$ | O | N | N | |
| 140 | O | i-$C_3H_7$ | H | $OCH_3$ | $CH_3$ | O | N | N | |
| 141 | O | i-$C_3H_7$ | H | Cl | $CH_3$ | O | N | N | |
| 142 | O | i-$C_3H_7$ | H | $CH_3$ | $CH_3$ | O | N | N | |
| 143 | O | i-$C_3H_7$ | H | $OCH_3$ | $OCH_3$ | S | CH | N | |
| 144 | O | i-$C_3H_7$ | H | $OCH_3$ | $CH_3$ | S | CH | N | |
| 145 | O | i-$C_3H_7$ | H | $CH_3$ | $CH_3$ | S | CH | N | |
| 146 | O | i-$C_3H_7$ | H | $OCH_3$ | $OCH_3$ | S | N | N | |
| 147 | O | i-$C_3H_7$ | H | $OCH_3$ | $CH_3$ | S | N | N | |
| 148 | O | i-$C_3H_7$ | H | $CH_3$ | $CH_3$ | S | N | N | |
| 149 | O | $CH_2CH{=}CH_2$ | H | $OCH_3$ | $OCH_3$ | O | CH | N | |
| 150 | O | $CH_2CH{=}CH_2$ | $CH_3$ | $OCH_3$ | $OCH_3$ | O | CH | N | |
| 151 | O | $CH_2CH{=}CH_2$ | $CH_3$ | $OCH_3$ | $CH_3$ | O | N | N | |
| 152 | O | $CH_2CH{=}CH_2$ | H | $CH_3$ | $CH_3$ | O | CH | N | |
| 153 | O | $CH_2CH{=}CH_2$ | H | $OCH_3$ | $CH_3$ | O | CH | N | |
| 154 | O | $CH_2CH{=}CH_2$ | H | $CH_3$ | $CH_3$ | O | N | N | |
| 155 | O | $CH_2CH{=}CH_2$ | H | $OCH_3$ | $CH_3$ | O | N | N | |
| 156 | O | $CH_2CH{=}CH_2$ | H | $OCH_3$ | $OCH_3$ | O | N | N | |
| 157 | O | $CH_2CH{=}CH_2$ | H | $OCH_3$ | Cl | O | CH | N | |
| 158 | O | $CH_2CH{=}CH_2$ | H | $OCF_2H$ | $CH_3$ | O | CH | N | |
| 159 | O | $CH_2CH{=}CH_2$ | H | $OCF_2H$ | $OCF_2H$ | O | CH | N | |
| 160 | O | $CH_2CH{=}CH_2$ | H | $OCH_3$ | Br | O | CH | N | |
| 161 | O | $CH_2CH{=}CH_2$ | H | $OCH_3$ | $OC_2H_5$ | O | CH | N | |
| 162 | O | $CH_2CH{=}CH_2$ | H | $OCH_3$ | $SCH_3$ | O | CH | N | |
| 163 | O | $CH_2CH{=}CH_2$ | H | $OCH_3$ | $OC_2H_5$ | O | N | N | |
| 164 | O | $CH_2CH{=}CH_2$ | H | $OCH_3$ | $OC_3H_7$ | O | CH | N | |
| 165 | O | $CH_2CH{=}CH_2$ | H | $OCH_3$ | Cl | O | N | N | |
| 166 | O | $CH_2CH{=}CH_2$ | H | Cl | $OC_2H_5$ | O | CH | N | |
| 167 | O | $CH_2CH{=}CH_2$ | H | $OC_2H_5$ | $OC_2H_5$ | O | CH | N | |
| 168 | O | $CH_2CH{=}CH_2$ | H | $C_2H_5$ | $OCH_3$ | O | CH | N | |
| 169 | O | $CH_2CH{=}CH_2$ | H | $CF_3$ | $OCH_3$ | O | CH | N | |
| 170 | O | $CH_2CH{=}CH_2$ | H | $OCH_2CF_3$ | $CH_3$ | O | CH | N | |
| 171 | O | $CH_2CH{=}CH_2$ | H | $OCH_2CF_3$ | $OCH_3$ | O | CH | N | |
| 172 | O | $CH_2CH{=}CH_2$ | H | $OCH_2CF_3$ | $OCH_2CF_3$ | O | CH | N | |
| 173 | O | $CH_2CH{=}CH_2$ | R | $OCH_2CF_3$ | $OCH_3$ | O | N | N | |
| 174 | O | $CH_2CH{=}CH_2$ | H | $OCH_3$ | $NHCH_3$ | O | N | N | |
| 175 | O | $CH_2CH{=}CH_2$ | H | $OC_2H_5$ | $NHCH_3$ | O | N | N | |
| 176 | O | $CH_2CH{=}CH_2$ | H | $C_2H_5$ | $OC_2H_5$ | O | N | N | |
| 177 | O | $CH_2CH{=}CH_2$ | H | $OCH_3$ | $CH_3$ | O | N | N | |
| 178 | O | $CH_2CH{=}CH_2$ | H | Cl | $CH_3$ | O | N | N | |
| 179 | O | $CH_2CH{=}CH_2$ | H | $CH_3$ | $CH_3$ | O | N | N | |
| 180 | O | $CH_2CH{=}CH_2$ | H | $OCH_3$ | $OCH_3$ | S | CH | N | |
| 181 | O | $CH_2CH{=}CH_2$ | H | $OCH_3$ | $CH_3$ | S | CH | N | |
| 182 | O | $CH_2CH{=}CH_2$ | H | $CH_3$ | $CH_3$ | S | N | N | |
| 184 | O | $CH_2CH{=}CH_2$ | H | $OCH_3$ | $OCH_3$ | S | N | N | |
| 185 | O | $CH_2CH{=}CH_2$ | H | $OCH_3$ | $CH_3$ | S | N | N | |
| 186 | O | $CH_2C{\equiv}CH$ | H | $OCH_3$ | $OCH_3$ | O | CH | N | |
| 187 | O | $CH_2C{\equiv}CH$ | $CH_3$ | $OCH_3$ | $OCH_3$ | O | CH | N | |
| 188 | O | $CH_2C{\equiv}CH$ | $CH_3$ | $OCH_3$ | $CH_3$ | O | N | N | |
| 189 | O | $CH_2C{\equiv}CH$ | H | $CH_3$ | $CH_3$ | O | CH | N | |
| 190 | O | $CH_2C{\equiv}CH$ | H | $OCH_3$ | $CH_3$ | O | CH | N | |
| 191 | O | $CH_2C{\equiv}CH$ | H | $CH_3$ | $CH_3$ | O | N | N | |
| 192 | O | $CH_2C{\equiv}CH$ | H | $OCH_3$ | $CH_3$ | O | N | N | |
| 193 | O | $CH_2C{\equiv}CH$ | H | $OCH_3$ | $OCH_3$ | O | N | N | |

TABLE 2-continued

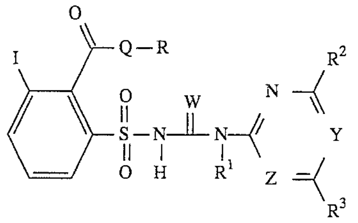

| Ex. No. | Q | R | $R^1$ | $R^2$ | $R^3$ | W | Y | Z | M.p. [°C.] |
|---|---|---|---|---|---|---|---|---|---|
| 194 | O | $CH_2C{\equiv}CH$ | H | $OCH_3$ | Cl | O | CH | N | |
| 195 | O | $CH_2C{\equiv}CH$ | H | $OCF_2H$ | $CH_3$ | O | CH | N | |
| 196 | O | $CH_2C{\equiv}CH$ | H | $OCF_2H$ | $OCF_2H$ | O | CH | N | |
| 197 | O | $CH_2C{\equiv}CH$ | H | $OCH_3$ | Br | O | CH | N | |
| 198 | O | $CH_2C{\equiv}CH$ | H | $OCH_3$ | $OC_2H_5$ | O | CH | N | |
| 199 | O | $CH_2C{\equiv}CH$ | H | $OCH_3$ | $SCH_3$ | O | CH | N | |
| 200 | O | $CH_2C{\equiv}CH$ | H | $OCH_3$ | $OC_2H_5$ | O | N | N | |
| 201 | O | $CH_2C{\equiv}CH$ | H | $OCH_3$ | $OC_3H_7$ | O | CH | N | |
| 202 | O | $CH_2C{\equiv}CH$ | H | $OCH_3$ | Cl | O | N | N | |
| 203 | O | $CH_2C{\equiv}CH$ | H | Cl | $OC_2H_5$ | O | CH | N | |
| 204 | O | $CH_2C{\equiv}CH$ | H | $OC_2H_5$ | $OC_2H_5$ | O | CH | N | |
| 205 | O | $CH_2C{\equiv}CH$ | H | $C_2H_5$ | $OCH_3$ | O | CH | N | |
| 206 | O | $CH_2C{\equiv}CH$ | H | $CF_3$ | $OCH_3$ | O | CH | N | |
| 207 | O | $CH_2C{\equiv}CH$ | H | $OCH_2CF_3$ | $CH_3$ | O | CH | N | |
| 208 | O | $CH_2C{\equiv}CH$ | H | $OCH_2CF_3$ | $OCH_3$ | O | CH | N | |
| 209 | O | $CH_2C{\equiv}CH$ | H | $OCH_2CF_3$ | $OCH_2CF_3$ | O | CH | N | |
| 210 | O | $CH_2C{\equiv}CH$ | H | $OCH_2CF_3$ | $OCH_3$ | O | N | N | |
| 211 | O | $CH_2C{\equiv}CH$ | H | $OCH_3$ | $NHCH_3$ | O | N | N | |
| 212 | O | $CH_2C{\equiv}CH$ | H | $OC_2H_5$ | $NHCH_3$ | O | N | N | |
| 213 | O | $CH_2C{\equiv}CH$ | H | $C_2H_5$ | $OC_2H_5$ | O | N | N | |
| 214 | O | $CH_2C{\equiv}CH$ | H | $OCH_3$ | $CH_3$ | O | N | N | |
| 215 | O | $CH_2C{\equiv}CH$ | H | Cl | $CH_3$ | O | N | N | |
| 216 | O | $CH_2C{\equiv}CH$ | H | $CH_3$ | $CH_3$ | O | N | N | |
| 217 | O | $CH_2C{\equiv}CH$ | H | $OCH_3$ | $OCH_3$ | S | CH | N | |
| 218 | O | $CH_2C{\equiv}CH$ | H | $OCH_3$ | $CH_3$ | S | CH | N | |
| 219 | O | $CH_2C{\equiv}CH$ | H | $CH_3$ | $CH_3$ | S | CH | N | |
| 220 | O | $CH_2C{\equiv}CH$ | H | $OCH_3$ | $OCH_3$ | S | N | N | |
| 221 | O | $CH_2C{\equiv}CH$ | H | $OCH_3$ | $CH_3$ | S | N | N | |
| 222 | O | $CH_2C{\equiv}CH$ | H | $CH_3$ | $CH_3$ | S | N | N | |
| 223 | O | n-$C_4H_9$ | H | $OCH_3$ | $OCH_3$ | O | CH | N | |
| 224 | O | n-$C_4H_9$ | $CH_3$ | $OCH_3$ | $OCH_3$ | O | CH | N | |
| 225 | O | n-$C_4H_9$ | $CH_3$ | $OCH_3$ | $CH_3$ | O | N | N | |
| 226 | O | n-$C_4H_9$ | H | $CH_3$ | $CH_3$ | O | CH | N | |
| 227 | O | n-$C_4H_9$ | H | $OCH_3$ | $CH_3$ | O | CH | N | |
| 228 | O | n-$C_4H_9$ | H | $CH_3$ | $CH_3$ | O | N | N | |
| 229 | O | n-$C_4H_9$ | H | $OCH_3$ | $CH_3$ | O | N | N | |
| 230 | O | n-$C_4H_9$ | H | $OCH_3$ | $OCH_3$ | O | N | N | |
| 231 | O | i-$C_4H_9$ | H | $OCH_3$ | $OCH_3$ | O | CH | N | |
| 232 | O | i-$C_4H_9$ | $CH_3$ | $OCH_3$ | $OCH_3$ | O | CH | N | |
| 233 | O | i-$C_4H_9$ | $CH_3$ | $OCH_3$ | $CH_3$ | O | N | N | |
| 234 | O | i-$C_4H_9$ | H | $CH_3$ | $CH_3$ | O | CH | N | |

TABLE 2-continued

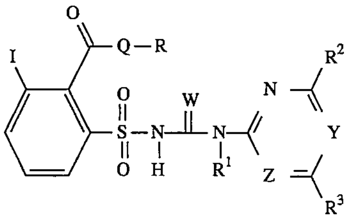

| Ex. No. | Q | R | $R^1$ | $R^2$ | $R^3$ | W | Y | Z | M.p. [°C.] |
|---|---|---|---|---|---|---|---|---|---|
| 235 | O | $i\text{-}C_4H_9$ | H | $OCH_3$ | $CH_3$ | O | CH | N | |
| 236 | O | $i\text{-}C_4H_9$ | H | $CH_3$ | $CH_3$ | O | N | N | |
| 237 | O | $i\text{-}C_4H_9$ | H | $OCH_3$ | $CH_3$ | O | N | N | |
| 238 | O | $i\text{-}C_4H_9$ | H | $OCH_3$ | $OCH_3$ | O | N | N | |
| 239 | O | sec.-$C_4H_9$ | H | $OCH_3$ | $OCH_3$ | O | CH | N | |
| 240 | O | sec.-$C_4H_9$ | $CH_3$ | $OCH_3$ | $OCH_3$ | O | CH | N | |
| 241 | O | sec.-$C_4H_9$ | $CH_3$ | $OCH_3$ | $CH_3$ | O | N | N | |
| 242 | O | sec.-$C_4H_9$ | H | $CH_3$ | $CH_3$ | O | CH | N | |
| 243 | O | Sec.-$C_4H_9$ | H | $OCH_3$ | $CH_3$ | O | CH | N | |
| 244 | O | sec.-$C_4H_9$ | H | $CH_3$ | $CH_3$ | O | N | N | |
| 245 | O | sec.-$C_4H_9$ | H | $OCH_3$ | $CH_3$ | O | N | N | |
| 246 | O | sec.-$C_4H_9$ | H | $OCH_3$ | $OCH_3$ | O | N | N | |
| 247 | O | $t\text{-}C_4H_9$ | H | $OCH_3$ | $OCH_3$ | O | CH | N | |
| 248 | O | $t\text{-}C_4H_9$ | $CH_3$ | $OCH_3$ | $OCH_3$ | O | CH | N | |
| 249 | O | $t\text{-}C_4H_9$ | $CH_3$ | $OCH_3$ | $CH_3$ | O | N | N | |
| 250 | O | $t\text{-}C_4H_9$ | H | $CH_3$ | $CH_3$ | O | CH | N | |
| 251 | O | $t\text{-}C_4H_9$ | H | $OCH_3$ | $CH_3$ | O | CH | N | |
| 252 | O | $t\text{-}C_4H_9$ | H | $CH_3$ | $CH_3$ | O | N | N | |
| 253 | O | $t\text{-}C_4H_9$ | H | $OCH_3$ | $CH_3$ | O | N | N | |
| 254 | O | $t\text{-}C_4H_9$ | H | $OCH_3$ | $OCH_3$ | O | N | N | |
| 255 | O | $CH_2CH_2Cl$ | H | $OCH_3$ | $OCH_3$ | O | CH | N | |
| 256 | O | $CH_2CH_2Cl$ | $CH_3$ | $OCH_3$ | $OCH_3$ | O | CH | N | |
| 257 | O | $CH_2CH_2Cl$ | $CH_3$ | $OCH_3$ | $CH_3$ | O | N | N | |
| 258 | O | $CH_2CH_2Cl$ | H | $CH_3$ | $CH_3$ | O | CH | N | |
| 259 | O | $CH_2CH_2Cl$ | H | $OCH_3$ | $CH_3$ | O | CH | N | |
| 260 | O | $CH_2CH_2Cl$ | H | $CH_3$ | $CH_3$ | O | N | N | |
| 261 | O | $CH_2CH_2Cl$ | H | $OCH_3$ | $CH_3$ | O | N | N | |
| 262 | O | $CH_2CH_2Cl$ | H | $OCH_3$ | $OCH_3$ | O | N | N | |
| 263 | O | $CH_2CH_2OCH_3$ | H | $OCH_3$ | $OCH_3$ | O | CH | N | |
| 264 | O | $CH_2CH_2OCH_3$ | $CH_3$ | $OCH_3$ | $OCH_3$ | O | CH | N | |
| 265 | O | $CH_2CH_2OCH_3$ | $CH_3$ | $OCH_3$ | $CH_3$ | O | N | N | |
| 266 | O | $CH_2CH_2OCH_3$ | H | $CH_3$ | $CH_3$ | O | CH | N | |
| 267 | O | $CH_2CH_2OCH_3$ | H | $OCH_3$ | $CH_3$ | O | CH | N | |
| 268 | O | $C_2CH_2OCH_3$ | H | $CH_3$ | $CH_3$ | O | N | N | |
| 269 | O | $CH_2CH_2OCH_3$ | H | $OCH_3$ | $CH_3$ | O | N | N | |
| 270 | O | $CH_2CH_2OCH_3$ | H | $OCH_3$ | $OCH_3$ | O | N | N | |
| 271 | O | $c\text{-}C_6H_{11}$ | H | $OCH_3$ | $OCH_3$ | O | CH | N | |
| 272 | O | $c\text{-}C_6H_{11}$ | $CH_3$ | $OCH_3$ | $OCH_3$ | O | CH | N | |
| 273 | O | $c\text{-}C_6H_{11}$ | $CH_3$ | $OCH_3$ | $CH_3$ | O | N | N | |
| 274 | O | $c\text{-}C_6H_{11}$ | H | $CH_3$ | $CH_3$ | O | CH | N | |
| 275 | O | $c\text{-}C_6H_{11}$ | H | $OCH_3$ | $CH_3$ | O | CH | N | |
| 276 | O | $c\text{-}C_6H_{11}$ | H | $CH_3$ | $CH_3$ | O | N | N | |
| 277 | O | $c\text{-}C_6H_{11}$ | H | $OCH_3$ | $CH_3$ | O | N | N | |
| 278 | O | $c\text{-}C_6H_{11}$ | H | $OCH_3$ | $OCH_3$ | O | N | N | |
| 279 | O | $CH_3$ | H | $OCH_3$ | $SCH_3$ | O | CH | N | 211-3 decomp. |
| 280 | O | $CH_3$ | H | $CH_3$ | $SCH_3$ | O | N | N | 196-8 |
| 281 | O | $CH_3$ | H | $c\text{-}C_3H_5$ | $OCH_3$ | O | N | N | 175-8 |
| 282 | O | $CH_3$ | H | $C_2H_5$ | $OCH_3$ | O | N | N | 195-6 |
| 283 | O | $CH_3$ | H | $CH_2SCH_3$ | $OCH_3$ | O | N | N | 147-50 |
| 284 | O | $CH_3$ | $CH_3$ | $OCH_3$ | $OCH_3$ | O | N | N | 131-3 |
| 285 | O | $CH_3$ | H | $OCH_3$ | $OCH_3$ | O | CH | N | Na-salt 189 |
| 286 | O | $CH_3$ | H | $OCH_3$ | $CH_3$ | O | N | N | Na-salt 195 |
| 287 | O | $CH_3$ | H | $OCH_3$ | $CH_3$ | O | CH | N | Na-salt 189 |
| 288 | O | $CH_3$ | H | $c\text{-}C_3H_5$ | $CH_3$ | O | N | N | Na-salt 170 |
| 289 | O | $CH_3$ | $CH_3$ | $OCH_3$ | $OCH_3$ | O | N | N | Na-salt 130 |
| 290 | O | $CH_3$ | H | $C_2H_5$ | $OCH_3$ | O | N | N | Na-salt 172 |
| 291 | O | $CH_3$ | $CH_3$ | $OCH_3$ | $OC_2H_5$ | O | N | N | Li-salt 124 |
| 292 | O | $CH_3$ | H | $OCH_3$ | $CH_3$ | O | CH | N | Na-salt |

TABLE 2-continued

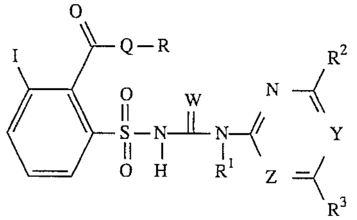

| Ex. No. | Q | R | $R^1$ | $R^2$ | $R^3$ | W | Y | Z | M.p. [°C.] |
|---|---|---|---|---|---|---|---|---|---|
| 293 | O | $CH_3$ | $CH_3$ | $OCH_3$ | $OCH_3$ | O | CH | N | 191<br>Na-salt<br>118 |
| 294 | O | $CH_3$ | $CH_3$ | $OCH_3$ | $CH_3$ | O | N | N | Na-salt<br>138 |
| 295 | O | $CH_3$ | H | $OCH_3$ | $OCH_3$ | O | N | N | Na-salt<br>184 |

TABLE 3

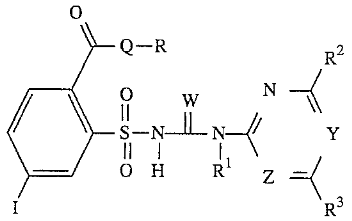

| Ex. No. | Q | R | $R^1$ | $R^2$ | $R^3$ | W | Y | Z | M.p. [°C.] |
|---|---|---|---|---|---|---|---|---|---|
| 1 | O | $CH_3$ | H | $OCH_3$ | $OCH_3$ | O | CH | N | 169–71 |
| 2 | O | $CH_3$ | $CH_3$ | $OCH_3$ | $OCH_3$ | O | CH | N | 186–7 |
| 3 | O | $CH_3$ | $CH_3$ | $OCH_3$ | $CH_3$ | O | N | N | 172–3 |
| 4 | O | $CH_3$ | H | $CH_3$ | $CH_3$ | O | CH | N | 195–6 |
| 5 | O | $CH_3$ | H | $OCH_3$ | $CH_3$ | O | CH | N | 177 |
| 6 | O | $CH_3$ | H | $CH_3$ | $CH_3$ | O | N | N | 182–4 |
| 7 | O | $CH_3$ | H | $OCH_3$ | $CH_3$ | O | N | N | 158–63 |
| 8 | O | $CH_3$ | H | $OCH_3$ | $OCH_3$ | O | N | N | 174 |
| 9 | O | $CH_3$ | H | $OCH_3$ | Cl | O | CH | N | 170–2 |
| 10 | O | $CH_3$ | H | $OCF_2H$ | $CH_3$ | O | CH | N | |
| 11 | O | $CH_3$ | H | $OCF_2H$ | $OCF_2H$ | O | CH | N | 178–9 |
| 12 | O | $CH_3$ | H | $OCH_3$ | Br | O | CH | N | |
| 13 | O | $CH_3$ | H | $OCH_3$ | $OC_2H_5$ | O | CH | N | |
| 14 | O | $CH_3$ | H | $OCH_3$ | $SCH_3$ | O | CH | N | |
| 15 | O | $CH_3$ | H | $OCH_3$ | $OC_2H_5$ | O | N | N | |
| 16 | O | $CH_3$ | H | $OCH_3$ | $OC_3H_7$ | O | CH | N | |
| 17 | O | $CH_3$ | H | $OCH_3$ | Cl | O | N | N | |
| 18 | O | $CH_3$ | H | Cl | $OC_2H_5$ | O | CH | N | |
| 19 | O | $CH_3$ | H | $OC_2H_5$ | $OC_2H_5$ | O | CH | N | |
| 20 | O | $CH_3$ | H | $C_2H_5$ | $OCH_3$ | O | CH | N | |
| 21 | O | $CH_3$ | H | $CF_3$ | $OCH_3$ | O | CH | N | |
| 22 | O | $CH_3$ | H | $OCH_2CF_3$ | $CH_3$ | O | CH | N | |
| 23 | O | $CH_3$ | H | $OCH_2CF_3$ | $OCH_3$ | O | CH | N | |
| 24 | O | $CH_3$ | H | $OCH_2CF_3$ | $OCH_2CF_3$ | O | CH | N | |
| 25 | O | $CH_3$ | H | $OCH_2CF_3$ | $OCH_3$ | O | N | N | 125 decomp. |
| 26 | O | $CH_3$ | H | $OCH_3$ | $NHCH_3$ | O | N | N | |
| 27 | O | $CH_3$ | H | $OC_2H_5$ | $NHCH_3$ | O | N | N | |
| 28 | O | $CH_3$ | H | $C_2H_5$ | $OC_2H_5$ | O | N | N | |
| 29 | O | $CH_3$ | H | $OCH_3$ | $CH_3$ | O | N | N | |
| 30 | O | $CH_3$ | H | Cl | $CH_3$ | O | N | N | |
| 31 | O | $CH_3$ | H | $CH_3$ | $CH_3$ | O | N | N | |
| 32 | O | $CH_3$ | H | $OCH_3$ | $OCH_3$ | S | CH | N | |
| 33 | O | $CH_3$ | H | $OCH_3$ | $CH_3$ | S | CH | N | |
| 34 | O | $CH_3$ | H | $CH_3$ | $CH_3$ | S | CH | N | |
| 35 | O | $CH_3$ | H | $OCH_3$ | $OCH_3$ | S | N | N | |
| 36 | O | $CH_3$ | H | $OCH_3$ | $CH_3$ | S | N | N | |
| 37 | O | $CH_3$ | H | $CH_3$ | $CH_3$ | S | N | N | |
| 38 | O | $C_2H_5$ | H | $OCH_3$ | $OCH_3$ | O | CH | N | 174–7 |
| 39 | O | $C_2H_5$ | $CH_3$ | $OCH_3$ | $OCH_3$ | O | CH | N | 155–7 |

TABLE 3-continued

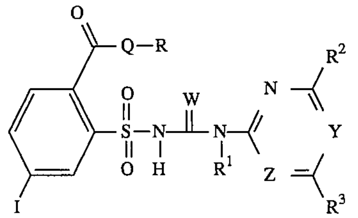

| Ex. No. | Q | R | $R^1$ | $R^2$ | $R^3$ | W | Y | Z | M.p. [°C.] |
|---|---|---|---|---|---|---|---|---|---|
| 40 | O | $C_2H_5$ | $CH_3$ | $OCH_3$ | $CH_3$ | O | N | N | 163–4 |
| 41 | O | $C_2H_5$ | H | $CH_3$ | $CH_3$ | O | CH | N | |
| 42 | O | $C_2H_5$ | H | $OCH_3$ | $CH_3$ | O | CH | N | 183–4 |
| 43 | O | $C_2H_5$ | H | $CH_3$ | $CH_3$ | O | N | N | |
| 44 | O | $C_2H_5$ | H | $OCH_3$ | $CH_3$ | O | N | N | 168–70 |
| 45 | O | $C_2H_5$ | H | $OCH_3$ | $OCH_3$ | O | N | N | 154–8 |
| 46 | O | $C_2H_5$ | H | $OCH_3$ | Cl | O | CH | N | 151–3 |
| 47 | O | $C_2H_5$ | H | $OCF_2H$ | $CH_3$ | O | CH | N | |
| 48 | O | $C_2H_5$ | H | $OCF_2H$ | $OCF_2H$ | O | CH | N | |
| 49 | O | $C_2H_5$ | H | $OCH_3$ | Br | O | CH | N | |
| 50 | O | $C_2H_5$ | H | $OCH_3$ | $OC_2H_5$ | O | CH | N | |
| 51 | O | $C_2H_5$ | H | $OCH_3$ | $SCH_3$ | O | CH | N | |
| 52 | O | $C_2H_5$ | H | $OCH_3$ | $OC_2H_5$ | O | N | N | |
| 53 | O | $C_2H_5$ | H | $OCH_3$ | $OC_3H_7$ | O | CH | N | |
| 54 | O | $C_2H_5$ | H | $OCH_3$ | Cl | O | N | N | |
| 55 | O | $C_2H_5$ | H | Cl | $OC_2H_5$ | O | CH | N | |
| 56 | O | $C_2H_5$ | H | $OC_2H_5$ | $OC_2H_5$ | O | CH | N | |
| 57 | O | $C_2H_5$ | H | $C_2H_5$ | $OCH_3$ | O | CH | N | |
| 58 | O | $C_2H_5$ | H | $CF_3$ | $OCH_3$ | O | CH | N | |
| 59 | O | $C_2H_5$ | H | $OCH_2CF_3$ | $CH_3$ | O | CH | N | |
| 60 | O | $C_2H_5$ | H | $OCH_2CF_3$ | $OCH_3$ | O | CH | N | |
| 61 | O | $C_2H_5$ | H | $OCH_2CF_3$ | $OCH_2CF_3$ | O | CH | N | |
| 62 | O | $C_2H_5$ | H | $OCH_2CF_3$ | $OCH_3$ | O | N | N | |
| 63 | O | $C_2H_5$ | H | $OCH_3$ | $NHCH_3$ | O | N | N | |
| 64 | O | $C_2H_5$ | H | $OC_2H_5$ | $NHCH_3$ | O | N | N | |
| 65 | O | $C_2H_5$ | H | $C_2H_5$ | $OC_2H_5$ | O | N | N | |
| 66 | O | $C_2H_5$ | H | $OCH_3$ | $CH_3$ | O | N | N | |
| 67 | O | $C_2H_5$ | H | Cl | $CH_3$ | O | N | N | |
| 68 | O | $C_2H_5$ | H | $CH_3$ | $CH_3$ | O | N | N | |
| 69 | O | $C_2H_5$ | H | $OCH_3$ | $OCH_3$ | S | CH | N | |
| 70 | O | $C_2H_5$ | H | $OCH_3$ | $CH_3$ | S | CH | N | |
| 71 | O | $C_2H_5$ | H | $CH_3$ | $CH_3$ | S | CH | N | |
| 72 | O | $C_2H_5$ | H | $OCH_3$ | $OCH_3$ | S | N | N | |
| 73 | O | $C_2H_5$ | H | $OCH_3$ | $CH_3$ | S | N | N | |
| 74 | O | $C_2H_5$ | H | $CH_3$ | $CH_3$ | S | N | N | |
| 75 | O | $n-C_3H_7$ | H | $OCH_3$ | $OCH_3$ | O | CH | N | |
| 76 | O | $n-C_3H_7$ | $CH_3$ | $OCH_3$ | $OCH_3$ | O | CH | N | |
| 77 | O | $n-C_3H_7$ | $CH_3$ | $OCH_3$ | $CH_3$ | O | N | N | |
| 78 | O | $n-C_3H_7$ | H | $CH_3$ | $CH_3$ | O | CH | N | |
| 79 | O | $n-C_3H_7$ | H | $OCH_3$ | $CH_3$ | O | CH | N | |
| 80 | O | $n-C_3H_7$ | H | $CH_3$ | $CH_3$ | O | N | N | |
| 81 | O | $n-C_3H_7$ | H | $OCH_3$ | $CH_3$ | O | N | N | |
| 82 | O | $n-C_3H_7$ | H | $OCH_3$ | $OCH_3$ | O | N | N | |
| 83 | O | $n-C_3H_7$ | H | $OCH_3$ | Cl | O | CH | N | |
| 84 | O | $n-C_3H_7$ | H | $OCF_2H$ | $CH_3$ | O | CH | N | |
| 85 | O | $n-C_3H_7$ | H | $OCF_2H$ | $OCF_2H$ | O | CH | N | |
| 86 | O | $n-C_3H_7$ | H | $OCH_3$ | Br | O | CH | N | |
| 87 | O | $n-C_3H_7$ | H | $OCH_3$ | $OC_2H_5$ | O | CH | N | |
| 88 | O | $n-C_3H_7$ | H | $OCH_3$ | $SCH_3$ | O | CH | N | |
| 89 | O | $n-C_3H_7$ | H | $OCH_3$ | $OC_2H_5$ | O | N | N | |
| 90 | O | $n-C_3H_7$ | H | $OCH_3$ | $OC_3H_7$ | O | CH | N | |
| 91 | O | $n-C_3H_7$ | H | $OCH_3$ | Cl | O | N | N | |
| 92 | O | $n-C_3H_7$ | H | Cl | $OC_2H_5$ | O | CH | N | |
| 93 | O | $n-C_3H_7$ | H | $OC_2H_5$ | $OC_2H_5$ | O | CH | N | |
| 94 | O | $n-C_3H_7$ | H | $C_2H_5$ | $OCH_3$ | O | CH | N | |
| 95 | O | $n-C_3H_7$ | H | $CF_3$ | $OCH_3$ | O | CH | N | |
| 96 | O | $n-C_3H_7$ | H | $OCH_2CF_3$ | $CH_3$ | O | CH | N | |
| 97 | O | $n-C_3H_7$ | H | $OCH_2CF_3$ | $OCH_3$ | O | CH | N | |
| 98 | O | $n-C_3H_7$ | H | $OCH_2CF_3$ | $OCH_2CF_3$ | O | CH | N | |
| 99 | O | $n-C_3H_7$ | H | $OCH_2CF_3$ | $OCH_3$ | O | N | N | |
| 100 | O | $n-C_3H_7$ | H | $OCH_3$ | $NHCH_3$ | O | N | N | |
| 101 | O | $n-C_3H_7$ | H | $OC_2H_5$ | $NHCH_3$ | O | N | N | |
| 102 | O | $n-C_3H_7$ | H | $C_2H_5$ | $OC_2H_5$ | O | N | N | |
| 103 | O | $n-C_3H_7$ | H | $OCH_3$ | $CH_3$ | O | N | N | |
| 104 | O | $n-C_3H_7$ | H | Cl | $CH_3$ | O | N | N | |

TABLE 3-continued

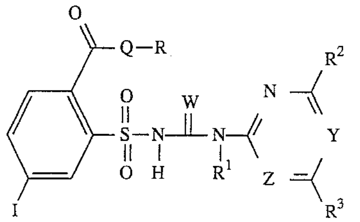

| Ex. No. | Q | R | $R^1$ | $R^2$ | $R^3$ | W | Y | Z | M.p. [°C.] |
|---|---|---|---|---|---|---|---|---|---|
| 105 | O | n-$C_3H_7$ | H | $CH_3$ | $CH_3$ | O | N | N | |
| 106 | O | n-$C_3H_7$ | H | $OCH_3$ | $OCH_3$ | S | CH | N | |
| 107 | O | n-$C_3H_7$ | H | $OCH_3$ | $CH_3$ | S | CH | N | |
| 108 | O | n-$C_3H_7$ | H | $CH_3$ | $CH_3$ | S | CH | N | |
| 109 | O | n-$C_3H_7$ | H | $OCH_3$ | $OCH_3$ | S | N | N | |
| 110 | O | n-$C_3H_7$ | H | $OCH_3$ | $CH_3$ | S | N | N | |
| 111 | O | n-$C_3H_7$ | H | $CH_3$ | $CH_3$ | S | N | N | |
| 112 | O | i-$C_3H_7$ | H | $OCH_3$ | $OCH_3$ | O | CH | N | 190-1 |
| 113 | O | i-$C_3H_7$ | $CH_3$ | $OCH_3$ | $OCH_3$ | O | CH | N | |
| 114 | O | i-$C_3H_7$ | $CH_3$ | $OCH_3$ | $CH_3$ | O | N | N | |
| 115 | O | i-$C_3H_7$ | H | $CH_3$ | $CH_3$ | O | CH | N | |
| 116 | O | i-$C_3H_7$ | H | $OCH_3$ | $CH_3$ | O | CH | N | |
| 117 | O | i-$C_3H_7$ | H | $CH_3$ | $CH_3$ | O | N | N | |
| 118 | O | i-$C_3H_7$ | H | $OCH_3$ | $CH_3$ | O | N | N | |
| 119 | O | i-$C_3H_7$ | H | $OCH_3$ | $OCH_3$ | O | N | N | |
| 120 | O | i-$C_3H_7$ | H | $OCH_3$ | Cl | O | CH | N | |
| 121 | O | i-$C_3H_7$ | H | $OCF_2H$ | $CH_3$ | O | CH | N | |
| 122 | O | i-$C_3H_7$ | H | $OCF_2H$ | $OCF_2H$ | O | CH | N | |
| 123 | O | i-$C_3H_7$ | H | $OCH_3$ | Br | O | CH | N | |
| 124 | O | i-$C_3H_7$ | H | $OCH_3$ | $OC_2H_5$ | O | CH | N | |
| 125 | O | i-$C_3H_7$ | H | $OCH_3$ | $SCH_3$ | O | CH | N | |
| 126 | O | i-$C_3H_7$ | H | $OCH_3$ | $OC_2H_5$ | O | N | N | |
| 127 | O | i-$C_3H_7$ | H | $OCH_3$ | $OC_3H_7$ | O | CH | N | |
| 128 | O | i-$C_3H_7$ | H | $OCH_3$ | Cl | O | N | N | |
| 129 | O | i-$C_3H_7$ | H | Cl | $OC_2H_5$ | O | CH | N | |
| 130 | O | i-$C_3H_7$ | H | $OC_2H_5$ | $OC_2H_5$ | O | CH | N | |
| 131 | O | i-$C_3H_7$ | H | $C_2H_5$ | $OCH_3$ | O | CH | N | |
| 132 | O | i-$C_3H_7$ | H | $CF_3$ | $OCH_3$ | O | CH | N | |
| 133 | O | i-$C_3H_7$ | H | $OCH_2CF_3$ | $CH_3$ | O | CH | N | |
| 134 | O | i-$C_3H_7$ | H | $OCH_2CF_3$ | $OCH_3$ | O | CH | N | |
| 135 | O | i-$C_3H_7$ | H | $OCH_2CF_3$ | $OCH_2CF_3$ | O | CH | N | |
| 136 | O | i-$C_3H_7$ | H | $OCH_2CF_3$ | $OCH_3$ | O | N | N | |
| 137 | O | i-$C_3H_7$ | H | $OCH_3$ | $NHCH_3$ | O | N | N | |
| 138 | O | i-$C_3H_7$ | H | $OC_2H_5$ | $NHCH_3$ | O | N | N | |
| 139 | O | i-$C_3H_7$ | H | $C_2H_5$ | $OC_2H_5$ | O | N | N | |
| 140 | O | i-$C_3H_7$ | H | $OCH_3$ | $CH_3$ | O | N | N | |
| 141 | O | i-$C_3H_7$ | H | Cl | $CH_3$ | O | N | N | |
| 142 | O | i-$C_3H_7$ | H | $CH_3$ | $CH_3$ | O | N | N | |
| 143 | O | i-$C_3H_7$ | H | $OCH_3$ | $OCH_3$ | S | CH | N | |
| 144 | O | i-$C_3H_7$ | H | $OCH_3$ | $CH_3$ | S | CH | N | |
| 145 | O | i-$C_3H_7$ | H | $CH_3$ | $CH_3$ | S | CH | N | |
| 146 | O | i-$C_3H_7$ | H | $OCH_3$ | $OCH_3$ | S | N | N | |
| 147 | O | i-$C_3H_7$ | H | $OCH_3$ | $CH_3$ | S | N | N | |
| 148 | O | i-$C_3H_7$ | H | $CH_3$ | $CH_3$ | S | N | N | |
| 149 | O | $CH_2CH{=}CH_2$ | H | $OCH_3$ | $OCH_3$ | O | CH | N | |
| 150 | O | $CH_2CH{=}CH_2$ | $CH_3$ | $OCH_3$ | $OCH_3$ | O | CH | N | |
| 151 | O | $CH_2CH{=}CH_2$ | $CH_3$ | $OCH_3$ | $CH_3$ | O | N | N | |
| 152 | O | $CH_2CH{=}CH_2$ | H | $CH_3$ | $CH_3$ | O | CH | N | |
| 153 | O | $CH_2CH{=}CH_2$ | H | $OCH_3$ | $CH_3$ | O | CH | N | |
| 154 | O | $CH_2CH{=}CH_2$ | H | $CH_3$ | $CH_3$ | O | N | N | |
| 155 | O | $CH_2CH{=}CH_2$ | H | $OCH_3$ | $CH_3$ | O | N | N | |
| 156 | O | $CH_2CH{=}CH_2$ | H | $OCH_3$ | $OCH_3$ | O | N | N | |
| 157 | O | $CH_2CH{=}CH_2$ | H | $OCH_3$ | Cl | O | CH | N | |
| 158 | O | $CH_2CH{=}CH_2$ | H | $OCF_2H$ | $CH_3$ | O | CH | N | |
| 159 | O | $CH_2CH{=}CH_2$ | H | $OCF_2H$ | $OCF_2H$ | O | CH | N | |
| 160 | O | $CH_2CH{=}CH_2$ | H | $OCH_3$ | Br | O | CH | N | |
| 161 | O | $CH_2CH{=}CH_2$ | H | $OCH_3$ | $OC_2H_5$ | O | CH | N | |
| 162 | O | $CH_2CH{=}CH_2$ | H | $OCH_3$ | $SCH_3$ | O | CH | N | |
| 163 | O | $CH_2CH{=}CH_2$ | H | $OCH_3$ | $OC_2H_5$ | O | N | N | |
| 164 | O | $CH_2CH{=}CH_2$ | H | $OCH_3$ | $OC_3H_7$ | O | CH | N | |
| 165 | O | $CH_2CH{=}CH_2$ | H | $OCH_3$ | Cl | O | N | N | |
| 166 | O | $CH_2CH{=}CH_2$ | H | Cl | $OC_2H_5$ | O | CH | N | |
| 167 | O | $CH_2CH{=}CH_2$ | H | $OC_2H_5$ | $OC_2H_5$ | O | CH | N | |
| 168 | O | $CH_2CH{=}CH_2$ | H | $C_2H_5$ | $OCH_3$ | O | CH | N | |
| 169 | O | $CH_2CH{=}CH_2$ | H | $CF_3$ | $OCH_3$ | O | CH | N | |

TABLE 3-continued

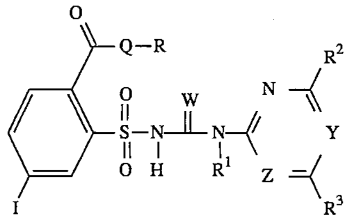

| Ex. No. | Q | R | $R^1$ | $R^2$ | $R^3$ | W | Y | Z | M.p. [°C.] |
|---|---|---|---|---|---|---|---|---|---|
| 170 | O | $CH_2CH{=}CH_2$ | H | $OCH_2CF_3$ | $CH_3$ | O | CH | N | |
| 171 | O | $CH_2CH{=}CH_2$ | H | $OCH_2CF_3$ | $OCH_3$ | O | CH | N | |
| 172 | O | $CH_2CH{=}CH_2$ | H | $OCH_2CF_3$ | $OCH_2CF_3$ | O | CH | N | |
| 173 | O | $CH_2CH{=}CH_2$ | H | $OCH_2CF_3$ | $OCH_3$ | O | N | N | |
| 174 | O | $CH_2CH{=}CH_2$ | H | $OCH_3$ | $NHCH_3$ | O | N | N | |
| 175 | O | $CH_2CH{=}CH_2$ | H | $OC_2H_5$ | $NHCH_3$ | O | N | N | |
| 176 | O | $CH_2CH{=}CH_2$ | H | $C_2H_5$ | $OC_2H_5$ | O | N | N | |
| 177 | O | $CH_2CH{=}CH_2$ | H | $OCH_3$ | $CH_3$ | O | N | N | |
| 178 | O | $CH_2CH{=}CH_2$ | H | Cl | $CH_3$ | O | N | N | |
| 179 | O | $CH_2CH{=}CH_2$ | H | $CH_3$ | $CH_3$ | O | N | N | |
| 180 | O | $CH_2CH{=}CH_2$ | H | $OCH_3$ | $OCH_3$ | S | CH | N | |
| 181 | O | $CH_2CH{=}CH_2$ | H | $OCH_3$ | $CH_3$ | S | CH | N | |
| 182 | O | $CH_2CH{=}CH_2$ | H | $CH_3$ | $CH_3$ | S | CH | N | |
| 183 | O | $CH_2CH{=}CH_2$ | H | $OCH_3$ | $OCH_3$ | S | N | N | |
| 184 | O | $CH_2CH{=}CH_2$ | H | $OCH_3$ | $CH_3$ | S | N | N | |
| 185 | O | $CH_2CH{=}CH_2$ | H | $CH_3$ | $CH_3$ | S | N | N | |
| 186 | O | $CH_2C{\equiv}CH$ | H | $OCH_3$ | $OCH_3$ | O | CH | N | |
| 187 | O | $CH_2C{\equiv}CH$ | $CH_3$ | $OCH_3$ | $OCH_3$ | O | CH | N | |
| 188 | O | $CH_2C{\equiv}CH$ | $CH_3$ | $OCH_3$ | $CH_3$ | O | N | N | |
| 189 | O | $CH_2C{\equiv}CH$ | H | $CH_3$ | $CH_3$ | O | CH | N | |
| 190 | O | $CH_2C{\equiv}CH$ | H | $OCH_3$ | $CH_3$ | O | CH | N | |
| 191 | O | $CH_2C{\equiv}CH$ | H | $CH_3$ | $CH_3$ | O | N | N | |
| 192 | O | $CH_2C{\equiv}CH$ | H | $OCH_3$ | $CH_3$ | O | N | N | |
| 193 | O | $CH_2C{\equiv}CH$ | H | $OCH_3$ | $OCH_3$ | O | N | N | |
| 194 | O | $CH_2C{\equiv}CH$ | H | $OCH_3$ | Cl | O | CH | N | |
| 195 | O | $CH_2C{\equiv}CH$ | H | $OCF_2H$ | $CH_3$ | O | CH | N | |
| 196 | O | $CH_2C{\equiv}CH$ | H | $OCF_2H$ | $OCF_2H$ | O | CH | N | |
| 197 | O | $CH_2C{\equiv}CH$ | H | $OCH_3$ | Br | O | CH | N | |
| 198 | O | $CH_2C{\equiv}CH$ | H | $OCH_3$ | $OC_2H_5$ | O | CH | N | |
| 199 | O | $CH_2C{\equiv}CH$ | H | $OCH_3$ | $SCH_3$ | O | CH | N | |
| 200 | O | $CH_2C{\equiv}CH$ | H | $OCH_3$ | $OC_2H_5$ | O | N | N | |
| 201 | O | $CH_2C{\equiv}CH$ | H | $OCH_3$ | $OC_3H_7$ | O | CH | N | |
| 202 | O | $CH_2C{\equiv}CH$ | H | $OCH_3$ | Cl | O | N | N | |
| 203 | O | $CH_2C{\equiv}CH$ | H | Cl | $OC_2H_5$ | O | CH | N | |
| 204 | O | $CH_2C{\equiv}CH$ | H | $OC_2H_5$ | $OC_2H_5$ | O | CH | N | |
| 205 | O | $CH_2C{\equiv}CH$ | H | $C_2H_5$ | $OCH_3$ | O | CH | N | |
| 206 | O | $CH_2C{\equiv}CH$ | H | $CF_3$ | $OCH_3$ | O | CH | N | |
| 207 | O | $CH_2C{\equiv}CH$ | H | $OCH_2CF_3$ | $CH_3$ | O | CH | N | |
| 208 | O | $CH_2C{\equiv}CH$ | H | $OCH_2CF_3$ | $OCH_3$ | O | CH | N | |
| 209 | O | $CH_2C{\equiv}CH$ | H | $OCH_2CF_3$ | $OCH_2CF_3$ | O | CH | N | |
| 210 | O | $CH_2C{\equiv}CH$ | H | $OCH_2CF_3$ | $OCH_3$ | O | N | N | |
| 211 | O | $CH_2C{\equiv}CH$ | H | $OCH_3$ | $NHCH_3$ | O | N | N | |

TABLE 3-continued

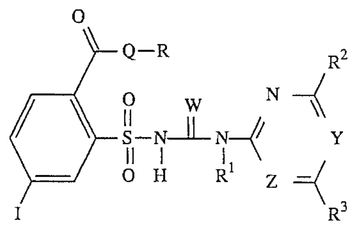

| Ex. No. | Q | R | $R^1$ | $R^2$ | $R^3$ | W | Y | Z | M.p. [°C.] |
|---|---|---|---|---|---|---|---|---|---|
| 212 | O | $CH_2C{\equiv}CH$ | H | $OC_2H_5$ | $NHCH_3$ | O | N | N | |
| 213 | O | $CH_2C{\equiv}CH$ | H | $C_2H_5$ | $OC_2H_5$ | O | N | N | |
| 214 | O | $CH_2C{\equiv}CH$ | H | $OCH_3$ | $CH_3$ | O | N | N | |
| 215 | O | $CH_2C{\equiv}CH$ | H | Cl | $CH_3$ | O | N | N | |
| 216 | O | $CH_2C{\equiv}CH$ | H | $CH_3$ | $CH_3$ | O | N | N | |
| 217 | O | $CH_2C{\equiv}CH$ | H | $OCH_3$ | $OCH_3$ | S | CH | N | |
| 218 | O | $CH_2C{\equiv}CH$ | H | $OCH_3$ | $CH_3$ | S | CH | N | |
| 219 | O | $CH_2C{\equiv}CH$ | H | $CH_3$ | $CH_3$ | S | CH | N | |
| 220 | O | $CH_2C{\equiv}CH$ | H | $OCH_3$ | $OCH_3$ | S | N | N | |
| 221 | O | $CH_2C{\equiv}CH$ | H | $OCH_3$ | $CH_3$ | S | N | N | |
| 222 | O | $CH_2C{\equiv}CH$ | H | $CH_3$ | $CH_3$ | S | N | N | |
| 223 | O | n-$C_4H_9$ | H | $OCH_3$ | $OCH_3$ | O | CH | N | |
| 224 | O | n-$C_4H_9$ | $CH_3$ | $OCH_3$ | $OCH_3$ | O | CH | N | |
| 225 | O | n-$C_4H_9$ | $CH_3$ | $OCH_3$ | $CH_3$ | O | N | N | |
| 226 | O | n-$C_4H_9$ | H | $CH_3$ | $CH_3$ | O | CH | N | |
| 227 | O | n-$C_4H_9$ | H | $OCH_3$ | $CH_3$ | O | CH | N | |
| 228 | O | n-$C_4H_9$ | H | $CH_3$ | $CH_3$ | O | N | N | |
| 229 | O | n-$C_4H_9$ | H | $OCH_3$ | $CH_3$ | O | N | N | |
| 230 | O | n-$C_4H_9$ | H | $OCH_3$ | $OCH_3$ | O | N | N | |
| 231 | O | i-$C_4H_9$ | H | $OCH_3$ | $OCH_3$ | O | CH | N | |
| 232 | O | i-$C_4H_9$ | $CH_3$ | $OCH_3$ | $OCH_3$ | O | CH | N | |
| 233 | O | i-$C_4H_9$ | $CH_3$ | $OCH_3$ | $CH_3$ | O | N | N | |
| 234 | O | i-$C_4H_9$ | H | $CH_3$ | $CH_3$ | O | CH | N | |
| 235 | O | i-$C_4H_9$ | H | $OCH_3$ | $CH_3$ | O | CH | N | |
| 236 | O | i-$C_4H_9$ | H | $CH_3$ | $CH_3$ | O | N | N | |
| 237 | O | i-$C_4H_9$ | H | $OCH_3$ | $CH_3$ | O | N | N | |
| 238 | O | i-$C_4H_9$ | H | $OCH_3$ | $OCH_3$ | O | N | N | |
| 239 | O | sec.-$C_4H_9$ | H | $OCH_3$ | $OCH_3$ | O | CH | N | |
| 240 | O | sec.-$C_4H_9$ | $CH_3$ | $OCH_3$ | $OCH_3$ | O | CH | N | |
| 241 | O | sec.-$C_4H_9$ | $CH_3$ | $OCH_3$ | $CH_3$ | O | N | N | |
| 242 | O | sec.-$C_4H_9$ | H | $CH_3$ | $CH_3$ | O | CH | N | |
| 243 | O | sec.-$C_4H_9$ | H | $OCH_3$ | $CH_3$ | O | CH | N | |
| 244 | O | sec.-$C_4H_9$ | H | $CH_3$ | $CH_3$ | O | N | N | |
| 245 | O | sec.-$C_4H_9$ | H | $OCH_3$ | $CH_3$ | O | N | N | |
| 246 | O | sec.-$C_4H_9$ | H | $OCH_3$ | $OCH_3$ | O | N | N | |
| 247 | O | t-$C_4H_9$ | H | $OCH_3$ | $OCH_3$ | O | CH | N | |
| 248 | O | t-$C_4H_9$ | $CH_3$ | $OCH_3$ | $OCH_3$ | O | CH | N | |
| 249 | O | t-$C_4H_9$ | $CH_3$ | $OCH_3$ | $CH_3$ | O | N | N | |
| 250 | O | t-$C_4H_9$ | H | $CH_3$ | $CH_3$ | O | CH | N | |
| 251 | O | t-$C_4H_9$ | H | $OCH_3$ | $CH_3$ | O | CH | N | |
| 252 | O | t-$C_4H_9$ | H | $CH_3$ | $CH_3$ | O | N | N | |
| 253 | O | t-$C_4H_9$ | H | $OCH_3$ | $CH_3$ | O | N | N | |
| 254 | O | t-$C_4H_9$ | H | $OCH_3$ | $OCH_3$ | O | N | N | |
| 255 | O | $CH_2CH_2Cl$ | H | $OCH_3$ | $OCH_3$ | O | CH | N | |
| 256 | O | $CH_2CH_2Cl$ | $CH_3$ | $OCH_3$ | $OCH_3$ | O | CH | N | |
| 257 | O | $CH_2CH_2Cl$ | $CH_3$ | $OCH_3$ | $CH_3$ | O | N | N | |
| 258 | O | $CH_2CH_2Cl$ | H | $CH_3$ | $CH_3$ | O | CH | N | |
| 259 | O | $CH_2CH_2Cl$ | H | $OCH_3$ | $CH_3$ | O | CH | N | |
| 260 | O | $CH_2CH_2Cl$ | H | $CH_3$ | $CH_3$ | O | N | N | |
| 261 | O | $CH_2CH_2Cl$ | H | $OCH_3$ | $CH_3$ | O | N | N | |
| 262 | O | $CH_2CH_2Cl$ | H | $OCH_3$ | $OCH_3$ | O | N | N | |
| 263 | O | $CH_2CH_2OCH_3$ | H | $OCH_3$ | $OCH_3$ | O | CH | N | |
| 264 | O | $CH_2CH_2OCH_3$ | $CH_3$ | $OCH_3$ | $OCH_3$ | O | CH | N | |
| 265 | O | $CH_2CH_2OCH_3$ | $CH_3$ | $OCH_3$ | $CH_3$ | O | N | N | |
| 266 | O | $CH_2CH_2OCH_3$ | H | $CH_3$ | $CH_3$ | O | CH | N | |
| 267 | O | $CH_2CH_2OCH_3$ | H | $OCH_3$ | $CH_3$ | O | CH | N | |

TABLE 3-continued

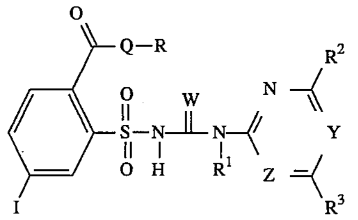

| Ex. No. | Q | R | $R^1$ | $R^2$ | $R^3$ | W | Y | Z | M.p. [°C.] |
|---|---|---|---|---|---|---|---|---|---|
| 268 | O | $CH_2CH_2OCH_3$ | H | $CH_3$ | $CH_3$ | O | N | N | |
| 269 | O | $CH_2CH_2OCH_3$ | H | $OCH_3$ | $CH_3$ | O | N | N | |
| 270 | O | $CH_2CH_2OCH_3$ | H | $OCH_3$ | $OCH_3$ | O | N | N | |
| 271 | O | c-$C_6H_{11}$ | H | $OCH_3$ | $OCH_3$ | O | CH | N | |
| 272 | O | c-$C_6H_{11}$ | $CH_3$ | $OCH_3$ | $OCH_3$ | O | CH | N | |
| 273 | O | c-$C_6H_{11}$ | $CH_3$ | $OCH_3$ | $CH_3$ | O | N | N | |
| 274 | O | c-$C_6H_{11}$ | H | $CH_3$ | $CH_3$ | O | CH | N | |
| 275 | O | c-$C_6H_{11}$ | H | $OCH_3$ | $CH_3$ | O | CH | N | |
| 276 | O | c-$C_6H_{11}$ | H | $CH_3$ | $CH_3$ | O | N | N | |
| 277 | O | c-$C_6H_{11}$ | H | $OCH_3$ | $CH_3$ | O | N | N | |
| 278 | O | c-$C_6H_{11}$ | H | $OCH_3$ | $OCH_3$ | O | N | N | |
| 279 | O | $CH_3$ | H | $OCH_3$ | $SCH_3$ | O | N | N | 185–7 |
| 280 | O | $CH_3$ | H | $SCH_3$ | $CH_3$ | O | N | N | 188 |
| 281 | O | $CH_3$ | H | $OCH_3$ | $C_2H_5$ | O | N | N | 177–8 |
| 282 | O | $CH_3$ | H | c-$C_3H_5$ | $OCH_3$ | O | N | N | 180–1 |
| 283 | O | $CH_3$ | H | $CH_2SCH_3$ | $OCH_3$ | O | N | N | 108 |
| 284 | O | $CH_3$ | H | $CH_2CH(OCH_3)_2$ | $OCH_3$ | O | N | N | 137–8 |
| 285 | O | $CH_3$ | H | 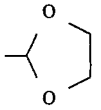 | $OCH_3$ | O | N | N | 157–8 |
| 286 | O | $CH_3$ | H | i-$C_3H_7$ | $OCH_3$ | O | N | N | 164–5 |
| 287 | O | $CH_3$ | H | n-$C_3H_7$ | $OCH_3$ | O | N | N | 154–5 |
| 288 | O | $CH_3$ | H | $CH_2Cl$ | $OCH_3$ | O | N | N | 178–9 |
| 289 | O | $CH_3$ | H | $OCH_3$ | $OCH_3$ | O | N | N | 150–5 |
| 290 | O | $CH_3$ | H | $OCH_3$ | $CH(OCH_3)_2$ | O | N | N | 108 |
| 291 | O | $CH_3$ | H | $OCH_3$ | $SCH_3$ | O | N | N | 153–5 |
| 292 | O | $C_2H_5$ | $CH_3$ | $OCH_3$ | $OCH_3$ | O | N | N | 158–60 |
| 293 | O | $CH_3$ | $CH_3$ | $OCH_3$ | $OCH_3$ | O | N | N | Na-salt 230–3 |
| 294 | O | $CH_3$ | $CH_3$ | $OCH_3$ | $OCH_3$ | O | CH | N | Na-salt 251–3 |
| 295 | O | $CH_3$ | H | $CH_3$ | $CH_3$ | O | CH | N | Na-salt 108 |
| 296 | O | $CH_3$ | H | $OCH_3$ | $CH_3$ | O | CH | N | Na-salt 135 |
| 297 | O | $CH_3$ | H | $CH_3$ | $CH_3$ | O | N | N | Na-salt 165 |
| 298 | O | $CH_3$ | H | $OCH_3$ | $CH_3$ | O | N | N | Na-salt 155 |
| 299 | O | $CH_3$ | H | $OCH_3$ | $CH_3$ | O | N | N | Li-salt 153 |
| 300 | O | $CH_3$ | H | $OCH_3$ | $CH_3$ | O | N | N | K-salt 140 |
| 301 | O | $CH_3$ | H | $OCH_3$ | $OCH_3$ | O | N | N | Na-salt 155 |
| 302 | O | $C_2H_5$ | H | $OCH_3$ | $OCH_3$ | O | CH | N | Na-salt 150 |
| 303 | O | i-$C_3H_7$ | H | $OCH_3$ | $OCH_3$ | O | CH | N | Na-salt 160 |
| 304 | O | $CH_3$ | H | $OCH_2CF_3$ | $OCH_3$ | O | N | N | Na-salt 110 |
| 305 | O | $CH_3$ | H | $OC_2H_5$ | $NHCH_3$ | O | N | N | Na-salt 115 |
| 306 | O | $C_2H_5$ | $CH_3$ | $OCH_3$ | $OCH_3$ | O | CH | N | Na-salt 115 |
| 307 | O | $C_2H_5$ | H | $OCH_3$ | $CH_3$ | O | CH | N | Na-salt 145 |
| 308 | O | $C_2H_5$ | H | $OCH_3$ | Cl | O | CH | N | Na-salt 150 |
| 309 | O | $C_2H_5$ | $CH_3$ | $OCH_3$ | $CH_3$ | O | N | N | Na-salt 113 |

TABLE 3-continued

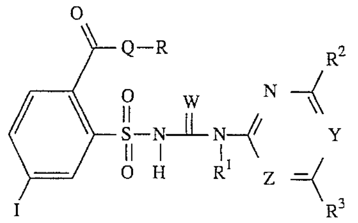

| Ex. No. | Q | R | $R^1$ | $R^2$ | $R^3$ | W | Y | Z | M.p. [°C.] |
|---|---|---|---|---|---|---|---|---|---|
| 310 | O | $C_2H_5$ | H | $OCH_3$ | $OCH_3$ | O | N | N | Na-salt 140 |
| 311 | O | $CH_3$ | H | $OCH_3$ | $C_2H_5$ | O | N | N | Na-salt 132 |
| 312 | O | $CH_3$ | H | $CH_2CH(OCH_3)_2$ | $OCH_3$ | O | N | N | Na-salt 155 |
| 313 | O | $CH_3$ | H | $CH_2SCH_3$ | $OCH_3$ | O | N | N | Na-salt 145 |
| 314 | O | $CH_3$ | H | i-$C_3H_7$ | $OCH_3$ | O | N | N | Na-salt 155 |
| 315 | O | $CH_3$ | H | n-$C_3H_7$ | $OCH_3$ | O | N | N | Na-salt 157 |
| 316 | O | $CH_3$ | H | $CH_2Cl$ | $OCH_3$ | O | N | N | Na-salt 185 |
| 317 | O | $CH_3$ | $CH_3$ | $OCH_3$ | $OCH_3$ | O | N | N | Na-salt 227–30 |
| 318 | O | $CH_3$ | H | $OCH_3$ | $CH(OCH_3)_2$ | O | N | N | Na-salt 135 |
| 319 | O | $CH_3$ | H | $SCH_3$ | $CH_3$ | O | N | N | Na-salt 165 |
| 320 | O | $C_2H_5$ | $CH_3$ | $OCH_3$ | $OCH_3$ | O | N | N | Na-salt 115 |

TABLE 4

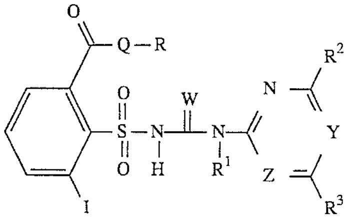

| Ex. No. | Q | R | $R^1$ | $R^2$ | $R^3$ | W | Y | Z | M.p. [°C.] |
|---|---|---|---|---|---|---|---|---|---|
| 1 | O | $CH_3$ | H | $OCH_3$ | $OCH_3$ | O | CH | N | 190–2 |
| 2 | O | $CH_3$ | $CH_3$ | $OCH_3$ | $OCH_3$ | O | CH | N | |
| 3 | O | $CH_3$ | $CH_3$ | $OCH_3$ | $CH_3$ | O | N | N | |
| 4 | O | $CH_3$ | H | $CH_3$ | $CH_3$ | O | CH | N | |
| 5 | O | $CH_3$ | H | $OCH_3$ | $CH_3$ | O | CH | N | |
| 6 | O | $CH_3$ | H | $CH_3$ | $CH_3$ | O | N | N | |
| 7 | O | $CH_3$ | H | $OCH_3$ | $CH_3$ | O | N | N | |
| 8 | O | $CH_3$ | H | $OCH_3$ | $OCH_3$ | O | N | N | |
| 9 | O | $CH_3$ | H | $OCH_3$ | Cl | O | CH | N | |
| 10 | O | $CH_3$ | H | $OCF_2H$ | $CH_3$ | O | CH | N | |
| 11 | O | $CH_3$ | H | $OCF_2H$ | $OCF_2H$ | O | CH | N | |
| 12 | O | $CH_3$ | H | $OCH_3$ | Br | O | CH | N | |
| 13 | O | $CH_3$ | H | $OCH_3$ | $OC_2H_5$ | O | CH | N | |
| 14 | O | $CH_3$ | H | $OCH_3$ | $SCH_3$ | O | CH | N | |
| 15 | O | $CH_3$ | H | $OCH_3$ | $OCH_2H_5$ | O | N | N | |
| 16 | O | $CH_3$ | H | $OCH_3$ | $OCH_3H_7$ | O | CH | N | |
| 17 | O | $CH_3$ | H | $OCH_3$ | Cl | O | N | N | |
| 18 | O | $CH_3$ | H | Cl | $OC_2H_5$ | O | CH | N | |
| 19 | O | $CH_3$ | H | $OC_2H_5$ | $OC_2H_5$ | O | CH | N | |
| 20 | O | $CH_3$ | H | $C_2H_5$ | $OCH_3$ | O | CH | N | |
| 21 | O | $CH_3$ | H | $CF_3$ | $OCH_3$ | O | CH | N | |
| 22 | O | $CH_3$ | H | $OCH_2CF_3$ | $CH_3$ | O | CH | N | |
| 23 | O | $CH_3$ | H | $OCH_2CF_3$ | $OCH_3$ | O | CH | N | |
| 24 | O | $CH_3$ | H | $OCH_2CF_3$ | $OCH_2CF_3$ | O | CH | N | |

TABLE 4-continued

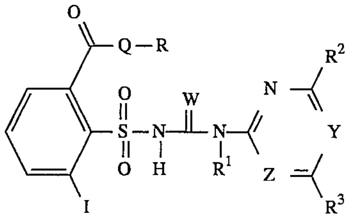

| Ex. No. | Q | R | $R^1$ | $R^2$ | $R^3$ | W | Y | Z | M.p. [°C.] |
|---|---|---|---|---|---|---|---|---|---|
| 25 | O | $CH_3$ | H | $OCH_2CF_3$ | $OCH_3$ | O | N | N | |
| 26 | O | $CH_3$ | H | $OCH_3$ | $NHCH_3$ | O | N | N | |
| 27 | O | $CH_3$ | H | $OC_2H_5$ | $NHCH_3$ | O | N | N | |
| 28 | O | $CH_3$ | H | $C_2H_5$ | $OC_2H_5$ | O | N | N | |
| 29 | O | $CH_3$ | H | $OCH_3$ | $CH_3$ | O | N | N | |
| 30 | O | $CH_3$ | H | Cl | $CH_3$ | O | N | N | |
| 31 | O | $CH_3$ | H | $CH_3$ | $CH_3$ | O | N | N | |
| 32 | O | $CH_3$ | H | $OCH_3$ | $OCH_3$ | S | CH | N | |
| 33 | O | $CH_3$ | H | $OCH_3$ | $CH_3$ | S | CH | N | |
| 34 | O | $CH_3$ | H | $CH_3$ | $CH_3$ | S | CH | N | |
| 35 | O | $CH_3$ | H | $OCH_3$ | $OCH_3$ | S | N | N | |
| 36 | O | $CH_3$ | H | $OCH_3$ | $CH_3$ | S | N | N | |
| 37 | O | $CH_3$ | H | $CH_3$ | $CH_3$ | S | N | N | |
| 38 | O | $C_2H_5$ | H | $OCH_3$ | $OCH_3$ | O | CH | N | |
| 39 | O | $C_2H_5$ | $CH_3$ | $OCH_3$ | $OCH_3$ | O | CH | N | |
| 40 | O | $C_2H_5$ | $CH_3$ | $OCH_3$ | $CH_3$ | O | N | N | |
| 41 | O | $C_2H_5$ | H | $CH_3$ | $CH_3$ | O | CH | N | |
| 42 | O | $C_2H_5$ | H | $OCH_3$ | $CH_3$ | O | CH | N | |
| 43 | O | $C_2H_5$ | H | $CH_3$ | $CH_3$ | O | N | N | |
| 44 | O | $C_2H_5$ | H | $OCH_3$ | $CH_3$ | O | N | N | |
| 45 | O | $C_2H_5$ | H | $OCH_3$ | $OCH_3$ | O | N | N | |
| 46 | O | $C_2H_5$ | H | $OCH_3$ | Cl | O | CH | N | |
| 47 | O | $C_2H_5$ | H | $OCF_2H$ | $CH_3$ | O | CH | N | |
| 48 | O | $C_2H_5$ | H | $OCF_2H$ | $OCF_2H$ | O | CH | N | |
| 49 | O | $C_2H_5$ | H | $OCH_3$ | Br | O | CH | N | |
| 50 | O | $C_2H_5$ | H | $OCH_3$ | $OC_2H_5$ | O | CH | N | |
| 51 | O | $C_2H_5$ | H | $OCH_3$ | $SCH_3$ | O | CH | N | |
| 52 | O | $C_2H_5$ | H | $OCH_3$ | $OC_2H_5$ | O | N | N | |
| 53 | O | $C_2H_5$ | H | $OCH_3$ | $OC_3H_7$ | O | CH | N | |
| 54 | O | $C_2H_5$ | H | $OCH_3$ | Cl | O | N | N | |
| 55 | O | $C_2H_5$ | H | Cl | $OC_2H_5$ | O | CH | N | |
| 56 | O | $C_2H_5$ | H | $OC_2H_5$ | $OC_2H_5$ | O | CH | N | |
| 57 | O | $C_2H_5$ | H | $C_2H_5$ | $OCH_3$ | O | CH | N | |
| 58 | O | $C_2H_5$ | H | $CF_3$ | $OCH_3$ | O | CH | N | |
| 59 | O | $C_2H_5$ | H | $OCH_2CF_3$ | $CH_3$ | O | CH | N | |
| 60 | O | $C_2H_5$ | H | $OCH_2CF_3$ | $OCH_3$ | O | CH | N | |
| 61 | O | $C_2H_5$ | H | $OCH_2CF_3$ | $OCH_2CF_3$ | O | CH | N | |
| 62 | O | $C_2H_5$ | H | $OCH_2CF_3$ | $OCH_3$ | O | N | N | |
| 63 | O | $C_2H_5$ | H | $OCH_3$ | $NHCH_3$ | O | N | N | |
| 64 | O | $C_2H_5$ | H | $OC_2H_5$ | $NHCH_3$ | O | N | N | |
| 65 | O | $C_2H_5$ | H | $C_2H_5$ | $OC_2H_5$ | O | N | N | |
| 66 | O | $C_2H_5$ | H | $OCH_3$ | $CH_3$ | O | N | N | |
| 67 | O | $C_2H_5$ | H | Cl | $CH_3$ | O | N | N | |
| 68 | O | $C_2H_5$ | H | $CH_3$ | $CH_3$ | O | N | N | |
| 69 | O | $C_2H_5$ | H | $OCH_3$ | $OCH_3$ | S | CH | N | |
| 70 | O | $C_2H_5$ | H | $OCH_3$ | $CH_3$ | S | CH | N | |
| 71 | O | $C_2H_5$ | H | $CH_3$ | $CH_3$ | S | CH | N | |
| 72 | O | $C_2H_5$ | H | $OCH_3$ | $OCH_3$ | S | N | N | |
| 73 | O | $C_2H_5$ | H | $OCH_3$ | $CH_3$ | S | N | N | |
| 74 | O | $C_2H_5$ | H | $CH_3$ | $CH_3$ | S | N | N | |
| 75 | O | n-$C_3H_7$ | H | $OCH_3$ | $OCH_3$ | O | CH | N | |
| 76 | O | n-$C_3H_7$ | $CH_3$ | $OCH_3$ | $OCH_3$ | O | CH | N | |
| 77 | O | n-$C_3H_7$ | $CH_3$ | $OCH_3$ | $CH_3$ | O | N | N | |
| 78 | O | n-$C_3H_7$ | H | $CH_3$ | $CH_3$ | O | CH | N | |
| 79 | O | n-$C_3H_7$ | H | $OCH_3$ | $CH_3$ | O | CH | N | |
| 80 | O | n-$C_3H_7$ | H | $CH_3$ | $CH_3$ | O | N | N | |
| 81 | O | n-$C_3H_7$ | H | $OCH_3$ | $CH_3$ | O | N | N | |
| 82 | O | n-$C_3H_7$ | H | $OCH_3$ | $OCH_3$ | O | N | N | |
| 83 | O | n-$C_3H_7$ | H | $OCH_3$ | Cl | O | CH | N | |
| 84 | O | n-$C_3H_7$ | H | $OCF_2H$ | $CH_3$ | O | CH | N | |
| 85 | O | n-$C_3H_7$ | H | $OCF_2H$ | $OCF_2H$ | O | CH | N | |
| 86 | O | n-$C_3H_7$ | H | $OCH_3$ | Br | O | CH | N | |
| 87 | O | n-$C_3H_7$ | H | $OCH_3$ | $OC_2H_5$ | O | CH | N | |
| 88 | O | n-$C_3H_7$ | H | $OCH_3$ | $SCH_3$ | O | CH | N | |
| 89 | O | n-$C_3H_7$ | H | $OCH_3$ | $OC_2H_5$ | O | N | N | |

TABLE 4-continued

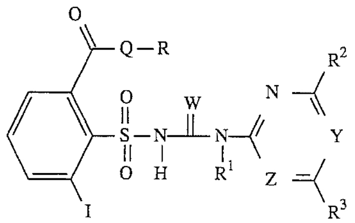

| Ex. No. | Q | R | $R^1$ | $R^2$ | $R^3$ | W | Y | Z | M.p. [°C.] |
|---|---|---|---|---|---|---|---|---|---|
| 90 | O | n-$C_3H_7$ | H | $OCH_3$ | $OC_3H_7$ | O | CH | N | |
| 91 | O | n-$C_3H_7$ | H | $OCH_3$ | Cl | O | N | N | |
| 92 | O | n-$C_3H_7$ | H | Cl | $OC_2H_5$ | O | CH | N | |
| 93 | O | n-$C_3H_7$ | H | $OC_2H_5$ | $OC_2H_5$ | O | CH | N | |
| 94 | O | n-$C_3H_7$ | H | $C_2H_5$ | $OCH_3$ | O | CH | N | |
| 95 | O | n-$C_3H_7$ | H | $CF_3$ | $OCH_3$ | O | CH | N | |
| 96 | O | n-$C_3H_7$ | H | $OCH_2CF_3$ | $CH_3$ | O | CH | N | |
| 97 | O | n-$C_3H_7$ | H | $OCH_2CF_3$ | $OCH_3$ | O | CH | N | |
| 98 | O | n-$C_3H_7$ | H | $OCH_2CF_3$ | $OCH_2CF_3$ | O | CH | N | |
| 99 | O | n-$C_3H_7$ | H | $OCH_2CF_3$ | $OCH_3$ | O | N | N | |
| 100 | O | n-$C_3H_7$ | H | $OCH_3$ | $NHCH_3$ | O | N | N | |
| 101 | O | n-$C_3H_7$ | H | $OC_2H_5$ | $NHCH_3$ | O | N | N | |
| 102 | O | n-$C_3H_7$ | H | $C_2H_5$ | $OC_2H_5$ | O | N | N | |
| 103 | O | n-$C_3H_7$ | H | $OCH_3$ | $CH_3$ | O | N | N | |
| 104 | O | n-$C_3H_7$ | H | Cl | $CH_3$ | O | N | N | |
| 105 | O | n-$C_3H_7$ | H | $CH_3$ | $CH_3$ | O | N | N | |
| 106 | O | n-$C_3H_7$ | H | $OCH_3$ | $OCH_3$ | S | CH | N | |
| 107 | O | n-$C_3H_7$ | H | $OCH_3$ | $CH_3$ | S | CH | N | |
| 108 | O | n-$C_3H_7$ | H | $CH_3$ | $CH_3$ | S | CH | N | |
| 109 | O | n-$C_3H_7$ | H | $OCH_3$ | $OCH_3$ | S | N | N | |
| 110 | O | n-$C_3H_7$ | H | $OCH_3$ | $CH_3$ | S | N | N | |
| 111 | O | n-$C_3H_7$ | H | $CH_3$ | $CH_3$ | S | N | N | |
| 112 | O | i-$C_3H_7$ | H | $OCH_3$ | $OCH_3$ | O | CH | N | |
| 113 | O | i-$C_3H_7$ | $CH_3$ | $OCH_3$ | $OCH_3$ | O | CH | N | |
| 114 | O | i-$C_3H_7$ | $CH_3$ | $OCH_3$ | $CH_3$ | O | N | N | |
| 115 | O | i-$C_3H_7$ | H | $CH_3$ | $CH_3$ | O | CH | N | |
| 116 | O | i-$C_3H_7$ | H | $OCH_3$ | $CH_3$ | O | CH | N | |
| 117 | O | i-$C_3H_7$ | H | $CH_3$ | $CH_3$ | O | N | N | |
| 118 | O | i-$C_3H_7$ | H | $OCH_3$ | $CH_3$ | O | N | N | |
| 119 | O | i-$C_3H_7$ | H | $OCH_3$ | $OCH_3$ | O | N | N | |
| 120 | O | i-$C_3H_7$ | H | $OCH_3$ | Cl | O | CH | N | |
| 121 | O | i-$C_3H_7$ | H | $OCF_2H$ | $CH_3$ | O | CH | N | |
| 122 | O | i-$C_3H_7$ | H | $OCF_2H$ | $OCF_2H$ | O | CH | N | |
| 123 | O | i-$C_3H_7$ | H | $OCH_3$ | Br | O | CH | N | |
| 124 | O | i-$C_3H_7$ | H | $OCH_3$ | $OC_2H_5$ | O | CH | N | |
| 125 | O | i-$C_3H_7$ | H | $OCH_3$ | $SCH_3$ | O | CH | N | |
| 126 | O | i-$C_3H_7$ | H | $OCH_3$ | $OC_2H_5$ | O | N | N | |
| 127 | O | i-$C_3H_7$ | H | $OCH_3$ | $OC_3H_7$ | O | CH | N | |
| 128 | O | i-$C_3H_7$ | H | $OCH_3$ | Cl | O | N | N | |
| 129 | O | i-$C_3H_7$ | H | Cl | $OC_2H_5$ | O | CH | N | |
| 130 | O | i-$C_3H_7$ | H | $OC_2H_5$ | $OC_2H_5$ | O | CH | N | |
| 131 | O | i-$C_3H_7$ | H | $C_2H_5$ | $OCH_3$ | O | CH | N | |
| 132 | O | i-$C_3H_7$ | H | $CF_3$ | $OCH_3$ | O | CH | N | |
| 133 | O | i-$C_3H_7$ | H | $OCH_2CF_3$ | $CH_3$ | O | CH | N | |
| 134 | O | i-$C_3H_7$ | H | $OCH_2CF_3$ | $OCH_3$ | O | CH | N | |
| 135 | O | i-$C_3H_7$ | H | $OCH_2CF_3$ | $OCH_2CF_3$ | O | CH | N | |
| 136 | O | i-$C_3H_7$ | H | $OCH_2CF_3$ | $OCH_3$ | O | N | N | |
| 137 | O | i-$C_3H_7$ | H | $OCH_3$ | $NHCH_3$ | O | N | N | |
| 138 | O | i-$C_3H_7$ | H | $OC_2H_5$ | $NHCH_3$ | O | N | N | |
| 139 | O | i-$C_3H_7$ | H | $C_2H_5$ | $OC_2H_5$ | O | N | N | |
| 140 | O | i-$C_3H_7$ | H | $OCH_3$ | $CH_3$ | O | N | N | |
| 141 | O | i-$C_3H_7$ | H | Cl | $CH_3$ | O | N | N | |
| 142 | O | i-$C_3H_7$ | H | $CH_3$ | $CH_3$ | O | N | N | |
| 143 | O | i-$C_3H_7$ | H | $OCH_3$ | $OCH_3$ | S | CH | N | |
| 144 | O | i-$C_3H_7$ | H | $OCH_3$ | $CH_3$ | S | CH | N | |
| 145 | O | i-$C_3H_7$ | H | $CH_3$ | $CH_3$ | S | CH | N | |
| 146 | O | i-$C_3H_7$ | H | $OCH_3$ | $OCH_3$ | S | N | N | |
| 147 | O | i-$C_3H_7$ | H | $OCH_3$ | $CH_3$ | S | N | N | |
| 148 | O | i-$C_3H_7$ | H | $CH_3$ | $CH_3$ | S | N | N | |
| 149 | O | $CH_2CH{=}CH_2$ | H | $OCH_3$ | $OCH_3$ | O | CH | N | |
| 150 | O | $CH_2CH{=}CH_2$ | $CH_3$ | $OCH_3$ | $OCH_3$ | O | CH | N | |
| 151 | O | $CH_2CH{=}CH_2$ | $CH_3$ | $OCH_3$ | $CH_3$ | O | N | N | |
| 152 | O | $CH_2CH{=}CH_2$ | H | $CH_3$ | $CH_3$ | O | CH | N | |
| 153 | O | $CH_2CH{=}CH_2$ | H | $OCH_3$ | $CH_3$ | O | CH | N | |
| 154 | O | $CH_2CH{=}CH_2$ | H | $CH_3$ | $CH_3$ | O | N | N | |

TABLE 4-continued

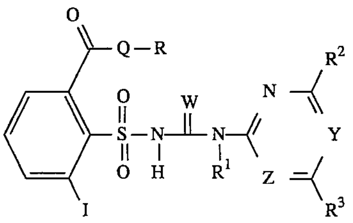

| Ex. No. | Q | R | $R^1$ | $R^2$ | $R^3$ | W | Y | Z | M.p. [°C.] |
|---|---|---|---|---|---|---|---|---|---|
| 155 | O | $CH_2CH=CH_2$ | H | $OCH_3$ | $CH_3$ | O | N | N | |
| 156 | O | $CH_2CH=CH_2$ | H | $OCH_3$ | $OCH_3$ | O | N | N | |
| 157 | O | $CH_2CH=CH_2$ | H | $OCH_3$ | Cl | O | CH | N | |
| 158 | O | $CH_2CH=CH_2$ | H | $OCF_2H$ | $CH_3$ | O | CH | N | |
| 159 | O | $CH_2CH=CH_2$ | H | $OCF_2H$ | $OCF_2H$ | O | CH | N | |
| 160 | O | $CH_2CH=CH_2$ | H | $OCH_3$ | Br | O | CH | N | |
| 161 | O | $CH_2CH=CH_2$ | H | $OCH_3$ | $OC_2H_5$ | O | CH | N | |
| 162 | O | $CH_2CH=CH_2$ | H | $OCH_3$ | $SCH_3$ | O | CH | N | |
| 163 | O | $CH_2CH=CH_2$ | H | $OCH_3$ | $OC_2H_5$ | O | N | N | |
| 164 | O | $CH_2CH=CH_2$ | H | $OCH_3$ | $OC_3H_7$ | O | CH | N | |
| 165 | O | $CH_2CH=CH_2$ | H | $OCH_3$ | Cl | O | N | N | |
| 166 | O | $CH_2CH=CH_2$ | H | Cl | $OC_2H_5$ | O | CH | N | |
| 167 | O | $CH_2CH=CH_2$ | H | $OC_2H_5$ | $OC_2H_5$ | O | CH | N | |
| 168 | O | $CH_2CH=CH_2$ | H | $C_2H_5$ | $OCH_3$ | O | CH | N | |
| 169 | O | $CH_2CH=CH_2$ | H | $CF_3$ | $OCH_3$ | O | CH | N | |
| 170 | O | $CH_2CH=CH_2$ | H | $OCH_2CF_3$ | $CH_3$ | O | CH | N | |
| 171 | O | $CH_2CH=CH_2$ | H | $OCH_2CF_3$ | $OCH_3$ | O | CH | N | |
| 172 | O | $CH_2CH=CH_2$ | H | $OCH_2CF_3$ | $OCH_2CF_3$ | O | CH | N | |
| 173 | O | $CH_2CH=CH_2$ | H | $OCH_2CF_3$ | $OCH_3$ | O | N | N | |
| 174 | O | $CH_2CH=CH_2$ | H | $OCH_3$ | $NHCH_3$ | O | N | N | |
| 175 | O | $CH_2CH=CH_2$ | H | $OC_2H_5$ | $NHCH_3$ | O | N | N | |
| 176 | O | $CH_2CH=CH_2$ | H | $C_2H_5$ | $OC_2H_5$ | O | N | N | |
| 177 | O | $CH_2CH=CH_2$ | H | $OCH_3$ | $CH_3$ | O | N | N | |
| 178 | O | $CH_2CH=CH_2$ | H | Cl | $CH_3$ | O | N | N | |
| 179 | O | $CH_2CH=CH_2$ | H | $CH_3$ | $CH_3$ | O | N | N | |
| 180 | O | $CH_2CH=CH_2$ | H | $OCH_3$ | $OCH_3$ | S | CH | N | |
| 181 | O | $CH_2CH=CH_2$ | H | $OCH_3$ | $CH_3$ | S | CH | N | |
| 182 | O | $CH_2CH=CH_2$ | H | $CH_3$ | $CH_3$ | S | CH | N | |
| 183 | O | $CH_2CH=CH_2$ | H | $OCH_3$ | $OCH_3$ | S | N | N | |
| 184 | O | $CH_2CH=CH_2$ | H | $OCH_3$ | $CH_3$ | S | N | N | |
| 185 | O | $CH_2CH=CH_2$ | H | $CH_3$ | $CH_3$ | S | N | N | |
| 186 | O | $CH_2C\equiv CH$ | H | $OCH_3$ | $OCH_3$ | O | CH | N | |
| 187 | O | $CH_2C\equiv CH$ | $CH_3$ | $OCH_3$ | $OCH_3$ | O | CH | N | |
| 188 | O | $CH_2C\equiv CH$ | $CH_3$ | $OCH_3$ | $CH_3$ | O | N | N | |
| 189 | O | $CH_2C\equiv CH$ | H | $CH_3$ | $CH_3$ | O | CH | N | |
| 190 | O | $CH_2C\equiv CH$ | H | $OCH_3$ | $CH_3$ | O | CH | N | |
| 191 | O | $CH_2C\equiv CH$ | H | $CH_3$ | $CH_3$ | O | N | N | |
| 192 | O | $CH_2C\equiv CH$ | H | $OCH_3$ | $CH_3$ | O | N | N | |
| 193 | O | $CH_2C\equiv CH$ | H | $OCH_3$ | $OCH_3$ | O | N | N | |
| 194 | O | $CH_2C\equiv CH$ | H | $OCH_3$ | Cl | O | CH | N | |
| 195 | O | $CH_2C\equiv CH$ | H | $OCF_2H$ | $CH_3$ | O | CH | N | |
| 196 | O | $CH_2C\equiv CH$ | H | $OCF_2H$ | $OCF_2H$ | O | CH | N | |
| 197 | O | $CH_2C\equiv CH$ | H | $OCH_3$ | Br | O | CH | N | |
| 198 | O | $CH_2C\equiv CH$ | H | $OCH_3$ | $OC_2H_5$ | O | CH | N | |
| 199 | O | $CH_2C\equiv CH$ | H | $OCH_3$ | $SCH_3$ | O | CH | N | |
| 200 | O | $CH_2C\equiv CH$ | H | $OCH_3$ | $OC_2H_5$ | O | N | N | |
| 201 | O | $CH_2C\equiv CH$ | H | $OCH_3$ | $OC_3H_7$ | O | CH | N | |
| 202 | O | $CH_2C\equiv CH$ | H | $OCH_3$ | Cl | O | N | N | |
| 203 | O | $CH_2C\equiv CH$ | H | Cl | $OC_2H_5$ | O | CH | N | |

TABLE 4-continued

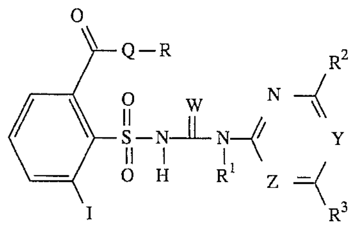

| Ex. No. | Q | R | $R^1$ | $R^2$ | $R^3$ | W | Y | Z | M.p. [°C.] |
|---|---|---|---|---|---|---|---|---|---|
| 204 | O | $CH_2C\equiv CH$ | H | $OC_2H_5$ | $OC_2H_5$ | O | CH | N | |
| 205 | O | $CH_2C\equiv CH$ | H | $C_2H_5$ | $OCH_3$ | O | CH | N | |
| 206 | O | $CH_2C\equiv CH$ | H | $CF_3$ | $OCH_3$ | O | CH | N | |
| 207 | O | $CH_2C\equiv CH$ | H | $OCH_2CF_3$ | $CH_3$ | O | CH | N | |
| 208 | O | $CH_2C\equiv CH$ | H | $OCH_2CF_3$ | $OCH_3$ | O | CH | N | |
| 209 | O | $CH_2C\equiv CH$ | H | $OCH_2CF_3$ | $OCH_2CF_3$ | O | CH | N | |
| 210 | O | $CH_2C\equiv CH$ | H | $OCH_2CF_3$ | $OCH_3$ | O | N | N | |
| 211 | O | $CH_2C\equiv CH$ | H | $OCH_3$ | $CH_3$ | O | N | N | |
| 212 | O | $CH_2C\equiv CH$ | H | $OC_2H_5$ | $NHCH_3$ | O | N | N | |
| 213 | O | $CH_2C\equiv CH$ | H | $C_2H_5$ | $OC_2H_5$ | O | N | N | |
| 214 | O | $CH_2C\equiv CH$ | H | $OCH_3$ | $CH_3$ | O | N | N | |
| 215 | O | $CH_2C\equiv CH$ | H | Cl | $CH_3$ | O | N | N | |
| 216 | O | $CH_2C\equiv CH$ | H | $CH_3$ | $CH_3$ | O | N | N | |
| 217 | O | $CH_2C\equiv CH$ | H | $OCH_3$ | $OCH_3$ | S | CH | N | |
| 218 | O | $CH_2C\equiv CH$ | H | $OCH_3$ | $CH_3$ | S | CH | N | |
| 219 | O | $CH_2C\equiv CH$ | H | $CH_3$ | $CH_3$ | S | CH | N | |
| 220 | O | $CH_2C\equiv CH$ | H | $OCH_3$ | $OCH_3$ | S | N | N | |
| 221 | O | $CH_2C\equiv CH$ | H | $OCH_3$ | $CH_3$ | S | N | N | |
| 222 | O | $CH_2C\equiv CH$ | H | $CH_3$ | $CH_3$ | S | N | N | |
| 223 | O | n-$C_4H_9$ | H | $OCH_3$ | $OCH_3$ | O | CH | N | |
| 224 | O | n-$C_4H_9$ | $CH_3$ | $OCH_3$ | $OCH_3$ | O | CH | N | |
| 225 | O | n-$C_4H_9$ | $CH_3$ | $OCH_3$ | $CH_3$ | O | N | N | |
| 226 | O | n-$C_4H_9$ | H | $CH_3$ | $CH_3$ | O | CH | N | |
| 227 | O | n-$C_4H_9$ | H | $OCH_3$ | $CH_3$ | O | CH | N | |
| 228 | O | n-$C_4H_9$ | H | $CH_3$ | $CH_3$ | O | N | N | |
| 229 | O | n-$C_4H_9$ | H | $OCH_3$ | $CH_3$ | O | N | N | |
| 230 | O | n-$C_4H_9$ | H | $OCH_3$ | $OCH_3$ | O | N | N | |
| 231 | O | i-$C_4H_9$ | H | $OCH_3$ | $OCH_3$ | O | CH | N | |
| 232 | O | i-$C_4H_9$ | $CH_3$ | $OCH_3$ | $OCH_3$ | O | CH | N | |
| 233 | O | i-$C_4H_9$ | $CH_3$ | $OCH_3$ | $CH_3$ | O | N | N | |
| 234 | O | i-$C_4H_9$ | H | $CH_3$ | $CH_3$ | O | CH | N | |
| 235 | O | i-$C_4H_9$ | H | $OCH_3$ | $CH_3$ | O | CH | N | |
| 236 | O | i-$C_4H_9$ | H | $CH_3$ | $CH_3$ | O | N | N | |
| 237 | O | i-$C_4H_9$ | H | $OCH_3$ | $CH_3$ | O | N | N | |
| 238 | O | i-$C_4H_9$ | H | $OCH_3$ | $OCH_3$ | O | N | N | |
| 239 | O | sec.-$C_4H_9$ | H | $OCH_3$ | $OCH_3$ | O | CH | N | |
| 240 | O | sec.-$C_4H_9$ | $CH_3$ | $OCH_3$ | $OCH_3$ | O | CH | N | |
| 241 | O | sec.-$C_4H_9$ | $CH_3$ | $OCH_3$ | $CH_3$ | O | N | N | |
| 242 | O | sec.-$C_4H_9$ | H | $CH_3$ | $CH_3$ | O | CH | N | |
| 243 | O | sec.-$C_4H_9$ | H | $OCH_3$ | $CH_3$ | O | CH | N | |
| 244 | O | sec.-$C_4H_9$ | H | $CH_3$ | $CH_3$ | O | N | N | |
| 245 | O | sec.-$C_4H_9$ | H | $OCH_3$ | $CH_3$ | O | N | N | |
| 246 | O | sec.-$C_4H_9$ | H | $OCH_3$ | $OCH_3$ | O | N | N | |
| 247 | O | t-$C_4H_9$ | H | $OCH_3$ | $OCH_3$ | O | CH | N | |
| 248 | O | t-$C_4H_9$ | $CH_3$ | $OCH_3$ | $OCH_3$ | O | CH | N | |
| 249 | O | t-$C_4H_9$ | $CH_3$ | $OCH_3$ | $CH_3$ | O | N | N | |
| 250 | O | t-$C_4H_9$ | H | $CH_3$ | $CH_3$ | O | CH | N | |
| 251 | O | t -$C_4H_9$ | H | $OCH_3$ | $CH_3$ | O | CH | N | |
| 252 | O | t-$C_4H_9$ | H | $CH_3$ | $CH_3$ | O | N | N | |

TABLE 4-continued

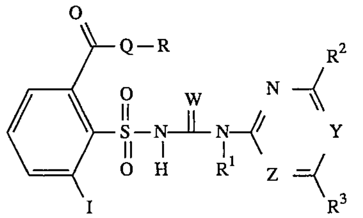

| Ex. No. | Q | R | $R^1$ | $R^2$ | $R^3$ | W | Y | Z | M.p. [°C.] |
|---|---|---|---|---|---|---|---|---|---|
| 253 | O | t-$C_4H_9$ | H | $OCH_3$ | $CH_3$ | O | N | N | |
| 254 | O | t-$C_4H_9$ | H | $OCH_3$ | $OCH_3$ | O | N | N | |
| 255 | O | $CH_2CH_2Cl$ | H | $OCH_3$ | $OCH_3$ | O | CH | N | |
| 256 | O | $CH_2CH_2Cl$ | $CH_3$ | $OCH_3$ | $OCH_3$ | O | CH | N | |
| 257 | O | $CH_2CH_2Cl$ | $CH_3$ | $OCH_3$ | $CH_3$ | O | N | N | |
| 258 | O | $CH_2CH_2Cl$ | H | $CH_3$ | $CH_3$ | O | CH | N | |
| 259 | O | $CH_2CH_2Cl$ | H | $OCH_3$ | $CH_3$ | O | CH | N | |
| 260 | O | $CH_2CH_2Cl$ | H | $CH_3$ | $CH_3$ | O | N | N | |
| 261 | O | $CH_2CH_2Cl$ | H | $OCH_3$ | $CH_3$ | O | N | N | |
| 262 | O | $CH_2CH_2Cl$ | H | $OCH_3$ | $OCH_3$ | O | N | N | |
| 263 | O | $CH_2CH_2OCH_3$ | H | $OCH_3$ | $OCH_3$ | O | CH | N | |
| 264 | O | $CH_2CH_2OCH_3$ | $CH_3$ | $OCH_3$ | $OCH_3$ | O | CH | N | |
| 265 | O | $CH_2CH_2OCH_3$ | $CH_3$ | $OCH_3$ | $CH_3$ | O | N | N | |
| 266 | O | $CH_2CH_2OCH_3$ | H | $CH_3$ | $CH_3$ | O | CH | N | |
| 267 | O | $CH_2CH_2OCH_3$ | H | $OCH_3$ | $CH_3$ | O | CH | N | |
| 268 | O | $CH_2CH_2OCH_3$ | H | $CH_3$ | $CH_3$ | O | N | N | |
| 269 | O | $CH_2CH_2OCH_3$ | H | $OCH_3$ | $CH_3$ | O | N | N | |
| 270 | O | $CH_2CH_2OCH_3$ | H | $OCH_3$ | $OCH_3$ | O | N | N | |
| 271 | O | c-$C_6H_{11}$ | H | $OCH_3$ | $OCH_3$ | O | CH | N | |
| 272 | O | c-$C_6H_{11}$ | $CH_3$ | $OCH_3$ | $OCH_3$ | O | CH | N | |
| 273 | O | c-$C_6H_{11}$ | $CH_3$ | $OCH_3$ | $CH_3$ | O | N | N | |
| 274 | O | c-$C_6H_{11}$ | H | $CH_3$ | $CH_3$ | O | CH | N | |
| 275 | O | c-$C_6H_{11}$ | H | $OCH_3$ | $CH_3$ | O | CH | N | |
| 276 | O | c-$C_6H_{11}$ | H | $CH_3$ | $CH_3$ | O | N | N | |
| 277 | O | c-$C_6H_{11}$ | H | $OCH_3$ | $CH_3$ | O | N | N | |
| 278 | O | c-$C_6H_{11}$ | H | $OCH_3$ | $OCH_3$ | O | N | N | |

TABLE 5

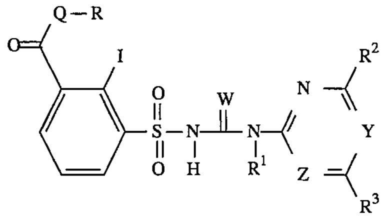

| Ex. No. | Q | R | $R^1$ | $R^2$ | $R^3$ | W | Y | Z | M.p. [°C.] |
|---|---|---|---|---|---|---|---|---|---|
| 1 | O | $CH_3$ | H | $OCH_3$ | $OCH_3$ | O | CH | N | 199–202 |
| 2 | O | $CH_3$ | $CH_3$ | $OCH_3$ | $OCH_3$ | O | CH | N | |
| 3 | O | $CH_3$ | $CH_3$ | $OCH_3$ | $CH_3$ | O | N | N | |
| 4 | O | $CH_3$ | H | $CH_3$ | $CH_3$ | O | CH | N | 212–5 |
| 5 | O | $CH_3$ | H | $OCH_3$ | $CH_3$ | O | CH | N | 193–4 |
| 6 | O | $CH_3$ | H | $CH_3$ | $CH_3$ | O | N | N | 196–7 |
| 7 | O | $CH_3$ | H | $OCH_3$ | $CH_3$ | O | N | N | 192 |
| 8 | O | $CH_3$ | H | $OCH_3$ | $OCH_3$ | O | N | N | |
| 9 | O | $CH_3$ | H | $OCH_3$ | Cl | O | CH | N | |
| 10 | O | $CH_3$ | H | $OCF_2H$ | $CH_3$ | O | CH | N | |
| 11 | O | $CH_3$ | H | $OCF_2H$ | $OCF_2H$ | O | CH | N | |
| 12 | O | $CH_3$ | H | $OCH_3$ | Br | O | CH | N | |
| 13 | O | $CH_3$ | H | $OCH_3$ | $OC_2H_5$ | O | CH | N | |
| 14 | O | $CH_3$ | H | $OCH_3$ | $SCH_3$ | O | CH | N | |
| 15 | O | $CH_3$ | H | $OCH_3$ | $OC_2H_5$ | O | N | N | |
| 16 | O | $CH_3$ | H | $OCH_3$ | $OC_3H_7$ | O | CH | N | |
| 17 | O | $CH_3$ | H | $OCH_3$ | Cl | O | N | N | |
| 18 | O | $CH_3$ | H | Cl | $OC_2H_5$ | O | CH | N | |
| 19 | O | $CH_3$ | H | $OC_2H_5$ | $OC_2H_5$ | O | CH | N | |
| 20 | O | $CH_3$ | H | $C_2H_5$ | $OCH_3$ | O | CH | N | |

TABLE 5-continued

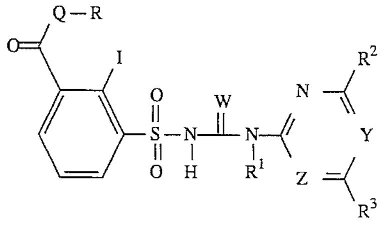

| Ex. No. | Q | R | $R^1$ | $R^2$ | $R^3$ | W | Y | Z | M.p. [°C.] |
|---|---|---|---|---|---|---|---|---|---|
| 21 | O | $CH_3$ | H | $CF_3$ | $OCH_3$ | O | CH | N | |
| 22 | O | $CH_3$ | H | $OCH_2CF_3$ | $CH_3$ | O | CH | N | |
| 23 | O | $CH_3$ | H | $OCH_2CF_3$ | $OCH_3$ | O | CH | N | |
| 24 | O | $CH_3$ | H | $OCH_2CF_3$ | $OCH_2CF_3$ | O | CH | N | |
| 25 | O | $CH_3$ | H | $OCH_2CF_3$ | $OCH_3$ | O | N | N | |
| 26 | O | $CH_3$ | H | $OCH_3$ | $NHCH_3$ | O | N | N | |
| 27 | O | $CH_3$ | H | $OC_2H_5$ | $NHCH_3$ | O | N | N | |
| 28 | O | $CH_3$ | H | $C_2H_5$ | $OC_2H_5$ | O | N | N | |
| 29 | O | $CH_3$ | H | $OCH_3$ | $CH_3$ | O | N | N | |
| 30 | O | $CH_3$ | H | Cl | $CH_3$ | O | N | N | |
| 31 | O | $CH_3$ | H | $CH_3$ | $CH_3$ | O | N | N | |
| 32 | O | $CH_3$ | H | $OCH_3$ | $OCH_3$ | S | CH | N | |
| 33 | O | $CH_3$ | H | $OCH_3$ | $CH_3$ | S | CH | N | |
| 34 | O | $CH_3$ | H | $CH_3$ | $CH_3$ | S | CH | N | |
| 35 | O | $CH_3$ | H | $OCH_3$ | $OCH_3$ | S | N | N | |
| 36 | O | $CH_3$ | H | $OCH_3$ | $CH_3$ | S | N | N | |
| 37 | O | $CH_3$ | H | $CH_3$ | $CH_3$ | S | N | N | |
| 38 | O | $C_2H_5$ | H | $OCH_3$ | $OCH_3$ | O | CH | N | 182 |
| 39 | O | $C_2H_5$ | $CH_3$ | $OCH_3$ | $OCH_3$ | O | CH | N | |
| 40 | O | $C_2H_5$ | $CH_3$ | $OCH_3$ | $CH_3$ | O | N | N | |
| 41 | O | $C_2H_5$ | H | $CH_3$ | $CH_3$ | O | CH | N | |
| 42 | O | $C_2H_5$ | H | $OCH_3$ | $CH_3$ | O | CH | N | |
| 43 | O | $C_2H_5$ | H | $CH_3$ | $CH_3$ | O | N | N | |
| 44 | O | $C_2H_5$ | H | $OCH_3$ | $CH_3$ | O | N | N | 177–179 |
| 45 | O | $C_2H_5$ | H | $OCH_3$ | $OCH_3$ | O | N | N | |
| 46 | O | $C_2H_5$ | H | $OCH_3$ | Cl | O | CH | N | |
| 47 | O | $C_2H_5$ | H | $OCF_2H$ | $CH_3$ | O | CH | N | |
| 48 | O | $C_2H_5$ | H | $OCF_2H$ | $OCF_2H$ | O | CH | N | |
| 49 | O | $C_2H_5$ | H | $OCH_3$ | Br | O | CH | N | |
| 50 | O | $C_2H_5$ | H | $OCH_3$ | $OC_2H_5$ | O | CH | N | |
| 51 | O | $C_2H_5$ | H | $OCH_3$ | $SCH_3$ | O | CH | N | |
| 52 | O | $C_2H_5$ | H | $OCH_3$ | $OC_2H_5$ | O | N | N | |
| 53 | O | $C_2H_5$ | H | $OCH_3$ | $OC_3H_7$ | O | CH | N | |
| 54 | O | $C_2H_5$ | H | $OCH_3$ | Cl | O | N | N | |
| 55 | O | $C_2H_5$ | H | Cl | $OC_2H_5$ | O | CH | N | |
| 56 | O | $C_2H_5$ | H | $OC_2H_5$ | $OC_2H_5$ | O | CH | N | |
| 57 | O | $C_2H_5$ | H | $C_2H_5$ | $OCH_3$ | O | CH | N | |
| 58 | O | $C_2H_5$ | H | $CF_3$ | $OCH_3$ | O | CH | N | |
| 59 | O | $C_2H_5$ | H | $OCH_2CF_3$ | $CH_3$ | O | CH | N | |
| 60 | O | $C_2H_5$ | H | $OCH_2CF_3$ | $OCH_3$ | O | CH | N | |
| 61 | O | $C_2H_5$ | H | $OCH_2CF_3$ | $OCH_2CF_3$ | O | CH | N | |
| 62 | O | $C_2H_5$ | H | $OCH_2CF_3$ | $OCH_3$ | O | N | N | |
| 63 | O | $C_2H_5$ | H | $OCH_3$ | $NHCH_3$ | O | N | N | |
| 64 | O | $C_2H_5$ | H | $OC_2H_5$ | $NHCH_3$ | O | N | N | |
| 65 | O | $C_2H_5$ | H | $C_2H_5$ | $OC_2H_5$ | O | N | N | |
| 66 | O | $C_2H_5$ | H | $OCH_3$ | $CH_3$ | O | N | N | |
| 67 | O | $C_2H_5$ | H | Cl | $CH_3$ | O | N | N | |
| 68 | O | $C_2H_5$ | H | $CH_3$ | $CH_3$ | O | N | N | |
| 69 | O | $C_2H_5$ | H | $OCH_3$ | $OCH_3$ | S | CH | N | |
| 70 | O | $C_2H_5$ | H | $OCH_3$ | $CH_3$ | S | CH | N | |
| 71 | O | $C_2H_5$ | H | $CH_3$ | $CH_3$ | S | CH | N | |
| 72 | O | $C_2H_5$ | H | $OCH_3$ | $OCH_3$ | S | N | N | |
| 73 | O | $C_2H_5$ | H | $OCH_3$ | $CH_3$ | S | N | N | |
| 74 | O | $C_2H_5$ | H | $CH_3$ | $CH_3$ | S | N | N | |
| 75 | O | n-$C_3H_7$ | H | $OCH_3$ | $OCH_3$ | O | CH | N | 186–188 |
| 76 | O | n-$C_3H_7$ | $CH_3$ | $OCH_3$ | $OCH_3$ | O | CH | N | |
| 77 | O | n-$C_3H_7$ | $CH_3$ | $OCH_3$ | $CH_3$ | O | N | N | |
| 78 | O | n-$C_3H_7$ | H | $CH_3$ | $CH_3$ | O | CH | N | |
| 79 | O | n-$C_3H_7$ | H | $OCH_3$ | $CH_3$ | O | CH | N | |
| 80 | O | n-$C_3H_7$ | H | $CH_3$ | $CH_3$ | O | N | N | |
| 81 | O | n-$C_3H_7$ | H | $OCH_3$ | $CH_3$ | O | N | N | 107–108 |
| 82 | O | n-$C_3H_7$ | H | $OCH_3$ | $OCH_3$ | O | N | N | |
| 83 | O | n-$C_3H_7$ | H | $OCH_3$ | Cl | O | CH | N | |
| 84 | O | n-$C_3H_7$ | H | $OCF_2H$ | $CH_3$ | O | CH | N | |
| 85 | O | n-$C_3H_7$ | H | $OCF_2H$ | $OCF_2H$ | O | CH | N | |

TABLE 5-continued

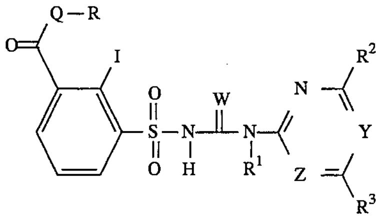

| Ex. No. | Q | R | $R^1$ | $R^2$ | $R^3$ | W | Y | Z | M.p. [°C.] |
|---|---|---|---|---|---|---|---|---|---|
| 86 | O | n-$C_3H_7$ | H | $OCH_3$ | Br | O | CH | N | |
| 87 | O | n-$C_3H_7$ | H | $OCH_3$ | $OC_2H_5$ | O | CH | N | |
| 88 | O | n-$C_3H_7$ | H | $OCH_3$ | $SCH_3$ | O | CH | N | |
| 89 | O | n-$C_3H_7$ | H | $OCH_3$ | $OC_2H_5$ | O | N | N | |
| 90 | O | n-$C_3H_7$ | H | $OCH_3$ | $OC_3H_7$ | O | CH | N | |
| 91 | O | n-$C_3H_7$ | H | $OCH_3$ | Cl | O | N | N | |
| 92 | O | n-$C_3H_7$ | H | Cl | $OC_2H_5$ | O | CH | N | |
| 93 | O | n-$C_3H_7$ | H | $OC_2H_5$ | $OC_2H_5$ | O | CH | N | |
| 94 | O | n-$C_3H_7$ | H | $C_2H_5$ | $OCH_3$ | O | CH | N | |
| 95 | O | n-$C_3H_7$ | H | $CF_3$ | $OCH_3$ | O | CH | N | |
| 96 | O | n-$C_3H_7$ | H | $OCH_2CF_3$ | $CH_3$ | O | CH | N | |
| 97 | O | n-$C_3H_7$ | H | $OCH_2CF_3$ | $OCH_3$ | O | CH | N | |
| 98 | O | n-$C_3H_7$ | H | $OCH_2CF_3$ | $OCH_2CF_3$ | O | CH | N | |
| 99 | O | n-$C_3H_7$ | H | $OCH_2CF_3$ | $OCH_3$ | O | N | N | |
| 100 | O | n-$C_3H_7$ | H | $OCH_3$ | $NHCH_3$ | O | N | N | |
| 101 | O | n-$C_3H_7$ | H | $OC_2H_5$ | $NHCH_3$ | O | N | N | |
| 102 | O | n-$C_3H_7$ | H | $C_2H_5$ | $OC_2H_5$ | O | N | N | |
| 103 | O | n-$C_3H_7$ | H | $OCH_3$ | $CH_3$ | O | N | N | |
| 104 | O | n-$C_3H_7$ | H | Cl | $CH_3$ | O | N | N | |
| 105 | O | n-$C_3H_7$ | H | $CH_3$ | $CH_3$ | O | N | N | |
| 106 | O | n-$C_3H_7$ | H | $OCH_3$ | $OCH_3$ | S | CH | N | |
| 107 | O | n-$C_3H_7$ | H | $OCH_3$ | $CH_3$ | S | CH | N | |
| 108 | O | n-$C_3H_7$ | H | $CH_3$ | $CH_3$ | S | CH | N | |
| 109 | O | n-$C_3H_7$ | H | $OCH_3$ | $OCH_3$ | S | N | N | |
| 110 | O | n-$C_3H_7$ | H | $OCH_3$ | $CH_3$ | S | N | N | |
| 111 | O | n-$C_3H_7$ | H | $CH_3$ | $CH_3$ | S | N | N | |
| 112 | O | i-$C_3H_7$ | H | $OCH_3$ | $OCH_3$ | O | CH | N | 185 |
| 113 | O | i-$C_3H_7$ | $CH_3$ | $OCH_3$ | $OCH_3$ | O | CH | N | |
| 114 | O | i-$C_3H_7$ | $CH_3$ | $OCH_3$ | $CH_3$ | O | N | N | |
| 115 | O | i-$C_3H_7$ | H | $CH_3$ | $CH_3$ | O | CH | N | |
| 116 | O | i-$C_3H_7$ | H | $OCH_3$ | $CH_3$ | O | CH | N | |
| 117 | O | i-$C_3H_7$ | H | $CH_3$ | $CH_3$ | O | N | N | |
| 118 | O | i-$C_3H_7$ | H | $OCH_3$ | $CH_3$ | O | N | N | 150 |
| 119 | O | i-$C_3H_7$ | H | $OCH_3$ | $OCH_3$ | O | N | N | |
| 120 | O | i-$C_3H_7$ | H | $OCH_3$ | Cl | O | CH | N | |
| 121 | O | i-$C_3H_7$ | H | $OCF_2H$ | $CH_3$ | O | CH | N | |
| 122 | O | i-$C_3H_7$ | H | $OCF_2H$ | $OCF_2H$ | O | CH | N | |
| 123 | O | i-$C_3H_7$ | H | $OCH_3$ | Br | O | CH | N | |
| 124 | O | i-$C_3H_7$ | H | $OCH_3$ | $OC_2H_5$ | O | CH | N | |
| 125 | O | i-$C_3H_7$ | H | $OCH_3$ | $SCH_3$ | O | CH | N | |
| 126 | O | i-$C_3H_7$ | H | $OCH_3$ | $OC_2H_5$ | O | N | N | |
| 127 | O | i-$C_3H_7$ | H | $OCH_3$ | $OC_3H_7$ | O | CH | N | |
| 128 | O | i-$C_3H_7$ | H | $OCH_3$ | Cl | O | N | N | |
| 129 | O | i-$C_3H_7$ | H | Cl | $OC_2H_5$ | O | CH | N | |
| 130 | O | i-$C_3H_7$ | H | $OC_2H_5$ | $OC_2H_5$ | O | CH | N | |
| 131 | O | i-$C_3H_7$ | H | $C_2H_5$ | $OCH_3$ | O | CH | N | |
| 132 | O | i-$C_3H_7$ | H | $CF_3$ | $OCH_3$ | O | CH | N | |
| 133 | O | i-$C_3H_7$ | H | $OCH_2CF_3$ | $CH_3$ | O | CH | N | |
| 134 | O | i-$C_3H_7$ | H | $OCH_2CF_3$ | $OCH_3$ | O | CH | N | |
| 135 | O | i-$C_3H_7$ | H | $OCH_2CF_3$ | $OCH_2CF_3$ | O | CH | N | |
| 136 | O | i-$C_3H_7$ | H | $OCH_2CF_3$ | $OCH_3$ | O | N | N | |
| 137 | O | i-$C_3H_7$ | H | $OCH_3$ | $NHCH_3$ | O | N | N | |
| 138 | O | i-$C_3H_7$ | H | $OC_2H_5$ | $NHCH_3$ | O | N | N | |
| 139 | O | i-$C_3H_7$ | H | $C_2H_5$ | $OC_2H_5$ | O | N | N | |
| 140 | O | i-$C_3H_7$ | H | $OCH_3$ | $CH_3$ | O | N | N | |
| 141 | O | i-$C_3H_7$ | H | Cl | $CH_3$ | O | N | N | |
| 142 | O | i-$C_3H_7$ | H | $CH_3$ | $CH_3$ | O | N | N | |
| 143 | O | i-$C_3H_7$ | H | $OCH_3$ | $OCH_3$ | S | CH | N | |
| 144 | O | i-$C_3H_7$ | H | $OCH_3$ | $CH_3$ | S | CH | N | |
| 145 | O | i-$C_3H_7$ | H | $CH_3$ | $CH_3$ | S | CH | N | |
| 146 | O | i-$C_3H_7$ | H | $OCH_3$ | $OCH_3$ | S | N | N | |
| 147 | O | i-$C_3H_7$ | H | $OCH_3$ | $CH_3$ | S | N | N | |
| 148 | O | i-$C_3H_7$ | H | $CH_3$ | $CH_3$ | S | N | N | |
| 149 | O | $CH_2CH{=}CH_2$ | H | $OCH_3$ | $OCH_3$ | O | CH | N | |
| 150 | O | $CH_2CH{=}CH_2$ | $CH_3$ | $OCH_3$ | $OCH_3$ | O | CH | N | |

TABLE 5-continued

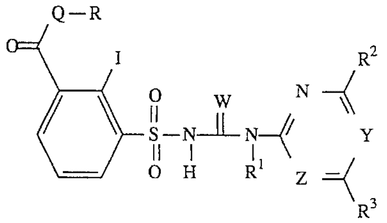

| Ex. No. | Q | R | $R^1$ | $R^2$ | $R^3$ | W | Y | Z | M.p. [°C.] |
|---|---|---|---|---|---|---|---|---|---|
| 151 | O | $CH_2CH{=}CH_2$ | $CH_3$ | $OCH_3$ | $CH_3$ | O | N | N | |
| 152 | O | $CH_2CH{=}CH_2$ | H | $CH_3$ | $CH_3$ | O | CH | N | |
| 153 | O | $CH_2CH{=}CH_2$ | H | $OCH_3$ | $CH_3$ | O | CH | N | |
| 154 | O | $CH_2CH{=}CH_2$ | H | $CH_3$ | $CH_3$ | O | N | N | |
| 155 | O | $CH_2CH{=}CH_2$ | H | $OCH_3$ | $CH_3$ | O | N | N | |
| 156 | O | $CH_2CH{=}CH_2$ | H | $OCH_3$ | $OCH_3$ | O | N | N | |
| 157 | O | $CH_2CH{=}CH_2$ | H | $OCH_3$ | Cl | O | CH | N | |
| 158 | O | $CH_2CH{=}CH_2$ | H | $OCF_2H$ | $CH_3$ | O | CH | N | |
| 159 | O | $CH_2CH{=}CH_2$ | H | $OCF_2H$ | $OCF_2H$ | O | CH | N | |
| 160 | O | $CH_2CH{=}CH_2$ | H | $OCH_3$ | Br | O | CH | N | |
| 161 | O | $CH_2CH{=}CH_2$ | H | $OCH_3$ | $OC_2H_5$ | O | CH | N | |
| 162 | O | $CH_2CH{=}CH_2$ | H | $OCH_3$ | $SCH_3$ | O | CH | N | |
| 163 | O | $CH_2CH{=}CH_2$ | H | $OCH_3$ | $OC_2H_5$ | O | N | N | |
| 164 | O | $CH_2CH{=}CH_2$ | H | $OCH_3$ | $OC_3H_7$ | O | CH | N | |
| 165 | O | $CH_2CH{=}CH_2$ | H | $OCH_3$ | Cl | O | N | N | |
| 166 | O | $CH_2CH{=}CH_2$ | H | Cl | $OC_2H_5$ | O | CH | N | |
| 167 | O | $CH_2CH{=}CH_2$ | H | $OC_2H_5$ | $OC_2H_5$ | O | CH | N | |
| 168 | O | $CH_2CH{=}CH_2$ | H | $C_2H_5$ | $OCH_3$ | O | CH | N | |
| 169 | O | $CH_2CH{=}CH_2$ | H | $CF_3$ | $OCH_3$ | O | CH | N | |
| 170 | O | $CH_2CH{=}CH_2$ | H | $OCH_2CF_3$ | $CH_3$ | O | CH | N | |
| 171 | O | $CH_2CH{=}CH_2$ | H | $OCH_2CF_3$ | $OCH_3$ | O | CH | N | |
| 172 | O | $CH_2CH{=}CH_2$ | H | $OCH_2CF_3$ | $OCH_2CF_3$ | O | CH | N | |
| 173 | O | $CH_2CH{=}CH_2$ | H | $OCH_2CF_3$ | $OCH_3$ | O | N | N | |
| 174 | O | $CH_2CH{=}CH_2$ | H | $OCH_3$ | $NHCH_3$ | O | N | N | |
| 175 | O | $CH_2CH{=}CH_2$ | H | $OC_2H_5$ | $NHCH_3$ | O | N | N | |
| 176 | O | $CH_2CH{=}CH_2$ | H | $C_2H_5$ | $OC_2H_5$ | O | N | N | |
| 177 | O | $CH_2CH{=}CH_2$ | H | $OCH_3$ | $CH_3$ | O | N | N | |
| 178 | O | $CH_2CH{=}CH_2$ | H | Cl | $CH_3$ | O | N | N | |
| 179 | O | $CH_2CH{=}CH_2$ | H | $CH_3$ | $CH_3$ | O | N | N | |
| 180 | O | $CH_2CH{=}CH_2$ | H | $OCH_3$ | $OCH_3$ | S | CH | N | |
| 181 | O | $CH_2CH{=}CH_2$ | H | $OCH_3$ | $CH_3$ | S | CH | N | |
| 182 | O | $CH_2CH{=}CH_2$ | H | $CH_3$ | $CH_3$ | S | CH | N | |
| 183 | O | $CH_2CH{=}CH_2$ | H | $OCH_3$ | $OCH_3$ | S | N | N | |
| 184 | O | $CH_2CH{=}CH_2$ | H | $OCH_3$ | $CH_3$ | S | N | N | |
| 185 | O | $CH_2CH{=}CH_2$ | H | $CH_3$ | $CH_3$ | S | N | N | |
| 186 | O | $CH_2C{\equiv}CH$ | H | $OCH_3$ | $OCH_3$ | O | CH | N | |
| 187 | O | $CH_2C{\equiv}CH$ | $CH_3$ | $OCH_3$ | $OCH_3$ | O | CH | N | |
| 188 | O | $CH_2C{\equiv}CH$ | $CH_3$ | $OCH_3$ | $CH_3$ | O | N | N | |
| 189 | O | $CH_2C{\equiv}CH$ | H | $CH_3$ | $CH_3$ | O | CH | N | |
| 190 | O | $CH_2C{\equiv}CH$ | H | $OCH_3$ | $CH_3$ | O | CH | N | |
| 191 | O | $CH_2C{\equiv}CH$ | H | $CH_3$ | $CH_3$ | O | N | N | |
| 192 | O | $CH_2C{\equiv}CH$ | H | $OCH_3$ | $CH_3$ | O | N | N | |
| 193 | O | $CH_2C{\equiv}CH$ | H | $OCH_3$ | $OCH_3$ | O | N | N | |
| 194 | O | $CH_2C{\equiv}CH$ | H | $OCH_3$ | Cl | O | CH | N | |
| 195 | O | $CH_2C{\equiv}CH$ | H | $OCF_2H$ | $CH_3$ | O | CH | N | |
| 196 | O | $CH_2C{\equiv}CH$ | H | $OCF_2H$ | $OCF_2H$ | O | CH | N | |
| 197 | O | $CH_2C{\equiv}CH$ | H | $OCH_3$ | Br | O | CH | N | |
| 198 | O | $CH_2C{\equiv}CH$ | H | $OCH_3$ | $OC_2H_5$ | O | CH | N | |
| 199 | O | $CH_2C{\equiv}CH$ | H | $OCH_3$ | $SCH_3$ | O | CH | N | |
| 200 | O | $CH_2C{\equiv}CH$ | H | $OCH_3$ | $OC_2H_5$ | O | N | N | |
| 201 | O | $CH_2C{\equiv}CH$ | H | $OCH_3$ | $OC_3H_7$ | O | CH | N | |

TABLE 5-continued

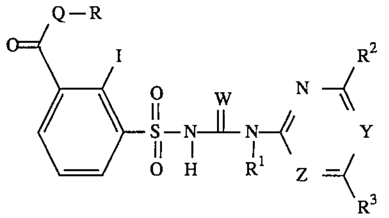

| Ex. No. | Q | R | $R^1$ | $R^2$ | $R^3$ | W | Y | Z | M.p. [°C.] |
|---|---|---|---|---|---|---|---|---|---|
| 202 | O | $CH_2C{\equiv}CH$ | H | $OCH_3$ | Cl | O | N | N | |
| 203 | O | $CH_2C{\equiv}CH$ | H | Cl | $OC_2H_5$ | O | CH | N | |
| 204 | O | $CH_2C{\equiv}CH$ | H | $OC_2H_5$ | $OC_2H_5$ | O | CH | N | |
| 205 | O | $CH_2C{\equiv}CH$ | H | $C_2H_5$ | $OCH_3$ | O | CH | N | |
| 206 | O | $CH_2C{\equiv}CH$ | H | $CF_3$ | $OCH_3$ | O | CH | N | |
| 207 | O | $CH_2C{\equiv}CH$ | H | $OCH_2CF_3$ | $CH_3$ | O | CH | N | |
| 208 | O | $CH_2C{\equiv}CH$ | H | $OCH_2CF_3$ | $OCH_3$ | O | CH | N | |
| 209 | O | $CH_2C{\equiv}CH$ | H | $OCH_2CF_3$ | $OCH_2CF_3$ | O | CH | N | |
| 210 | O | $CH_2C{\equiv}CH$ | H | $OCH_2CF_3$ | $OCH_3$ | O | N | N | |
| 211 | O | $CH_2C{\equiv}CH$ | H | $OCH_3$ | $NHCH_3$ | O | N | N | |
| 212 | O | $CH_2C{\equiv}CH$ | H | $OC_2H_5$ | $NHCH_3$ | O | N | N | |
| 213 | O | $CH_2C{\equiv}CH$ | H | $C_2H_5$ | $OC_2H_5$ | O | N | N | |
| 214 | O | $CH_2C{\equiv}CH$ | H | $OCH_3$ | $CH_3$ | O | N | N | |
| 215 | O | $CH_2C{\equiv}CH$ | H | Cl | $CH_3$ | O | N | N | |
| 216 | O | $CH_2C{\equiv}CH$ | H | $CH_3$ | $CH_3$ | O | N | N | |
| 217 | O | $CH_2C{\equiv}CH$ | H | $OCH_3$ | $OCH_3$ | S | CH | N | |
| 218 | O | $CH_2C{\equiv}CH$ | H | $OCH_3$ | $CH_3$ | S | CH | N | |
| 219 | O | $CH_2C{\equiv}CH$ | H | $CH_3$ | $CH_3$ | S | CH | N | |
| 220 | O | $CH_2C{\equiv}CH$ | H | $OCH_3$ | $OCH_3$ | S | N | N | |
| 221 | O | $CH_2C{\equiv}CH$ | H | $OCH_3$ | $CH_3$ | S | N | N | |
| 222 | O | $CH_2C{\equiv}CH$ | H | $CH_3$ | $CH_3$ | S | N | N | |
| 223 | O | n-$C_4H_9$ | H | $OCH_3$ | $OCH_3$ | O | CH | N | |
| 224 | O | n-$C_4H_9$ | $CH_3$ | $OCH_3$ | $OCH_3$ | O | CH | N | |
| 225 | O | n-$C_4H_9$ | $CH_3$ | $OCH_3$ | $CH_3$ | O | N | N | |
| 226 | O | n-$C_4H_9$ | H | $CH_3$ | $CH_3$ | O | CH | N | |
| 227 | O | n-$C_4H_9$ | H | $OCH_3$ | $CH_3$ | O | CH | N | |
| 228 | O | n-$C_4H_9$ | H | $CH_3$ | $CH_3$ | O | N | N | |
| 229 | O | n-$C_4H_9$ | H | $OCH_3$ | $CH_3$ | O | N | N | |
| 230 | O | n-$C_4H_9$ | H | $OCH_3$ | $OCH_3$ | O | N | N | |
| 231 | O | i-$C_4H_9$ | H | $OCH_3$ | $OCH_3$ | O | CH | N | |
| 232 | O | i-$C_4H_9$ | $CH_3$ | $OCH_3$ | $OCH_3$ | O | CH | N | |
| 233 | O | i-$C_4H_9$ | $CH_3$ | $OCH_3$ | $CH_3$ | O | N | N | |
| 234 | O | i-$C_4H_9$ | H | $CH_3$ | $CH_3$ | O | CH | N | |
| 235 | O | i-$C_4H_9$ | H | $OCH_3$ | $CH_3$ | O | CH | N | |
| 236 | O | i-$C_4H_9$ | H | $CH_3$ | $CH_3$ | O | N | N | |
| 237 | O | i-$C_4H_9$ | H | $OCH_3$ | $CH_3$ | O | N | N | |
| 238 | O | i-$C_4H_9$ | H | $OCH_3$ | $OCH_3$ | O | N | N | |
| 239 | O | sec.-$C_4H_9$ | H | $OCH_3$ | $OCH_3$ | O | CH | N | |
| 240 | O | sec.-$C_4H_9$ | $CH_3$ | $OCH_3$ | $OCH_3$ | O | CH | N | |
| 241 | O | sec.-$C_4H_9$ | $CH_3$ | $OCH_3$ | $CH_3$ | O | N | N | |
| 242 | O | sec.-$C_4H_9$ | H | $CH_3$ | $CH_3$ | O | CH | N | |
| 243 | O | sec.-$C_4H_9$ | H | $OCH_3$ | $CH_3$ | O | CH | N | |
| 244 | O | sec.-$C_4H_9$ | H | $CH_3$ | $CH_3$ | O | N | N | |
| 245 | O | sec.-$C_4H_9$ | H | $OCH_3$ | $CH_3$ | O | N | N | |
| 246 | O | sec.-$C_4H_9$ | H | $OCH_3$ | $OCH_3$ | O | N | N | |
| 247 | O | t-$C_4H_9$ | H | $OCH_3$ | $OCH_3$ | O | CH | N | |
| 248 | O | t-$C_4H_9$ | $CH_3$ | $OCH_3$ | $OCH_3$ | O | CH | N | |

TABLE 5-continued

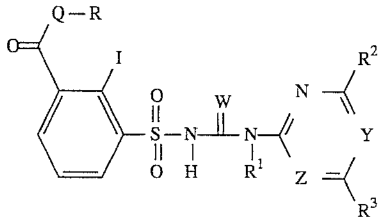

| Ex. No. | Q | R | $R^1$ | $R^2$ | $R^3$ | W | Y | Z | M.p. [°C.] |
|---|---|---|---|---|---|---|---|---|---|
| 249 | O | t-$C_4H_9$ | $CH_3$ | $OCH_3$ | $CH_3$ | O | N | N | |
| 250 | O | t-$C_4H_9$ | H | $CH_3$ | $CH_3$ | O | CH | N | |
| 251 | O | t-$C_4H_9$ | H | $OCH_3$ | $CH_3$ | O | CH | N | |
| 252 | O | t-$C_4H_9$ | H | $CH_3$ | $CH_3$ | O | N | N | |
| 253 | O | t-$C_4H_9$ | H | $OCH_3$ | $CH_3$ | O | N | N | |
| 254 | O | t-$C_4H_9$ | H | $OCH_3$ | $OCH_3$ | O | N | N | |
| 255 | O | $CH_2CH_2Cl$ | H | $OCH_3$ | $OCH_3$ | O | CH | N | |
| 256 | O | $CH_2CH_2Cl$ | $CH_3$ | $OCH_3$ | $OCH_3$ | O | CH | N | |
| 257 | O | $CH_2CH_2Cl$ | $CH_3$ | $OCH_3$ | $CH_3$ | O | N | N | |
| 258 | O | $CH_2CH_2Cl$ | H | $CH_3$ | $CH_3$ | O | CH | N | |
| 259 | O | $CH_2CH_2Cl$ | H | $OCH_3$ | $CH_3$ | O | CH | N | |
| 260 | O | $CH_2CH_2Cl$ | H | $CH_3$ | $CH_3$ | O | N | N | |
| 261 | O | $CH_2CH_2Cl$ | H | $OCH_3$ | $CH_3$ | O | N | N | |
| 262 | O | $CH_2CH_2Cl$ | H | $OCH_3$ | $OCH_3$ | O | N | N | |
| 263 | O | $CH_2CH_2OCH_3$ | H | $OCH_3$ | $OCH_3$ | O | CH | N | |
| 264 | O | $CH_2CH_2OCH_3$ | $CH_3$ | $OCH_3$ | $OCH_3$ | O | CH | N | |
| 265 | O | $CH_2CH_2OCH_3$ | $CH_3$ | $OCH_3$ | $CH_3$ | O | N | N | |
| 266 | O | $CH_2CH_2OCH_3$ | H | $CH_3$ | $CH_3$ | O | CH | N | |
| 267 | O | $CH_2CH_2OCH_3$ | H | $OCH_3$ | $CH_3$ | O | CH | N | |
| 268 | O | $CH_2CH_2OCH_3$ | H | $CH_3$ | $CH_3$ | O | N | N | |
| 269 | O | $CH_2CH_2OCH_3$ | H | $OCH_3$ | $CH_3$ | O | N | N | |
| 270 | O | $CH_2CH_2OCH_3$ | H | $OCH_3$ | $OCH_3$ | O | N | N | |
| 271 | O | c-$C_6H_{11}$ | H | $OCH_3$ | $OCH_3$ | O | CH | N | |
| 272 | O | c-$C_6H_{11}$ | $CH_3$ | $OCH_3$ | $OCH_3$ | O | CH | N | |
| 273 | O | c-$C_6H_{11}$ | $CH_3$ | $OCH_3$ | $CH_3$ | O | N | N | |
| 274 | O | c-$C_6H_{11}$ | H | $CH_3$ | $CH_3$ | O | CH | N | |
| 275 | O | c-$C_6H_{11}$ | H | $OCH_3$ | $CH_3$ | O | CH | N | |
| 276 | O | c-$C_6H_{11}$ | H | $CH_3$ | $CH_3$ | O | N | N | |
| 277 | O | c-$C_6H_{11}$ | H | $OCH_3$ | $CH_3$ | O | N | N | |
| 278 | O | c-$C_6H_{11}$ | H | $OCH_3$ | $OCH_3$ | O | N | N | |
| 279 | O | $CH_3$ | H | $CH_3$ | Cl | O | CH | N | 214–6 decomp. |
| 280 | O | $CH_3$ | H | $CH_3$ | H | O | CH | N | 201-3 decomp. |
| 281 | O | $CH_3$ | H | $OCH_3$ | $CH_3$ | O | N | N | Na-salt 200 |

TABLE 6

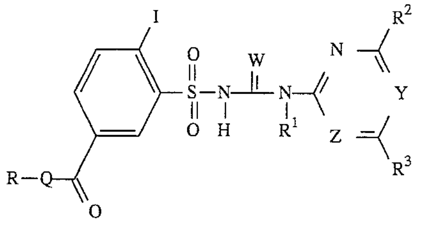

| Ex. No. | Q | R | $R^1$ | $R^2$ | $R^3$ | W | Y | Z | M.p. [°C.] |
|---|---|---|---|---|---|---|---|---|---|
| 1 | O | $CH_3$ | H | $OCH_3$ | $OCH_3$ | O | CH | N | 173–177 |
| 2 | O | $CH_3$ | $CH_3$ | $OCH_3$ | $OCH_3$ | O | CH | N | |
| 3 | O | $CH_3$ | $CH_3$ | $OCH_3$ | $CH_3$ | O | N | N | |
| 4 | O | $CH_3$ | H | $CH_3$ | $CH_3$ | O | CH | N | |
| 5 | O | $CH_3$ | H | $OCH_3$ | $CH_3$ | O | CH | N | |
| 6 | O | $CH_3$ | H | $CH_3$ | $CH_3$ | O | N | N | |
| 7 | O | $CH_3$ | H | $OCH_3$ | $CH_3$ | O | N | N | 187–188 |
| 8 | O | $CH_3$ | H | $OCH_3$ | $OCH_3$ | O | N | N | |
| 9 | O | $CH_3$ | H | $OCH_3$ | Cl | O | CH | N | |
| 10 | O | $CH_3$ | H | $OCF_2H$ | $CH_3$ | O | CH | N | |
| 11 | O | $CH_3$ | H | $OCF_2H$ | $OCF_2H$ | O | CH | N | |
| 12 | O | $CH_3$ | H | $OCH_3$ | Br | O | CH | N | |
| 13 | O | $CH_3$ | H | $OCH_3$ | $OC_2H_5$ | O | CH | N | |

TABLE 6-continued

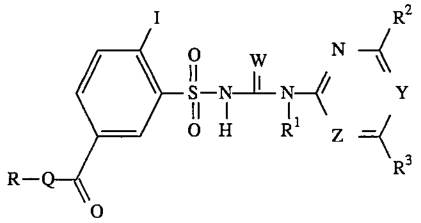

| Ex. No. | Q | R | $R^1$ | $R^2$ | $R^3$ | W | Y | Z | M.p. [°C.] |
|---|---|---|---|---|---|---|---|---|---|
| 14 | O | $CH_3$ | H | $OCH_3$ | $SCH_3$ | O | CH | N | |
| 15 | O | $CH_3$ | H | $OCH_3$ | $OC_2H_5$ | O | N | N | |
| 16 | O | $CH_3$ | H | $OCH_3$ | $OC_3H_7$ | O | CH | N | |
| 17 | O | $CH_3$ | H | $OCH_3$ | Cl | O | N | N | |
| 18 | O | $CH_3$ | H | Cl | $OC_2H_5$ | O | CH | N | |
| 19 | O | $CH_3$ | H | $OC_2H_5$ | $OC_2H_5$ | O | CH | N | |
| 20 | O | $CH_3$ | H | $C_2H_5$ | $OCH_3$ | O | CH | N | |
| 21 | O | $CH_3$ | H | $CF_3$ | $OCH_3$ | O | CH | N | |
| 22 | O | $CH_3$ | H | $OCH_2CF_3$ | $CH_3$ | O | CH | N | |
| 23 | O | $CH_3$ | H | $OCH_2CF_3$ | $OCH_3$ | O | CH | N | |
| 24 | O | $CH_3$ | H | $OCH_2CF_3$ | $OCH_2CF_3$ | O | CH | N | |
| 25 | O | $CH_3$ | H | $OCH_2CF_3$ | $OCH_3$ | O | N | N | |
| 26 | O | $CH_3$ | H | $OCH_3$ | $NHCH_3$ | O | N | N | |
| 27 | O | $CH_3$ | H | $OC_2H_5$ | $NHCH_3$ | O | N | N | |
| 28 | O | $CH_3$ | H | $C_2H_5$ | $OC_2H_5$ | O | N | N | |
| 29 | O | $CH_3$ | H | $OCH_3$ | $CH_3$ | O | N | N | |
| 30 | O | $CH_3$ | H | Cl | $CH_3$ | O | N | N | |
| 31 | O | $CH_3$ | H | $CH_3$ | $CH_3$ | O | N | N | |
| 32 | O | $CH_3$ | H | $OCH_3$ | $OCH_3$ | S | CH | N | |
| 33 | O | $CH_3$ | H | $OCH_3$ | $CH_3$ | S | CH | N | |
| 34 | O | $CH_3$ | H | $CH_3$ | $CH_3$ | S | CH | N | |
| 35 | O | $CH_3$ | H | $OCH_3$ | $OCH_3$ | S | N | N | |
| 36 | O | $CH_3$ | H | $OCH_3$ | $CH_3$ | S | N | N | |
| 37 | O | $CH_3$ | H | $CH_3$ | $CH_3$ | S | N | N | |
| 38 | O | $C_2H_5$ | H | $OCH_3$ | $OCH_3$ | O | CH | N | |
| 39 | O | $C_2H_5$ | $CH_3$ | $OCH_3$ | $OCH_3$ | O | CH | N | |
| 40 | O | $C_2H_5$ | $CH_3$ | $OCH_3$ | $CH_3$ | O | N | N | |
| 41 | O | $C_2H_5$ | H | $CH_3$ | $CH_3$ | O | CH | N | |
| 42 | O | $C_2H_5$ | H | $OCH_3$ | $CH_3$ | O | CH | N | |
| 43 | O | $C_2H_5$ | H | $CH_3$ | $CH_3$ | O | N | N | |
| 44 | O | $C_2H_5$ | H | $OCH_3$ | $CH_3$ | O | N | N | |
| 45 | O | $C_2H_5$ | H | $OCH_3$ | $OCH_3$ | O | N | N | |
| 46 | O | $C_2H_5$ | H | $OCH_3$ | Cl | O | CH | N | |
| 47 | O | $C_2H_5$ | H | $OCF_2H$ | $CH_3$ | O | CH | N | |
| 48 | O | $C_2H_5$ | H | $OCF_2H$ | $OCF_2H$ | O | CH | N | |
| 49 | O | $C_2H_5$ | H | $OCH_3$ | Br | O | CH | N | |
| 50 | O | $C_2H_5$ | H | $OCH_3$ | $OC_2H_5$ | O | CH | N | |
| 51 | O | $C_2H_5$ | H | $OCH_3$ | $SCH_3$ | O | CH | N | |
| 52 | O | $C_2H_5$ | H | $OCH_3$ | $OC_2H_5$ | O | N | N | |
| 53 | O | $C_2H_5$ | H | $OCH_3$ | $OC_3H_7$ | O | CH | N | |
| 54 | O | $C_2H_5$ | H | $OCH_3$ | Cl | O | N | N | |
| 55 | O | $C_2H_5$ | H | Cl | $OC_2H_5$ | O | CH | N | |
| 56 | O | $C_2H_5$ | H | $OC_2H_5$ | $OC_2H_5$ | O | CH | N | |
| 57 | O | $C_2H_5$ | H | $C_2H_5$ | $OCH_3$ | O | CH | N | |
| 58 | O | $C_2H_5$ | H | $CF_3$ | $OCH_3$ | O | CH | N | |
| 59 | O | $C_2H_5$ | H | $OCH_2CF_3$ | $CH_3$ | O | CH | N | |
| 60 | O | $C_2H_5$ | H | $OCH_2CF_3$ | $OCH_3$ | O | CH | N | |
| 61 | O | $C_2H_5$ | H | $OCH_2CF_3$ | $OCH_2CF_3$ | O | CH | N | |
| 62 | O | $C_2H_5$ | H | $OCH_2CF_3$ | $OCH_3$ | O | N | N | |
| 63 | O | $C_2H_5$ | H | $OCH_3$ | $NHCH_3$ | O | N | N | |
| 64 | O | $C_2H_5$ | H | $OC_2H_5$ | $NHCH_3$ | O | N | N | |
| 65 | O | $C_2H_5$ | H | $C_2H_5$ | $OC_2H_5$ | O | N | N | |
| 66 | O | $C_2H_5$ | H | $OCH_3$ | $CH_3$ | O | N | N | |
| 67 | O | $C_2H_5$ | H | Cl | $CH_3$ | O | N | N | |
| 68 | O | $C_2H_5$ | H | $CH_3$ | $CH_3$ | O | N | N | |
| 69 | O | $C_2H_5$ | H | $OCH_3$ | $OCH_3$ | S | CH | N | |
| 70 | O | $C_2H_5$ | H | $OCH_3$ | $CH_3$ | S | CH | N | |
| 71 | O | $C_2H_5$ | H | $CH_3$ | $CH_3$ | S | CH | N | |
| 72 | O | $C_2H_5$ | H | $OCH_3$ | $OCH_3$ | S | N | N | |
| 73 | O | $C_2H_5$ | H | $OCH_3$ | $CH_3$ | S | N | N | |
| 74 | O | $C_2H_5$ | H | $CH_3$ | $CH_3$ | S | N | N | |
| 75 | O | n-$C_3H_7$ | H | $OCH_3$ | $OCH_3$ | O | CH | N | |
| 76 | O | n-$C_3H_7$ | $CH_3$ | $OCH_3$ | $OCH_3$ | O | CH | N | |
| 77 | O | n-$C_3H_7$ | $CH_3$ | $OCH_3$ | $CH_3$ | O | N | N | |
| 78 | O | n-$C_3H_7$ | H | $CH_3$ | $CH_3$ | O | CH | N | |
| 79 | O | n-$C_3H_7$ | H | $OCH_3$ | $CH_3$ | O | CH | N | |

TABLE 6-continued

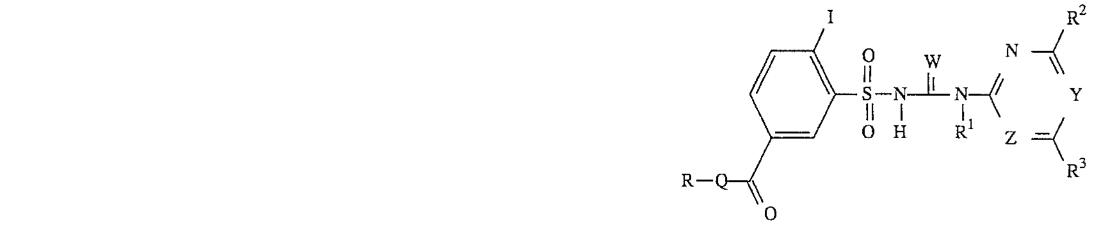

| Ex. No. | Q | R | $R^1$ | $R^2$ | $R^3$ | W | Y | Z | M.p. [°C.] |
|---|---|---|---|---|---|---|---|---|---|
| 80 | O | n-$C_3H_7$ | H | $CH_3$ | $CH_3$ | O | N | N | |
| 81 | O | n-$C_3H_7$ | H | $OCH_3$ | $CH_3$ | O | N | N | |
| 82 | O | n-$C_3H_7$ | H | $OCH_3$ | $OCH_3$ | O | N | N | |
| 83 | O | n-$C_3H_7$ | H | $OCH_3$ | Cl | O | CH | N | |
| 84 | O | n-$C_3H_7$ | H | $OCF_2H$ | $CH_3$ | O | CH | N | |
| 85 | O | n-$C_3H_7$ | H | $OCF_2H$ | $OCF_2H$ | O | CH | N | |
| 86 | O | n-$C_3H_7$ | H | $OCH_3$ | Br | O | CH | N | |
| 87 | O | n-$C_3H_7$ | H | $OCH_3$ | $OC_2H_5$ | O | CH | N | |
| 88 | O | n-$C_3H_7$ | H | $OCH_3$ | $SCH_3$ | O | CH | N | |
| 89 | O | n-$C_3H_7$ | H | $OCH_3$ | $OC_2H_5$ | O | N | N | |
| 90 | O | n-$C_3H_7$ | H | $OCH_3$ | $OC_3H_7$ | O | CH | N | |
| 91 | O | n-$C_3H_7$ | H | $OCH_3$ | Cl | O | N | N | |
| 92 | O | n-$C_3H_7$ | H | Cl | $OC_2H_5$ | O | CH | N | |
| 93 | O | n-$C_3H_7$ | H | $OC_2H_5$ | $OC_2H_5$ | O | CH | N | |
| 94 | O | n-$C_3H_7$ | H | $C_2H_5$ | $OCH_3$ | O | CH | N | |
| 95 | O | n-$C_3H_7$ | H | $CF_3$ | $OCH_3$ | O | CH | N | |
| 96 | O | n-$C_3H_7$ | H | $OCH_2CF_3$ | $CH_3$ | O | CH | N | |
| 97 | O | n-$C_3H_7$ | H | $OCH_2CF_3$ | $OCH_3$ | O | CH | N | |
| 98 | O | n-$C_3H_7$ | H | $OCH_2CF_3$ | $OCH_2CF_3$ | O | CH | N | |
| 99 | O | n-$C_3H_7$ | H | $OCH_2CF_3$ | $OCH_3$ | O | N | N | |
| 100 | O | n-$C_3H_7$ | H | $OCH_3$ | $NHCH_3$ | O | N | N | |
| 101 | O | n-$C_3H_7$ | H | $OC_2H_5$ | $NHCH_3$ | O | N | N | |
| 102 | O | n-$C_3H_7$ | H | $C_2H_5$ | $OC_2H_5$ | O | N | N | |
| 103 | O | n-$C_3H_7$ | H | $OCH_3$ | $CH_3$ | O | N | N | |
| 104 | O | n-$C_3H_7$ | H | Cl | $CH_3$ | O | N | N | |
| 105 | O | n-$C_3H_7$ | H | $CH_3$ | $CH_3$ | O | N | N | |
| 106 | O | n-$C_3H_7$ | H | $OCH_3$ | $OCH_3$ | S | CH | N | |
| 107 | O | n-$C_3H_7$ | H | $OCH_3$ | $CH_3$ | S | CH | N | |
| 108 | O | n-$C_3H_7$ | H | $CH_3$ | $CH_3$ | S | CH | N | |
| 109 | O | n-$C_3H_7$ | H | $OCH_3$ | $OCH_3$ | S | N | N | |
| 110 | O | n-$C_3H_7$ | H | $OCH_3$ | $CH_3$ | S | N | N | |
| 111 | O | n-$C_3H_7$ | H | $CH_3$ | $CH_3$ | S | N | N | |
| 112 | O | i-$C_3H_7$ | H | $OCH_3$ | $OCH_3$ | O | CH | N | |
| 113 | O | i-$C_3H_7$ | $CH_3$ | $OCH_3$ | $OCH_3$ | O | CH | N | |
| 114 | O | i-$C_3H_7$ | $CH_3$ | $OCH_3$ | $CH_3$ | O | N | N | |
| 115 | O | i-$C_3H_7$ | H | $CH_3$ | $CH_3$ | O | CH | N | |
| 116 | O | i-$C_3H_7$ | H | $OCH_3$ | $CH_3$ | O | CH | N | |
| 117 | O | i-$C_3H_7$ | H | $CH_3$ | $CH_3$ | O | N | N | |
| 118 | O | i-$C_3H_7$ | H | $OCH_3$ | $CH_3$ | O | N | N | |
| 119 | O | i-$C_3H_7$ | H | $OCH_3$ | $OCH_3$ | O | N | N | |
| 120 | O | i-$C_3H_7$ | H | $OCH_3$ | Cl | O | CH | N | |
| 121 | O | i-$C_3H_7$ | H | $OCF_2H$ | $CH_3$ | O | CH | N | |
| 122 | O | i-$C_3H_7$ | H | $OCF_2H$ | $OCF_2H$ | O | CH | N | |
| 123 | O | i-$C_3H_7$ | H | $OCH_3$ | Br | O | CH | N | |
| 124 | O | i-$C_3H_7$ | H | $OCH_3$ | $OC_2H_5$ | O | CH | N | |
| 125 | O | i-$C_3H_7$ | H | $OCH_3$ | $SCH_3$ | O | CH | N | |
| 126 | O | i-$C_3H_7$ | H | $OCH_3$ | $OC_2H_5$ | O | N | N | |
| 127 | O | i-$C_3H_7$ | H | $OCH_3$ | $OC_3H_7$ | O | CH | N | |
| 128 | O | i-$C_3H_7$ | H | $OCH_3$ | Cl | O | N | N | |
| 129 | O | i-$C_3H_7$ | H | Cl | $OC_2H_5$ | O | CH | N | |
| 130 | O | i-$C_3H_7$ | H | $OC_2H_5$ | $OC_2H_5$ | O | CH | N | |
| 131 | O | i-$C_3H_7$ | H | $C_2H_5$ | $OCH_3$ | O | CH | N | |
| 132 | O | i-$C_3H_7$ | H | $CF_3$ | $OCH_3$ | O | CH | N | |
| 133 | O | i-$C_3H_7$ | H | $OCH_2CF_3$ | $CH_3$ | O | CH | N | |
| 134 | O | i-$C_3H_7$ | H | $OCH_2CF_3$ | $OCH_3$ | O | CH | N | |
| 135 | O | i-$C_3H_7$ | H | $OCH_2CF_3$ | $OCH_2CF_3$ | O | CH | N | |
| 136 | O | i-$C_3H_7$ | H | $OCH_2CF_3$ | $OCH_3$ | O | N | N | |
| 137 | O | i-$C_3H_7$ | H | $OCH_3$ | $NHCH_3$ | O | N | N | |
| 138 | O | i-$C_3H_7$ | H | $OC_2H_5$ | $NHCH_3$ | O | N | N | |
| 139 | O | i-$C_3H_7$ | H | $C_2H_5$ | $OC_2H_5$ | O | N | N | |
| 140 | O | i-$C_3H_7$ | H | $OCH_3$ | $CH_3$ | O | N | N | |
| 141 | O | i-$C_3H_7$ | H | Cl | $CH_3$ | O | N | N | |
| 142 | O | i-$C_3H_7$ | H | $CH_3$ | $CH_3$ | O | N | N | |
| 143 | O | i-$C_3H_7$ | H | $OCH_3$ | $OCH_3$ | S | CH | N | |
| 144 | O | i-$C_3H_7$ | H | $OCH_3$ | $CH_3$ | S | CH | N | |
| 145 | O | i-$C_3H_7$ | H | $CH_3$ | $CH_3$ | S | CH | N | |

TABLE 6-continued

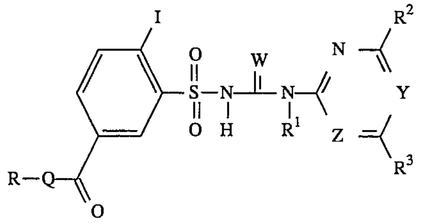

| Ex. No. | Q | R | $R^1$ | $R^2$ | $R^3$ | W | Y | Z | M.p. [°C.] |
|---|---|---|---|---|---|---|---|---|---|
| 146 | O | i-$C_3H_7$ | H | $OCH_3$ | $OCH_3$ | S | N | N | |
| 147 | O | i-$C_3H_7$ | H | $OCH_3$ | $CH_3$ | S | N | N | |
| 148 | O | i-$C_3H_7$ | H | $CH_3$ | $CH_3$ | S | N | N | |
| 149 | O | $CH_2CH-CH_2$ | H | $OCH_3$ | $OCH_3$ | O | CH | N | |
| 150 | O | $CH_2CH=CH_2$ | $CH_3$ | $OCH_3$ | $OCH_3$ | O | CH | N | |
| 151 | O | $CH_2CH=CH_2$ | $CH_3$ | $OCH_3$ | $CH_3$ | O | N | N | |
| 152 | O | $CH_2CH=CH_2$ | H | $CH_3$ | $CH_3$ | O | CH | N | |
| 153 | O | $CH_2CH=CH_2$ | H | $OCH_3$ | $CH_3$ | O | CH | N | |
| 154 | O | $CH_2CH=CH_2$ | H | $CH_3$ | $CH_3$ | O | N | N | |
| 155 | O | $CH_2CH=CH_2$ | H | $OCH_3$ | $CH_3$ | O | N | N | |
| 156 | O | $CH_2CH=CH_2$ | H | $OCH_3$ | $OCH_3$ | O | N | N | |
| 157 | O | $CH_2CH=CH_2$ | H | $OCH_3$ | Cl | O | CH | N | |
| 158 | O | $CH_2CH=CH_2$ | H | $OCF_2H$ | $CH_3$ | O | CH | N | |
| 159 | O | $CH_2CH=CH_2$ | H | $OCF_2H$ | $OCF_2H$ | O | CH | N | |
| 160 | O | $CH_2CH=CH_2$ | H | $OCH_3$ | Br | O | CH | N | |
| 161 | O | $CH_2CH=CH_2$ | H | $OCH_3$ | $OC_2H_5$ | O | CH | N | |
| 162 | O | $CH_2CH=CH_2$ | H | $OCH_3$ | $SCH_3$ | O | CH | N | |
| 163 | O | $CH_2CH=CH_2$ | H | $OCH_3$ | $OC_2H_5$ | O | N | N | |
| 164 | O | $CH_2CH=CH_2$ | H | $OCH_3$ | $OC_3H_7$ | O | CH | N | |
| 165 | O | $CH_2CH=CH_2$ | H | $OCH_3$ | Cl | O | N | N | |
| 166 | O | $CH_2CH=CH_2$ | H | Cl | $OC_2H_5$ | O | CH | N | |
| 167 | O | $CH_2CH=CH_2$ | H | $OC_2H_5$ | $OC_2H_5$ | O | CH | N | |
| 168 | O | $CH_2CH=CH_2$ | H | $C_2H_5$ | $OCH_3$ | O | CH | N | |
| 169 | O | $CH_2CH=CH_2$ | H | $CF_3$ | $OCH_3$ | O | CH | N | |
| 170 | O | $CH_2CH=CH_2$ | H | $OCH_2CF_3$ | $CH_3$ | O | CH | N | |
| 171 | O | $CH_2CH=CH_2$ | H | $OCH_2CF_3$ | $OCH_3$ | O | CH | N | |
| 172 | O | $CH_2CH=CH_2$ | H | $OCH_2CF_3$ | $OCH_2CF_3$ | O | CH | N | |
| 173 | O | $CH_2CH=CH_2$ | H | $OCH_2CF_3$ | $OCH_3$ | O | N | N | |
| 174 | O | $CH_2CH=CH_2$ | H | $OCH_3$ | $NHCH_3$ | O | N | N | |
| 175 | O | $CH_2CH=CH_2$ | H | $OC_2H_5$ | $NHCH_3$ | O | N | N | |
| 176 | O | $CH_2CH=CH_2$ | H | $C_2H_5$ | $OC_2H_5$ | O | N | N | |
| 177 | O | $CH_2CH=CH_2$ | H | $OCH_3$ | $CH_3$ | O | N | N | |
| 178 | O | $CH_2CH=CH_2$ | H | Cl | $CH_3$ | O | N | N | |
| 179 | O | $CH_2CH=CH_2$ | H | $CH_3$ | $CH_3$ | O | N | N | |
| 180 | O | $CH_2CH=CH_2$ | H | $OCH_3$ | $OCH_3$ | S | CH | N | |
| 181 | O | $CH_2CH=CH_2$ | H | $OCH_3$ | $CH_3$ | S | CH | N | |
| 182 | O | $CH_2CH=CH_2$ | H | $CH_3$ | $CH_3$ | S | CH | N | |
| 183 | O | $CH_2CH=CH_2$ | H | $OCH_3$ | $OCH_3$ | S | N | N | |
| 184 | O | $CH_2CH=CH_2$ | H | $OCH_3$ | $CH_3$ | S | N | N | |
| 185 | O | $CH_2CH=CH_2$ | H | $CH_3$ | $CH_3$ | S | N | N | |
| 186 | O | $CH_2C\equiv CH$ | H | $OCH_3$ | $OCH_3$ | O | CH | N | |
| 187 | O | $CH_2C\equiv CH$ | $CH_3$ | $OCH_3$ | $OCH_3$ | O | CH | N | |
| 188 | O | $CH_2C\equiv CH$ | $CH_3$ | $OCH_3$ | $CH_3$ | O | N | N | |
| 189 | O | $CH_2C\equiv CH$ | H | $CH_3$ | $CH_3$ | O | CH | N | |
| 190 | O | $CH_2C\equiv CH$ | H | $OCH_3$ | $CH_3$ | O | CH | N | |
| 191 | O | $CH_2C\equiv CH$ | H | $CH_3$ | $CH_3$ | O | N | N | |
| 192 | O | $CH_2C\equiv CH$ | H | $OCH_3$ | $CH_3$ | O | N | N | |
| 193 | O | $CH_2C\equiv CH$ | H | $OCH_3$ | $OCH_3$ | O | N | N | |
| 194 | O | $CH_2C\equiv CH$ | H | $OCH_3$ | Cl | O | CH | N | |
| 195 | O | $CH_2C\equiv CH$ | H | $OCF_2H$ | $CH_3$ | O | CH | N | |
| 196 | O | $CH_2C\equiv CH$ | H | $OCF_2H$ | $OCF_2H$ | O | CH | N | |
| 197 | O | $CH_2C\equiv CH$ | H | $OCH_3$ | Br | O | CH | N | |
| 198 | O | $CH_2C\equiv CH$ | H | $OCH_3$ | $OC_2H_5$ | O | CH | N | |
| 199 | O | $CH_2C\equiv CH$ | H | $OCH_3$ | $SCH_3$ | O | CH | N | |

TABLE 6-continued

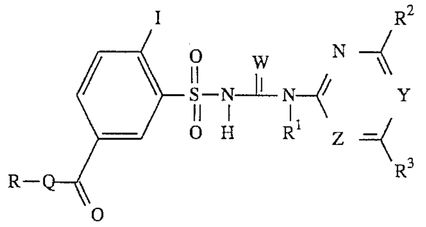

| Ex. No. | Q | R | $R^1$ | $R^2$ | $R^3$ | W | Y | Z | M.p. [°C.] |
|---|---|---|---|---|---|---|---|---|---|
| 200 | O | $CH_2C{\equiv}CH$ | H | $OCH_3$ | $OC_2H_5$ | O | N | N | |
| 201 | O | $CH_2C{\equiv}CH$ | H | $OCH_3$ | $OC_3H_7$ | O | CH | N | |
| 202 | O | $CH_2C{\equiv}CH$ | H | $OCH_3$ | Cl | O | N | N | |
| 203 | O | $CH_2C{\equiv}CH$ | H | Cl | $OC_2H_5$ | O | CH | N | |
| 204 | O | $CH_2C{\equiv}CH$ | H | $OC_2H_5$ | $OC_2H_5$ | O | CH | N | |
| 205 | O | $CH_2C{\equiv}CH$ | H | $C_2H_5$ | $OCH_3$ | O | CH | N | |
| 206 | O | $CH_2C{\equiv}CH$ | H | $CF_3$ | $OCH_3$ | O | CH | N | |
| 207 | O | $CH_2C{\equiv}CH$ | H | $OCH_2CH_3$ | $CH_3$ | O | CH | N | |
| 208 | O | $CH_2C{\equiv}CH$ | H | $OCH_2CF_3$ | $OCH_3$ | O | CH | N | |
| 209 | O | $CH_2C{\equiv}CH$ | H | $OCH_2CF_3$ | $OCH_2CF_3$ | O | CH | N | |
| 210 | O | $CH_2C{\equiv}CH$ | H | $OCH_2CF_3$ | $OCH_3$ | O | N | N | |
| 211 | O | $CH_2C{\equiv}CH$ | H | $OCH_3$ | $NHCH_3$ | O | N | N | |
| 212 | O | $CH_2C{\equiv}CH$ | H | $OC_2H_5$ | $NHCH_3$ | O | N | N | |
| 213 | O | $CH_2C{\equiv}CH$ | H | $C_2H_5$ | $OC_2H_5$ | O | N | N | |
| 214 | O | $CH_2C{\equiv}CH$ | H | $OCH_3$ | $CH_3$ | O | N | N | |
| 215 | O | $CH_2C{\equiv}CH$ | H | Cl | $CH_3$ | O | N | N | |
| 216 | O | $CH_2C{\equiv}CH$ | H | $CH_3$ | $CH_3$ | O | N | N | |
| 217 | O | $CH_2C{\equiv}CH$ | H | $OCH_3$ | $OCH_3$ | S | CH | N | |
| 218 | O | $CH_2C{\equiv}CH$ | H | $OCH_3$ | $CH_3$ | S | CH | N | |
| 219 | O | $CH_2C{\equiv}CH$ | H | $CH_3$ | $CH_3$ | S | CH | N | |
| 220 | O | $CH_2C{\equiv}CH$ | H | $OCH_3$ | $OCH_3$ | S | N | N | |
| 221 | O | $CH_2C{\equiv}CH$ | H | $OCH_3$ | $CH_3$ | S | N | N | |
| 222 | O | $CH_2C{\equiv}CH$ | H | $CH_3$ | $CH_3$ | S | N | N | |
| 223 | O | n-$C_4H_9$ | H | $OCH_3$ | $OCH_3$ | O | CH | N | |
| 224 | O | n-$C_4H_9$ | $CH_3$ | $OCH_3$ | $OCH_3$ | O | CH | N | |
| 225 | O | n-$C_4H_9$ | $CH_3$ | $OCH_3$ | $CH_3$ | O | N | N | |
| 226 | O | n-$C_4H_9$ | H | $CH_3$ | $CH_3$ | O | CH | N | |
| 227 | O | n-$C_4H_9$ | H | $OCH_3$ | $CH_3$ | O | CH | N | |
| 228 | O | n-$C_4H_9$ | H | $CH_3$ | $CH_3$ | O | N | N | |
| 229 | O | n-$C_4H_9$ | H | $OCH_3$ | $CH_3$ | O | N | N | |
| 230 | O | n-$C_4H_9$ | H | $OCH_3$ | $OCH_3$ | O | N | N | |
| 231 | O | i-$C_4H_9$ | H | $OCH_3$ | $OCH_3$ | O | CH | N | |
| 232 | O | i-$C_4H_9$ | $CH_3$ | $OCH_3$ | $OCH_3$ | O | CH | N | |
| 233 | O | i-$C_4H_9$ | $CH_3$ | $OCH_3$ | $CH_3$ | O | N | N | |
| 234 | O | i-$C_4H_9$ | H | $CH_3$ | $CH_3$ | O | CH | N | |
| 235 | O | i-$C_4H_9$ | H | $OCH_3$ | $CH_3$ | O | CH | N | |
| 236 | O | i-$C_4H_9$ | H | $CH_3$ | $CH_3$ | O | N | N | |
| 237 | O | i-$C_4H_9$ | H | $OCH_3$ | $CH_3$ | O | N | N | |
| 238 | O | i-$C_4H_9$ | H | $OCH_3$ | $OCH_3$ | O | N | N | |
| 239 | O | sec. $-C_4H_9$ | H | $OCH_3$ | $OCH_3$ | O | CH | N | |
| 240 | O | sec. $-C_4H_9$ | $CH_3$ | $OCH_3$ | $OCH_3$ | O | CH | N | |
| 241 | O | sec. $-C_4H_9$ | $CH_3$ | $OCH_3$ | $CH_3$ | O | N | N | |
| 242 | O | sec. $-C_4H_9$ | H | $CH_3$ | $CH_3$ | O | CH | N | |
| 243 | O | sec. $-C_4H_9$ | H | $OCH_3$ | $CH_3$ | O | CH | N | |
| 244 | O | sec. $-C_4H_9$ | H | $CH_3$ | $CH_3$ | O | N | N | |
| 245 | O | sec. $-C_4H_9$ | H | $OCH_3$ | $CH_3$ | O | N | N | |
| 246 | O | sec. $-C_4H_9$ | H | $OCH_3$ | $OCH_3$ | O | N | N | |

TABLE 6-continued

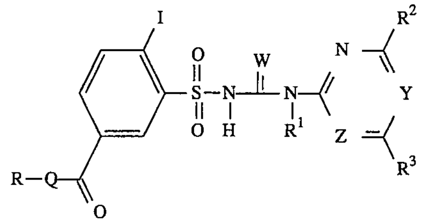

| Ex. No. | Q | R | $R^1$ | $R^2$ | $R^3$ | W | Y | Z | M.p. [°C.] |
|---|---|---|---|---|---|---|---|---|---|
| 247 | O | $t\text{-}C_4H_9$ | H | $OCH_3$ | $OCH_3$ | O | CH | N | |
| 248 | O | $t\text{-}C_4H_9$ | $CH_3$ | $OCH_3$ | $OCH_3$ | O | CH | N | |
| 249 | O | $t\text{-}C_4H_9$ | $CH_3$ | $OCH_3$ | $CH_3$ | O | N | N | |
| 250 | O | $t\text{-}C_4H_9$ | H | $CH_3$ | $CH_3$ | O | CH | N | |
| 251 | O | $t\text{-}C_4H_9$ | H | $OCH_3$ | $CH_3$ | O | CH | N | |
| 252 | O | $t\text{-}C_4H_9$ | H | $CH_3$ | $CH_3$ | O | N | N | |
| 253 | O | $t\text{-}C_4H_9$ | H | $OCH_3$ | $CH_3$ | O | N | N | |
| 254 | O | $t\text{-}C_4H_9$ | H | $OCH_3$ | $OCH_3$ | O | N | N | |
| 255 | O | $CH_2CH_2Cl$ | H | $OCH_3$ | $OCH_3$ | O | CH | N | |
| 256 | O | $CH_2CH_2Cl$ | $CH_3$ | $OCH_3$ | $OCH_3$ | O | CH | N | |
| 257 | O | $CH_2CH_2Cl$ | $CH_3$ | $OCH_3$ | $CH_3$ | O | N | N | |
| 258 | O | $CH_2CH_2Cl$ | H | $CH_3$ | $CH_3$ | O | CH | N | |
| 259 | O | $CH_2CH_2Cl$ | H | $OCH_3$ | $CH_3$ | O | CH | N | |
| 260 | O | $CH_2CH_2Cl$ | H | $CH_3$ | $CH_3$ | O | N | N | |
| 261 | O | $CH_2CH_2Cl$ | H | $OCH_3$ | $CH_3$ | O | N | N | |
| 262 | O | $CH_2CH_2Cl$ | H | $OCH_3$ | $OCH_3$ | O | N | N | |
| 263 | O | $CH_2CH_2OCH_3$ | H | $OCH_3$ | $OCH_3$ | O | CH | N | |
| 264 | O | $CH_2CH_2OCH_3$ | $CH_3$ | $OCH_3$ | $OCH_3$ | O | CH | N | |
| 265 | O | $CH_2CH_2OCH_3$ | $CH_3$ | $OCH_3$ | $CH_3$ | O | N | N | |
| 266 | O | $CH_2CH_2OCH_3$ | H | $CH_3$ | $CH_3$ | O | CH | N | |
| 267 | O | $CH_2CH_2OCH_3$ | H | $OCH_3$ | $CH_3$ | O | CH | N | |
| 268 | O | $CH_2CH_2OCH_3$ | H | $CH_3$ | $CH_3$ | O | N | N | |
| 269 | O | $CH_2CH_2OCH_3$ | H | $OCH_3$ | $CH_3$ | O | N | N | |
| 270 | O | $CH_2CH_2OCH_3$ | H | $OCH_3$ | $OCH_3$ | O | N | N | |
| 271 | O | $c\text{-}C_6H_{11}$ | H | $OCH_3$ | $OCH_3$ | O | CH | N | |
| 272 | O | $c\text{-}C_6H_{11}$ | $CH_3$ | $OCH_3$ | $OCH_3$ | O | CH | N | |
| 273 | O | $c\text{-}C_6H_{11}$ | $CH_3$ | $OCH_3$ | $CH_3$ | O | N | N | |
| 274 | O | $c\text{-}C_6H_{11}$ | H | $CH_3$ | $CH_3$ | O | CH | N | |
| 275 | O | $c\text{-}C_6H_{11}$ | H | $OCH_3$ | $CH_3$ | O | CH | N | |
| 276 | O | $c\text{-}C_6H_{11}$ | H | $CH_3$ | $CH_3$ | O | N | N | |
| 277 | O | $c\text{-}C_6H_{11}$ | H | $OCH_3$ | $CH_3$ | O | N | N | |
| 278 | O | $c\text{-}C_6H_{11}$ | H | $OCH_3$ | $OCH_3$ | O | N | N | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleylmethyltauride as wetting and dispersing agent, and grinding the mixture in a pinned disk mill.

c) A dispersion concentrate which is readily dispersible in water is obtained by mixing 20 parts by weight of a compound of the formula (I) with 6 parts by weight of alkylphenol polyglycol ether ((R)Triton X 207), 3 parts by weight of isotridecanol polyglycol ether (8 EO) and 71 parts by weight of paraffinic mineral oil (boiling range for example approx. 255° up to above 277° C.), and grinding the mixture in a ball mill to a fineness of below 5 microns.

d) An emulsifiable concentrate is obtained from 15 parts by weight of a compound of the formula (I), 75 parts by weight of cyclohexane as solvent and 10 parts by weight of ethoxylated nonylphenol as emulsifier.

e) Water-dispersible granules are obtained by mixing

| | |
|---|---|
| 75 parts by weight | of a compound of the formula (I), |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, |

grinding the mixture on a pinned disk mill, and granulating the powder in a fluidized bed by spraying on water as granulation liquid.

f) Alternatively, water-dispersible granules are obtained by homogenizing and precomminuting

| | |
|---|---|
| 25 parts by weight | of a compound of the formula (I), |
| 5 parts by weight | of sodium 2,2'-dinaphthylmethane-6,6'-disulfonate, |
| 2 parts by weight | of sodium oleylmethyltauride, |
| 1 part by weight | of polyvinyl alcohol, |
| 17 parts by weight | of calcium carbonate and |
| 50 parts by weight | of water |

on a colloid mill, subsequently grinding the mixture on a bead mill, and atomizing and drying the resulting suspension in a spray tower by means of a single-substance nozzle.

g) Extruder granules are obtained by mixing 20 parts by weight of active substance, 3 parts by weight of sodium ligninsulfonate, 1 part by weight of carboxymethylcellulose and 76 parts by weight of kaolin, grinding the mixture and moistening it with water. This mixture is extruded and subsequently dried in a stream of air.

C. Biological Examples

The damage to the weed plants, or the tolerance by the crop plants, was scored using a key in which the effectiveness is expressed by figures from 0 to 5. The figures have the following meaning:

0=no effect or damage

1=0 to 20% effect or damage

2=20 to 40% effect or damage

3=40 to 60% effect or damage

4=60 to 80% effect or damage

5=80 to 100% effect or damage

1. Pre-emergence effect on weeds

Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of aqueous suspensions or emulsions at an application rate of 600–800 l of water/ha (converted), in various dosages. After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures in Table 7, the compounds according to the invention have a good herbicidal pre-emergence action against a broad range of grass weeds and dicotyledon weeds.

TABLE 7

| Active substance | Dosage rate in | Pre-emergence effect | | | | | |
|---|---|---|---|---|---|---|---|
| | | Herbicidal effect | | | | | |
| Tab./Ex. | kg of ai/ha | STME | CRSE | SIAL | LOMU | ECCR | AVSA |
| 5/1 | 0.3 | 5 | 5 | 4 | 3 | 3 | 3 |
| 3/1 | 0.3 | 5 | 5 | 5 | 5 | 5 | 4 |

Abbreviations:
STME = Stellaria media
CRSE = Chrysanthemum segetum
SIAL = Sinapis alba
LOMU = Lolium multiflorum
ECCR = Echinochloa crus-galli
AVSA = Avena sativa
a.i. = Active ingredient Similarly good activities are generally also found in the case of the other compounds of Tables 2 to 7.

2. Post-emergence effect on weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 l of water/ha (converted) and, after the test plants had remained in the greenhouse for about 3–4 weeks under ideal growth conditions, the effect of the preparations was scored visually by comparison with untreated controls.

The agents according to the invention also have a good herbicidal post-emergence action against a broad range of economically important grass weeds and dicotyledon weeds (Table 8).

TABLE 8

| | | Post-emergence effect | | | | | |
|---|---|---|---|---|---|---|---|
| Active substance | Dosage rate in | Herbicidal effect | | | | | |
| Tab./Ex. | kg of ai/ha | STME | CRSE | SIAL | LOMU | ECCR | AVSA |
| 3/1 | 0.3 | 5 | 5 | 5 | 5 | 5 | 2 |

Abbreviations:
STME = Stellaria media
CRSE = Chrysanthemum segetum
SIAL = Sinapis alba
LOMU = Lolium multiflorum
ECCR = Echinochloa crus-galli
AVSA = Avena sativa
a.i. = Active ingredient Similarly good activities are generally also found in the case of the other compounds of Tables 2 to. 7. Compared with compounds of EP-A-7687 or US-A-4,556,898, the compounds of the formula I according to the invention generally exhibit better activities against problem weeds such as *Galium aparine* or *Echinochloa crus-galli.*

3. Tolerance by crop plants

In further greenhouse experiments, seeds of a substantial number of crop plants and weeds were placed in sandy loam soil and covered with soil.

Some of the pots were treated immediately as described under 1., and the remaining pots were placed in a greenhouse until the plants had developed two to three true leaves and then sprayed with various dosages of the substances according to the invention, as described under 2.

Visual scoring four to five weeks after the application and after the plants had been in the greenhouse revealed that the compounds according on the invention did not inflict any damage on dicotyledon crops such as, for example, soya, cotton, oilseed rape, sugar beet and potatoes when used pre- and post-emergence, even when high dosages of active substance were used. Moreover, some substances also left Gramineae crops such as, for example, barley, wheat, rye, Sorghum species, maize or rice unharmed. The compounds according to the invention therefore have a high selectivity when used to control undesired plant growth in agricultural crops. Compared with the compound of US-A-4,566,898 (cf. compound of the formula (3)) or Example 80 of EP-A-0,291,851, the compounds of the formula I according to the invention generally exhibit a better selectivity, in particular in the control of problem weeds such as *Galium aparine* or *Echinochloa crus-galli* in crops of useful plants.

4. Herbicidal effect when used in rice

Tubers and rhizomes or young plants or seeds of various rice weeds such as Cyperus species, Eleocharis, Scirpus and Echinochloa were placed or planted in sealed plastic pots containing special rice soil and flooded with water up to 1 cm above soil level. The same procedure was applied to rice plants.

Used pre-emergence, i.e. 3–4 days after transplanting, the compounds according to the invention were poured into the stagnant water in the form of aqueous suspensions or emulsions, or scattered into the water in the form of granules.

In each case three weeks later, the herbicidal effect and any harmful effect on rice were scored visually. The results show that the compounds according to the invention are suitable for selective weed control in rice. Compared with rice herbicides existing to date, the compounds according to the invention are distinguished by the fact that they effectively control a large number of weeds which germinate from perennial organs, in particular also weeds which are difficult to control, while being tolerated by rice.

We claim:

1. A compound of formula (II)

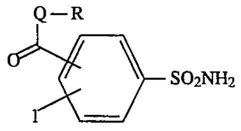

wherein

Q is an oxygen atom, sulfur atom or a group of formula $—N(R^4)—$, $R^4$ is hydrogen, $(C_1–C_4)$alkyl or $(C_1–C_4)$alkoxy, R is hydrogen; $(C_1–C_{12})$alkyl; $(C_2–C_{10})$alkenyl; $(C_2–C_{10})$alkynyl; $(C_1–C_6)$alkyl, which is monosubstituted to tetrasubstituted by radicals selected from the group consisting of halogen, $(C_1–C_4)$alkoxy-, $(C_1–C_4)$thio-alkyl, —CN, $(C_2–C_5)$alkoxycarbonyl and $(C_2–C_6)$alkenyl; $(C_3–C_8)$cycloalkyl which is unsubstituted or substituted by radicals selected from the group consisting of $(C_1–C_4)$-alkyl, $(C_1–C_4)$alkoxy, $(C_1–C_4)$alkylthio and halogen; $(C_5–C_8)$cycloalkenyl; phenyl$(C_1–C_4)$alkyl which is unsubstituted or substituted in the phenyl radical; or a radical of the formulae A-1 to A-10

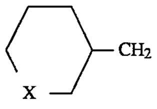

A-1

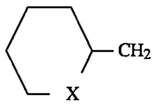

A-2

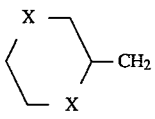

A-3

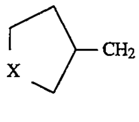

A-4

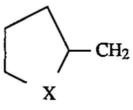

A-5

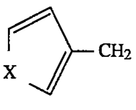

A-6

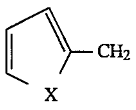

A-7

-continued

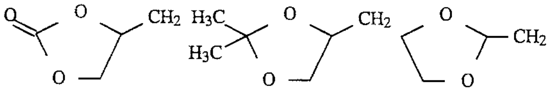

A-8 A-9 A-10 and

X is O, S, S(O) or $SO_2$, with the exception of 3-aminosulfonyl-4-iodobenzoic acid.

2. A compound of formula (II) as claimed in claim 1, wherein

R is hydrogen; $(C_1-C_6)$alkyl; $(C_2-C_6)$alkenyl; $(C_2-C_6)$alkynyl; $(C_1-C_4)$alkyl which is monosubstituted to tetrasubstituted by radicals selected from the group consisting of halogen, $(C_1-C_2)$alkoxy-, $(C_1-C_2)$thioalkyl, $(C_2-C_3)$alkoxycarbonyl and $(C_2-C_4)$alkenyl; $(C_5-C_6)$cycloalkyl which is unsubstituted or substituted by radicals selected from the group consisting of $(C_1-C_4)$alkyl, $(C_1-C_4)$alkoxy, $(C_1-C_4)$alkylthio and halogen; $(C_5-C_6)$cycloalkyl; benzyl which is unsubstituted or substituted in the phenyl radical by one to three radicals selected from the group consisting of halogen, $(C_1-C_2)$alkyl, $(C_1-C_2)$alkoxy, $(C_1-C_2)$haloalkyl, $(C_1-C_2)$thioalkyl and $(C_2-C_4)$alkocycarbonyl, or a radical of the formulae A-1 to A-10, as defined in claim 1, where X is O, S, S(O) or $SO_2$.

3. A compound of formula (II) as claimed in claim 1, wherein

R is hydrogen or $(C_1-C_2)$alkyl.

4. A compound of formula (II) as claimed in claim 1, wherein

Q is an oxygen atom, and

R is $C_1-C_4$-alkyl

5. The compound of formula (II) as claimed in claim 4, which is methyl 2-aminosulfonyl-6-iodobenzoate.

6. The compound of formula (II) as claimed in claim 4, which is ethyl 2-aminosulfonyl-6-iodobenzoate.

7. The compound of formula (II) as claimed in claim 4, which is methyl 2-aminosulfonyl-5-iodobenzoate.

8. The compound of formula (II) as claimed in claim 4, which is ethyl 2-aminosulfonyl-5-iodobenzoate.

9. The compound of formula (II) as claimed in claim 4, which is isopropyl 2-aminosulfonyl-5-iodobenzoate.

10. The compound of formula (II) as claimed in claim 4, which is methyl 2-aminosulfonyl-3-iodobenzoate.

11. The compound of formula (II) as claimed in claim 4, which is ethyl 2-aminosulfonyl-3-iodobenzoate.

12. The compound of formula (II) as claimed in claim 4, which is methyl 3-aminosulfonyl-2-iodobenzoate.

13. The compound of formula (II) as claimed in claim 4, which is ethyl 3-aminosulfonyl-2-iodobenzoate.

14. The compound of formula (II) as claimed in claim 4, which is methyl 3-aminosulfonyl-4-iodobenzoate.

15. A sulfonyl isocyanate of formula (VI)

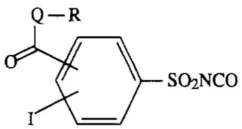

(VI)

wherein

Q is an oxygen atom, sulfur atom or a group of formula $-N(R^4)-$, $R^4$ is hydrogen, $(C_1-C_4)$-alkyl or $(C_1-C_4)$-alkoxy, R is hydrogen; $(C_1-C_{12})$alkyl; $(C_2-C_{10})$alkenyl;

$(C_2-C_{10})$alkynyl; $(C_1-C_6)$alkyl, which is monosubstituted to tetrasubstituted by radicals selected from the group consisting of halogen, $(C_1-C_4)$alkoxy-, $(C_1-C_4)$thioalkyl, —CN, $(C_2-C_5)$alkoxycarbonyl and $(C_2-C_6)$alkenyl; $(C_3-C_8)$cycloalkyl which is unsubstituted or substituted by radicals selected from the group consisting of $(C_1-C_4)$-alkyl, $(C_1-C_4)$alkoxy, $(C_1-C_4)$alkylthio and halogen; $(C_5-C_8)$cycloalkenyl; phenyl$(C_1-C_4)$alkyl which is unsubstituted or substituted in the phenyl radical; or a radical of the formulae A-1 to A-10

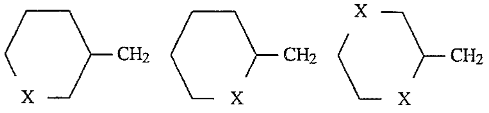

A-1 A-2 A-3

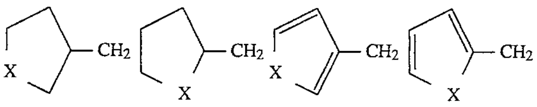

A-4 A-5 A-6 A-7

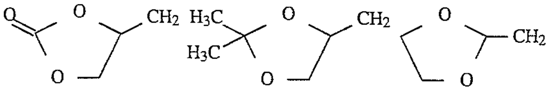

A-8 A-9 A-10 where

X is O, S, S(O) or $SO_2$.

16. A compound of formula (VI) as claimed in claim 15, wherein

R is hydrogen; $(C_1-C_6)$alkyl; $(C_2-C_6)$alkenyl;

$(C_2-C_6)$alkynyl; $(C_1-C_4)$alkyl which is monosubstituted to tetrasubstituted by radicals selected from the group consisting of halogen, $(C_1-C_2)$alkoxy-, $(C_1-C_2)$thioalkyl, $(C_2-C_3)$alkoxycarbonyl and $(C_2-C_4)$alkenyl; $(C_5-C_6)$cycloalkyl which is unsubstituted or substituted by radicals selected from the group consisting of $(C_1-C_4)$alkyl, $(C_1-C_4)$alkoxy, $(C_1-C_4)$alkylthio and halogen;

$(C_5-C_6)$ cycloalkyl; benzyl which is unsubstituted or substituted in the phenyl radical by one to three radicals selected from the group consisting of halogen, $(C_1-C_2)$alkyl, $(C_1-C_2)$alkoxy, $(C_1-C_2)$haloalkyl, $(C_1-C_2)$thioalkyl and $(C_2-C_4)$alkocycarbonyl, or a radical of the formulae A-1 to A-10, as defined in claim 15, where X is O, S, S(O) or $SO_2$.

17. A compound of formula (VI) as claimed in claim 15, wherein

Q is an oxygen atom, and

R is $(C_1-C_4)$alkyl.

18. The compound of formula (VI) as claimed in claim 17, which is methyl 2-isocyanatosulfonyl-6 -iodobenzoate or ethyl 2-isocyanatosulfonyl-6-iodobenzoate.

19. The compound of formula (VI) as claimed in claim 17, which is methyl 2-isocyanatosulfonyl-4 -iodobenzoate or ethyl 2-isocyanatosulfonyl-4 -iodobenzoate or isopropyl 2-isocyanatosulfonyl-4-iodobenzoate.

20. The compound of formula (VI) as claimed in claim 17, which is methyl 2-isocyanatosulfonyl-3 -iodobenzoate or ethyl 2-isocyanatosulfonyl-4-iodobenzoate.

21. The compound of formula (VI) as claimed in claim 17, which is methyl 3-isocyanatosulfonyl-2 -iodobenzoate or ethyl 3-isocyanatosulfonyl-2 -iodobenzoate or n-propyl 3-isocyanatosulfonyl-2 -iodobenzoate or isopropyl 3-isocyanatosulfonyl-2-iodobenzoate.

* * * * *